(12) United States Patent
Krystal

(10) Patent No.: US 6,218,162 B1
(45) Date of Patent: Apr. 17, 2001

(54) SH2-CONTAINING INOSITOL-PHOSPHATASE

(76) Inventor: Gerald Krystal, 601West 10th Street, Vancouver, British Columbia (CA), V52 1L3

(*) Notice: Subject to any disclaimer, the term of this patent is extended or adjusted under 35 U.S.C. 154(b) by 0 days.

(21) Appl. No.: 08/664,962

(22) Filed: Jun. 14, 1996

Related U.S. Application Data

(60) Provisional application No. 60/006,063, filed on Sep. 27, 1995, provisional application No. 60/007,788, filed on Nov. 30, 1995, and provisional application No. 60/015,217, filed on Apr. 9, 1996.

(51) Int. Cl.[7] .............................. C12N 9/16; C07K 14/00

(52) U.S. Cl. ............................................ 435/196; 530/350

(58) Field of Search ............................... 435/196; 530/350

(56) References Cited

PUBLICATIONS

Kavanaugh, W.M. et al. "Multiple forms of an inositol polyphosphate 5–phosphatase form signaling complexes with Shc and Grb2." Current Biology, vol. 6, No. 4(Apr. 1, 1996), pp. 438–445, Apr. 1996.*

Alberts, B. et al. Molecular Biology of the Cell, Second Edition. N.Y., Garland Publishing, Inc., 1989, pp. 258–266.*

* cited by examiner

*Primary Examiner*—Rebecca E. Prouty
*Assistant Examiner*—Richard Hutson
(74) *Attorney, Agent, or Firm*—Merchant & Gould P.C.

(57) ABSTRACT

Novel SH2-containing inositol-phosphatase which has a src homology 2 (SH2) domain and exhibits phosphoIns-5-ptase activity, and nucleic acid molecules encoding the novel protein are disclosed. The invention also relates to methods for identifying substances which affect the binding of the protein to Shc and/or its phosphoIns-5-ptase activity and methods for screening for agonists or antagonists of the binding of the protein and Shc.

2 Claims, 27 Drawing Sheets

1   MPAMVPGWNHGNITRSKAEELLSRAGKDGSFLVRASESIPRACALCVLFR
51  NCVYTYRILPNEDDKFTVQASEGVPMRFFTKLDQLIDFYKKENMGLVTHL
101 QYPVPLEEEDAIDEAEEDTESVMSPPELPPRNIPMSAGPSEAKDLPLATE
151 NPRAPEVTRLSLSETLFQRLQSMDTSGLPEEHLKAIQDYLSTQLLLDSDF
201 LKTGSSNLPHLKKLMSLLCKELHGEVIRTLPSLESLQRLFDQQLSPGLRP
251 RPQVPGEASPITMVAKLSQLTSLLSSIEDKVKSLLHEGSESTNRRSLIPP
301 VTFEVKSESLGIPQKMHLKVDVESGKLIVKKSKDGSEDKFYSHKKILQLI
351 KSQKFLNKLVILVETEKEKILRKEYVFADSKKREGFCQLLQQMKNKHSEQ
401 PEPDMITIFIGTWNMGNAPPPKKITSWFLSKGQGKTRDDSADYIPHDIYV
451 IGTQEDPLGEKEWLELLRHSLQEVTSMTFKTVAIHTLWNIRIVVLAKPEH
501 ENRISHICTDNVKTGIANTLGNKGAVGVSFMFNGTSLGFVNSHLTSGSEK
551 KLRRNQNYMNILRFLALGDKKLSPFNITHRFTHLFWLGDLNYRVELPTWE
601 AEAIIQKIKQQQYSDLLAHDQLLLERKDQKVFLHFEEEEITFAPTYRFER
651 LTRDKYAYTKQKATGMKYNLPSWCDRVLWKSYPLVHVVCQSYGSTSDIMT
701 SDHSPVFATFEAGVTSQFVSKNGPGTVDSQGQIEFLACYATLKTKSQTKF
751 YLEFHSSCLESFVKSQEGENEEGSEGEVVRFGETLPKLKPIISDPEYLL
801 DQHILISIKSSDSDESYGEGCIALRLETTEAQHPIYTPLTHHGEMTGHFR
851 GEIKLQTSQGKMREKLYDFVKTERDESSGMKCLKNLTSHDPMRQWEPSGR
901 VPACGVSSLNEMINPNYIGMGPFGQPLHGKSTLSPDQQLTAWSYDQLPKD
951 SSLGPGRGEGPPTPPSQPPLSPKKFSSSTTNRGPCPRVQEARPGDLGKVE
1001 ALLQEDLLLTKPEMFENPLYGSVSSFPKLVPRKEQESPKMLRKEPPPCPD
1051 PGISSPSIVLPKAQEVESVKGTSKQAPVPVLGPTPRIRSFTCSSSAEGRM
1101 TSGDKSQGKPKASASSQAPVPVKRPVKPSRSEMSQQTTPIPAPRPPLPVK
1151 SPAVLQLQHSKGRDYRDNTELPHHGKHRQEEGLLGRTAMQ

>BASE COUNT   1014 a  1147 c  1054 g   825 t
>ORIGIN
```
>      1 ccctggtagg agcagcagag gcaatttctg agaggcaaca ggcggcaggt ctcagcctag
>     61 agagggccct gaactactt gctggagtgt ccgtcctggg tggactgct gacccagtcc
>    121 aggagaccca tgcctgccat ggtccctggg tggaaccatg gcaacatcac ccgctccaag
>    181 gcagaggagc tactttccag agccggcaag gacgggagct tccttgtgcg tgccagcgag
>    241 tccatcccc gggcctgcgc actctgcgtg ctgttccgga attgtgttta cacttacagg
>    301 attctgccca atgaggacga taaattcact gttcaggcat ccgaaggtgt cccatgagg
>    361 ttcttcacga agctggacca gctcatcgac ttttacaaga aggaaaacat ggggctggtg
>    421 acccaccctgc agtacccgt gccctggag gaggaggatg ctattgatga ggctgaggag
>    481 gacactgaaa gtgtcatgtc accacctgag ctgcctccca gaaacattcc tatgtctgcc
>    541 gggcccagcg aggccaagga ccttcctctt gcaacagaga accccgagc ccctgaggtc
>    601 accggctga gtctctccga gacactgttt cagcgtctac agagcatgga taccagtggg
>    661 cttccccgagg agcacctgaa agccatccag gattatctga gcactcagct cctcctggat
>    721 tccgactttt tgaaaacggg ctccagcaac ctccctcacc tgaagaagct gatgtcactg
>    781 ctctgcaagg agctccatgg ggaagtcatc aggactctgc catccctgga gtctctgcag
>    841 aggttgtttg accaacagct ctccccaggc cttcgcccac gacctcaggt gcccggagag
>    901 gccagtccca tcaccatggt tgccaaactc agccaattga caagtctgct gtcttccatt
>    961 gaagataagg tcaagtcctt gctgcacgag ggctcagaat ctaccaacag gcgttcccct
>   1021 atccctccgg tcacctttga ggtgaagtca gagtccctgg gcattcctca gaaaatgcat
>   1081 ctcaaagtgg acgttgagtc tgggaaactg atcgttaaga agtccaagga tggttctgag
>   1141 gacaagttcc acagccacaa aaaaaatcctg cagctcatta gtcccagaa gtttctaaac
>   1201 aagttggtga ttttggtgga gacggagaag gagaaaatcc tgaggaagga atatgttttt
>   1261 gctgactcta agaaaagaga aggcttctgt caactcctgc agcagatga gaacaagcat
>   1321 tcggagcagc cagagcctga catgatcacc atcttcattg gcactggaa catgggtaat
>   1381 gcacccctc ccaagaagat cacgtcctgg tttctctcca aggggcaggg aaagacacgg
>   1441 gacgactctg ctgactacat cccccatgac atctatgtga ttggcaccca ggaggatccc
>   1501 cttggagaga aggagtggcc ggagctactc aggcactcc tgcaagaagt caccagcatg
>   1561 acatttaaaa cagttgccat ccacaccctc tggaacattc gcatagtggt gcttgccaag
>   1621 ccagagcatg agaatcggat cagccatatc tgcactgaca acgtgaagac aggcatcgcc
>   1681 aacaccctgg gaaacaaggg agcagtggga gtgtccttca tgttcaatgg aacctccttg
>   1741 gggttcgtca acagccactt gacttctgga agtgaaaaaa agctcaggag aaatcaaaac
>   1801 tatatgaaca tcctgcggtt cctggccctg ggagacaaga agctaagccc atttaacatc
>   1861 acccaccgct tcacccacct cttctggctt gggatctca actaccgcgt ggagctgccc
>   1921 acttgggagg cagaggccat catccagaag atcaagcaac agcagtattc agaccttctg
>   1981 gcccacgacc aactgctcct ggagaggaag gaccagaagg tcttcctgca ctttgaggag
>   2041 gaagagatca ccttcgcccc cacctatcga tttgaaagac tgacccggga caagtatgca
>   2101 tacacgaagc agaaagcaac agggatgaag tacaacttgc cgtcctggtg cgaccgagtc
>   2161 ctctggaagt cttacccgct ggtgcatgtg gtctgtcagt cctatgcag taccagtgac
>   2221 atcatgacga gtgaccacag ccctgtcttt gccacgtttg aagcaggagt cacatctcaa
>   2281 ttcgtctcca agaatggtcc tggcactgta gatagccaag ggcagatcga gtttctgca
>   2341 tgctacgcca cactgaagac caagtcccag actaagttct acttggagtt ccactcaagc
>   2401 tgcttagaga gttttgtcaa gagtcaggaa ggagagaatg aagagggaag tgaaggagag
>   2461 ctggtggtac ggtttggaga gactcttccc aagctaaagc ccattatctc tgaccccgag
>   2521 tacttactgg accagcatat cctgatcagc attaaatcct ctgacagtga cgagtcctat
>   2581 ggtgaaggct gcattgccct tcgcttggag accacagagg ctcagcatcc tatctacacg
>   2641 cctctcaccc accatgggga gatgactggc cacttcaggg gagagattaa gctgcagacc
>   2701 tcccagggca agatgaggga gaagctctat gactttgtga agacagagcg ggatgaatcc
>   2761 agtggaatga aatgcttgaa gaacctcacc agccatgacc ctatgaggca atgggagcct
>   2821 tctggcaggg tccctgcatg tggtgtctcc agcctcaatg agatgatcaa tccaaactac
>   2881 attggtatgg ggccttttgg acagccctg catgggaaat caaccctgtc cccagatcag
>   2941 caactcacag cttggagtta tgaccagcta cccaaagact cctccctggg gcctgggagg
>   3001 ggggagggtc ctccaacccc tccctcccaa ccacctctgt cgccaaagaa gttttcatct
>   3061 tccacaacca accgaggtcc ctgcccagg gtgcaagagg caagacctgg ggatctggga
>   3121 aaggtggaag ctctgctcca ggaggacctg ctgctgacga agcccgagat gtttgagaac
>   3181 ccactgtatg gatccgtgag ttccttccct aagctggtgc caggaaaga gcaggagtct
>   3241 cccaagatgc tgcggaagga gccccgcc tgtccagacc caggaatctc atcacccagc
>   3301 atcgtgctcc ccaaagccca agaggtggag agtgtcaagg ggacaagcaa acaggccct
>   3361 gtgcctgtcc ttggccccac accccggatc cgctccttta cctgttcttc ttctgctgag
>   3421 ggcagaatga ccagtgggga caagagccaa gggaagccca aggcctcagc cagttcccaa
>   3481 gccccagtgc cagtcaagag gcctgtcaag ccttccaggt cagaaatgac ccagcagaca
>   3541 acacccatcc cagctccacg gccaccccctg ccagtcaaga gtcctgctgt cctgcagctg
>   3601 caacattcca aaggcagaga ctaccgtgac aacacagaac tccccacca tggcaagcac
>   3661 cgccaagagg aggggctgct tggcaggact gccatgcagt gagctgctgg tgatcggagc
>   3721 ctggaggaac agcacaaagc agacctgcga cctctctcag gatgcctctc tcaggatgcc
>   3781 tcttggagga cctcctgcta gctcttcttg cctagcttca agtcccaggc tgtgtatttt
>   3841 ttttcaggaa acggcctcac ttctctgtgg tccaagaagt gtgctgctgg ctgccacact
>   3901 gtgcggcaga tgctaaagct ggatgacaaa cgcacgccat acagacagca gacagcggca
>   3961 ctgggtctca gaacttggat tcctgggcct tcttccagtc gccgttttaa agaaaggaac
>   4021 taacggagct gctcatccga
```

FIGURE 7

| | | |
|---|---|---|
| Gene | Locus: SHC1 | gi\|134475: 1..473 |
| Organism | HOMO SAPIENS (HUMAN) | gi\|134475: 1..473 |
| Sequence | 473 aa | |

```
  1 mnklsggggr rtrveggqlg geewtrhgsf vnkptrgwlh pndkvmgpgv
 51 sylvrymgcv evlqsmrald fntrtqvtre aislvceavp gakgatrrrk
101 pcsrplssil grsnlkfagm pitltvstss lnlmaadckq iianhhmqsi
151 sfasggdpdt aeyvayvakd pvnqrachil ecpeglaqdv istigqafel
201 rfkqylrnpp klvtphdrma gfdgsawdee eeeppdhqyy ndfpgkeppl 251 ggvvdmrlre gaapgaarpt apnaqtpshl gatlpvgqpv ggdpevrkqm
301 pppppcpgre lfddpsyvnv qnldkarqav ggagppnpai ngsaprdlfd
351 mkpfedalrv ppppqsvsma eqlrgepwfh gklsrreaea llqlngdflv
401 restttpgqy vltglqsgqp khlllvdpeg vvrtkdhrfe svshlisyhm
451 dnhlpiisag selclqqpve rkl
```

FIGURE 8

H.sapiens SHC mRNA.
ACCESSION  X68148
*FIELD*  NID
         g36453
KEYWORDS  SHC protein.
SOURCE    human.
  ORGANISM  Homo sapiens
         Eukaryotae; mitochondrial eukaryotes; Metazoa/Eumycota group;
         Metazoa; Eumetazoa; Bilateria; Coelomata; Deuterostomia; Chordata;
         Vertebrata; Gnathostomata; Osteichthyes; Sarcopterygii; Choanata;
         Tetrapoda; Amniota; Mammalia; Theria; Eutheria; Archonta; Primates;
         Catarrhini; Hominidae; Homo.
REFERENCE  1  (bases 1 to 3031)
  AUTHORS  Pelicci,P.
  TITLE    Direct Submission
  JOURNAL  Submitted (10-JUN-1992) to the EMBL/GenBank/DDBJ databases. P.
           Pelicci, Clinica Medica I, Policlinico Monteluce, Perugia 06100
           08854, ITALY
REFERENCE  2  (bases 1 to 3031)
  AUTHORS  Pelicci,G., Lanfrancone,L., Grignani,F., McGlade,J., Cavallo,F.,
           Forni,G., Nicoletti,I., Grignani,F., Pawson,T. and Pelicci,P.G.
  TITLE    A novel transforming protein (SHC) with an SH2 domain is implicated
           in mitogenic signal transduction
  JOURNAL  Cell 70 (1), 93-104 (1992)
  MEDLINE  92323554
FEATURES             Location/Qualifiers
     source          1..3031
                     /organism="Homo sapiens"
     CDS             82..1503
                     /codon_start=1
                     /product="SHC transforming protein"
                     /db_xref="PID:g36454"

/translation="MNKLSGGGGRRTRVEGGQLGGEEWTRHGSFVNKPTRGW
LHPNDK

VMGPGVSYLVRYMGCVEVLQSMRALDFNTRTQVTREAISLVCEAVPGAKGATR
RRKPC

SRPLSSILGRSNLKFAGMPITLTVSTSSLNLMAADCKQIIANHHMQSISFASGGDPD
T

AEYVAYVAKDPVNQRACHILECPEGLAQDVISTIGQAFELRFKQYLRNPPKLVTPH
DR

MAGFDGSAWDEEEEPPDHQYYNDFPGKEPPLGGVVDMRLREGAAPGAARPTAP

FIGURE 8 CONT'D

NAQT

PSHLGATLPVGQPVGGDPEVRKQMPPPPPCPGRELFDDPSYVNVQNLDKARQAV
GGAG

PPNPAINGSAPRDLFDMKPFEDALRVPPPPQSVSMAEQLRGEPWFHGKLSRREAE
ALL

QLNGDFLVRESTTTPGQYVLTGLQSGQPKHLLLVDPEGVVRTKDHRFESVSHLISY
HM
           DNHLPIISAGSELCLQQPVERKL"

BASE COUNT    664 a   855 c   809 g   703 t
ORIGIN
```
   1 gcggtaacct aagctggcag tggcgtgatc cggcaccaaa tcggcccgcg gtgcgtgcgg
  61 agactccatg aggccctgga catgaacaag ctgagtggag gcggcgggcg caggactcgg
 121 gtggaagggg gccagcttgg gggcgaggag tggacccgcc acgggagctt tgtcaataag
 181 cccacgcggg gctggctgca tcccaacgac aaagtcatgg gacccggggt ttcctacttg
 241 gttcggtaca tgggttgtgt ggaggtcctc cagtcaatgc gtgccctgga cttcaacacc
 301 cggactcagg tcaccaggga ggccatcagt ctggtgtgtg aggctgtgcc gggtgctaag
 361 ggggcgacaa ggaggagaaa gccctgtagc cgcccgctca gctctatcct ggggaggagt
 421 aacctgaaat ttgctggaat gccaatcact ctcaccgtct ccaccagcag cctcaacctc
 481 atggccgcag actgcaaaca gatcatcgcc aaccaccaca tgcaatctat ctcatttgca
 541 tccggcgggg atccggacac agccgagtat gtcgcctatg ttgccaaaga ccctgtgaat
 601 cagagagcct gccacattct ggagtgtccc gaagggcttg cccaggatgt catcagcacc
 661 attggccagg ccttcgagtt gcgcttcaaa caatacctca ggaacccacc caaactggtc
 721 accccctcatg acaggatggc tggctttgat ggctcagcat gggatgagga ggaggaagag
 781 ccacctgacc atcagtacta taatgacttc ccggggaagg aacccccctt ggggggggtg
 841 gtagacatga ggcttcggga aggagccgct ccaggggctg ctcgacccac tgcacccaat
 901 gcccagaccc ccagccactt gggagctaca ttgcctgtag acagcctgt tggggagat
 961 ccagaagtcc gcaaacagat gccacctcca ccacctgtc caggcagaga gcttttgat
1021 gatccctcct atgtcaacgt ccagaaccta gacaaggcc ggcaagcagt gggtggtgct
1081 gggccccccca atcctgctat caatggcagt gcaccccggg acctgtttga catgaagccc
1141 ttcgaagatg ctcttcgggt gcctccacct ccccagtcgg tgtccatggc tgagcagctc
1201 cgaggggagc cctggttcca tgggaagctg agccggcggg aggctgaggc actgctgcag
1261 ctcaatgggg acttcttggt acgggagagc acgaccacac tggccagta tgtgctcact
1321 ggcttgcaga gtgggcagcc taagcatttg ctactggtgg accctgaggg tgtggttcgg
1381 actaaggatc accgctttga aagtgtcagt caccttatca gctaccacat ggacaatcac
1441 ttgcccatca tctctgcggg cagcgaactg tgtctacagc aacctgtgga gcggaaactg
1501 tgatctgccc tagcgctctc ttccagaaga tgccctccaa tcctttccac cctattccct
1561 aactctcggg acctcgtttg ggagtgttct gtgggcttgg ccttgtgtca gagctgggag
1621 tagcatggac tctgggtttc atatccagct gagtgagagg gtttgagtca aaagcctggg
1681 tgagaatcct gcctctcccc aaacattaat caccaaagta ttaatgtaca gagtggcccc
1741 tcacctgggc ctttcctgtg ccaacctgat gccccttccc caagaaggtg agtgcttgtc
1801 atggaaaatg tcctgtggtg acaggcccag tggaacagtc acccttctgg gcaagggga
1861 acaaatcaca cctctgggct tcagggtatc ccagacccct ctcaacaccc gcccccccca
1921 tgtttaaact tgtgcctt gaccatctct taggtctaat gatattttat gcaaacagtt
```

FIGURE 8 CONT'D

```
1981 cttggacccc tgaattcttc aatgacaggg atgccaacac cttcttggct tctgggacct
2041 gtgttcttgc tgagcaccct ctccggtttg ggttgggata acagaggcag gagtggcagc
2101 tgtcccctct ccctggggat atgcaaccct tagagattgc cccagagccc cactcccggc
2161 caggcgggag atggacccct cccttgctca gtgcctcctg gccggggccc ctcaccccaa
2221 ggggtctgta tatacatttc ataaggcctg ccctcccatg ttgcatgcct atgtactctg
2281 cgccaaagtg cagcccttcc tcctgaagcc tctgccctgc ctccctttct gggagggcgg
2341 ggtgggggtg actgaatttg ggcctcttgt acagttaact ctcccaggtg gattttgtgg
2401 aggtgagaaa aggggcattg agactataaa gcagtagaca atccccacat accatctgta
2461 gagttggaac tgcattcttt taaagtttta tatgcatata ttttagggct gctagactta
2521 ctttcctatt ttcttttcca ttgcttattc ttgagcacaa aatgataatc aattattaca
2581 tttatacatc accttttga cttttccaag ccctttaca gctcttggca ttttcctcgc
2641 ctaggcctgt gaggtaactg ggatcgcacc ttttatacca gagacctgag gcagatgaaa
2701 tttatttcca tctaggacta gaaaaaacttg ggtctcttac cgcgagactg agaggcagaa
2761 gtcagcccga atgcctgtca gtttcatgga ggggaaacgc aaaacctgca gttcctgagt
2821 accttctaca ggcccggccc agcctaggcc cggggtggcc acaccacagc aagccggccc
2881 cccctctttt ggccttgtgg ataagggaga gttgaccgtt ttcatcctgg cctccttttg
2941 ctgtttggat gtttccacgg gtctcactta taccaaaggg aaaactcttc attaaagtcc
3001 cgtatttctt ctaaaaaaaa aaaaaaaaa a
//
```

FIGURE 9

```
            NCBI gi: 181975
FEATURES             Location/Qualifiers
    source           1..1109
                     /organism="Homo sapiens"
                     /sequenced_mol="cDNA to mRNA"
                     /tissue_type="brainstem"
                     /tissue_lib="gt11 human brainstem library"
    CDS              79..732
                     /gene="EGFRBP-GRB2"
                     /note="NCBI gi: 181976"
                     /codon_start=1
                     /product="epidermal growth factor receptor-binding protein
                     GRB2"
                     /translation="MEAIAKYDFKATADDELSFKRGDILKVLNEECDQNWYKAELNGK
                     DGFIPKNYIEMKPHPWFFGKIPRAKAEEMLSKQRHDGAFLIRESESAPGDFSLSVKFG
                     NDVQHFKVLRDGAGKYFLWVVKFNSLNELVDYHRSTSVSRNQQIFLRDIEQVPQQPTY
                     VQALFDFDPQEDGELGFRRGDFIHVMDNSDPNWWKGACHGQTGMFPRNYVTPVNRNV"
BASE COUNT       313 a     273 c     262 g     261 t
ORIGIN
        1 gccagtgaat tcgggggctc agccctcctc cctcccttcc ccctgcttca ggctgctgag
       61 cactgagcag cgctcagaat ggaagccatc gccaaatatg acttcaaagc tactgcagac
      121 gacgagctga gcttcaaaag gggggacatc ctcaaggttt tgaacgaaga atgtgatcag
      181 aactggtaca aggcagagct taatggaaaa gacggcttca ttcccaagaa ctacatagaa
      241 atgaaaccac atccgtggtt ttttggcaaa atccccagag ccaaggcaga agaaatgctt
      301 agcaaacagc ggcacgatgg ggcctttctt atccgagaga gtgagagcgc tcctggggac
      361 ttctccctct ctgtcaagtt tggaaacgat gtgcagcact caaggtgct ccgagatgga
      421 gccgggaagt acttcctctg ggtggtgaag ttcaattctt gaatgagct ggtggattat
      481 cacagatcta catctgtctc cagaaaccag cagatattcc tgcgggacat agaacaggtg
      541 ccacagcagc cgacatacgt ccaggccctc tttgactttg atccccagga ggatggagag
      601 ctgggcttcc gccggggaga tttatccat gtcatggata actcagaccc caactggtgg
      661 aaaggagctt gccacgggca gaccggcatg tttccccgca attatgtcac ccccgtgaac
      721 cggaacgtct aagagtcaag aagcaattat ttaaagaaag tgaaaaatgt aaaacacata
      781 caaaagaatt aaacccacaa gctgcctctg acagcagcct gtgagggagt gcagaacacc
      841 tggccgggtc accctgtgac cctctcactt tggttggaac tttaggggt gggagggggc
      901 gttggattta aaaatgccaa aacttaccta taaattaaga agagtttta ttacaaattt
      961 tcactgctgc tcctctttcc cctcctttgt cttttttttc atccttttt ctcttctgtc
     1021 catcagtgca tgacgtttaa ggccacgtat agtcctagct gacgccaata ataaaaaaca
     1081 agaaaccaaa aaaaaaaaac ccgaattca
//
```

FIGURE 10 hSHIP cDNA Sequence

5' UNTRANSLATED REGION (1-128)

```
   1 GAATTCGCGG CCGCCTCGAC CCAAGAGGCA ACGGGCGGCA GGTTGCAGTG
  51 GAGGGGCCTC CGCTCCCCTC GGTGGTGTGT GGGTCCTGGG GGTGCCTGCC
 101 GGCCCAGCCG AGGAGGCCCA CGCCCACCAT GGTCCCCTGC TGGAACCATG   START CODON
 151 GCAACATCAC CCGCTCCAAG GCGGAGGAGC TGCTTTGCAG GACAGGCAAG
 201 GACGGGAGCT TCCTCGTGCG TGCCAGCGAG TCCATCTTCC GGGCATACGC
 251 GCTCTGCGTG CTGTATCGGA ATTGCGTTTA TACTTACAGA ATTCTGCCCA
 301 ATGAAGATGA TAAATTCACT GTTCAGGCAT CCGAAGGCGT CTCCATGAGG
 351 TTCTTCACCA AGCTGGACCA GCTCATCGAG TTTTACAAGA AGGAAAACAT
 401 GGGGCTGGTG ACCCATCTGC AATACCCTGT GCCGCTGGAG GAAGAGGACA
 451 CAGGCGACGA CCCTGAGGAG GACACAGAAA GTGTCGTGTC TCCACCCGAG
 501 CTGCCCCCAA GAAACATCCC GCTGACTGCC AGCTCCTGTG AGGCCAAGGA
 551 GGTTCCTTTT TCAAACGAGA ATCCCCGAGC GACCGAGACC AGCCGGCCGA
 601 GCCTCTCCGA GACATTGTTC CAGCGACTGC AAAGCATGGA CACCAGTGGG
 651 CTTCCAGAAG AGCATCTTAA GGCCATCCAA GATTATTTAA GCACTCAGCT
 701 CGCCCAGGAC TCTGAATTTG TGAAGACAGG GTCCAGCAGT CTTCCTCACC
 751 TGAAGAAACT GACCACACTG CTCTGCAAGG AGCTCTATGG AGAAGTCATC
 801 CGGACCCTCC CATCCCTGGA GTCTCTGCAG AGGTTATTTG ACCAGCAGCT
 851 CTCCCCGGGC CTCCGTCCAC GTCCTCAGGT TCCTGGTGAG GCCAATCCCA
 901 TCAACATGGT GTCCAAGCTC AGCCAACTGA CAAGCCTGTT GTCATCCATT
 951 GAAGACAAGG TCAAGGCCTT GCTGCACGAG GGTCCTGAGT CTCCGCACCG
1001 GCCCTCCCTT ATCCCTCCAG TCACCTTTGA GGTGAAGGCA GAGTCTCTGG
1051 GGATTCCTCA GAAAATGCAG CTCAAAGTCG ACGTTGAGTC TGGGAAACTG
1101 ATCATTAAGA AGTCCAAGGA TGGTTCTGAG GACAAGTTCT ACAGCCACAA
1151 GAAAATCCTG CAGCTCATTA AGTCACAGAA ATTTCTGAAT AAGTTGGTGA
1201 TCTTGGTGGA AACAGAGAAG GAGAAGATCC TGCGGAAGGA ATATGTTTTT
1251 GCTCATCCA AAAAGAGAGA AGGCTTCTGC CAGCTCCTGC AGCAGATGAA
1301 GAACAAGCAC TCAGAGCAGC CGGAGCCCGA CATGATCACC ATCTTCATCG
1351 GCACCTGGAA CATGGGTAAC GCCCCCCCTC CCAAGAAGAT CACGTCCTGG
1401 TTTCTCTCCA AGGGGCAGGG AAAGACGCGG GACGACTCTG CGGACTACAT
1451 CCCCCATGAC ATTTACGTGA TCGGCACCCA AGAGGACCCC CTGAGTGAGA
1501 AGGAGTGGCT GGAGATCCTC AAACACTCCC TGCAAGAAAT CACCAGTGTG
1551 ACTTTTAAAA CAGTCGCCAT CCACACGCTC TGGAACATCC GCATCGTGGT
1601 GCTGGCCAAG CCTGAGCACG AGAACCGGAT CAGCCACATC TGTACTGACA
1651 ACGTGAAGAC AGGCATTGCA AACACACTGG GGAACAAGGG AGCCGTGGGG
1701 GTGTCGTTCA TGTTCAATGG AACCTCCTTA GGGTTCGTCA ACAGCCACTT
1751 GACTTCAGGA AGTGAAAAGA AACTCAGGCG AAACCAAAAC TATATGAACA
1801 TTCTCCGGTT CCTGGCCCTG GGCGACAAGA AGCTGAGTCC CTTTAACATC
1851 ACTCACCGCT TCACGCACCT CTTCTGGTTT GGGGATCTTA ACTACCGTGT
1901 GGATCTGCCT ACCTGGGAGG CAGAAACCAT CATCCAAAAA ATCAAGCAGC
1951 AGCAGTACGC AGACCTCCTG TCCCACGACC AGCTGCTCAC AGAGAGGAGG
2001 GAGCAGAAGG TCTTCCTACA CTTCGAGGAG GAAGAAATCA CGTTTGCCCC
2051 AACCTACCGT TTTGAGAGAC TGACTCGGGA CAAATACGCC TACACCAAGC
2101 AGAAAGCGAC AGGGATGAAG TACAACTTGC CTTCCTGGTG TGACCGAGTC
2151 CTCTGGAAGT CTTATCCCCT GGTGCACGTG GTGTGTCAGT CTTATGGCAG
2201 TACCAGCGAC ATCATGACGA GTGACCACAG CCCTGTCTTT GCCACATTTG
2251 AGGCAGGAGT CACTTCCCAG TTTGTCTCCA AGAACGGTCC CGGGACTGTT
2301 GACAGCCAAG GACAGATTGA GTTTCTCAGG TGCTATGCCA CATTGAAGAC
2351 CAAGTCCCAG ACCAAATTCT ACCTGGAGTT CCACTCGAGC TGCTTGGAGA
2401 GTTTTGTCAA GAGTCAGGAA GGAGAAAATG AAGAAGGAAG TGAGGGGGAG
2451 CTGGTGGTGA AGTTTGGTGA GACTCTTCCA AAGCTGAAGC CCATTATCTC
2501 TGACCCTGAG TACCTGCTAG ACCAGCACAT CCTCATCAGC ATCAAGTCCT
2551 CTGACAGCGA CGAATCCTAT GGCGAGGGCT GCATTGCCCT TCGGTTAGAG
2601 GCCACAGAAA CGCAGCTGCC CATCTACACG CCTCTCACCC ACCATGGGGA
2651 GTTGACAGGC CACTTCCAGG GGGAGATCAA GCTGCAGACC TCTCAGGGCA
2701 AGACGAGGGA GAAGCTCTAT GACTTTGTGA AGACGGAGCG TGATGAATCC
2751 AGTGGGCCAA AGACCCTGAA GAGCCTCACC AGCCACGACC CCATGAAGCA
2801 GTGGGAAGTC ACTAGCAGGG CCCCTCCGTG CAGTGGCTCC AGCATCACTG
2851 AAATCATCAA CCCCAACTAC ATGGAGTGG GGCCCTTTGG GCCACCAATG
2901 CCCCTGCACG TGAAGCAGA CTTGTCCCCT GACCAGCAGC CCACAGCCTG
2951 GAGCTACGAC CAGCCGCCCA AGGACTCCCC GCTGGGGCCC TGCAGGGGAG
3001 AAAGTCCTCC GACACCTCCC GGCCAGCCGC CCATATCACC CAAGAAGTTT
```

FIGURE 10 CONT'D

```
3051  TTACCCTCAA  CAGCAAACCG  GGGTCTCCCT  CCCAGGACAC  AGGAGTCAAG
3101  GCCCAGTGAC  CTGGGGAAGA  ACGCAGGGGA  CACGCTGCCT  CAGGAGGACC
3151  TGCCGCTGAC  GAAGCCCGAG  ATGTTTGAGA  ACCCCCTGTA  TGGGTCCCTG
3201  AGTTCCTTCC  CTAAGCCTGC  TCCCAGGAAG  GACCAGGAAT  CCCCCAAAAT
3251  GCCGCGGAAG  GAACCCCCGC  CCTGCCCGGA  ACCCGGCATC  TTGTCGCCCA
3301  GCATCGTGCT  CACCAAAGCC  CAGGAGGCTG  ATCGCGGCGA  GGGGCCCGGC
3351  AAGCAGGTGC  CCGCGCCCG   GCTGCGCTCC  TTCACGTGCT  CATCCTCTGC
3401  CGAGGGCAGG  GCGGCCGGCG  GGGACAAGAG  CCAAGGGAAG  CCCAAGACCC
3451  CGGTCAGCTC  CCAGGCCCCG  GTGCCGGCCA  AGAGGCCCAT  CAAGCCTTCC
3501  AGATCGGAAA  TCAACCAGCA  GACCCCGCCC  ACCCCGACGC  CGCGGCCGCC
3551  GCTGCCAGTC  AAGAGCCCGG  CGGTGCTGCA  CCTCCAGCAC  TCCAAGGGCC
3601  GCGACTACCG  CGACAACACC  GAGCTCCCGC  ATCACGGCAA  GCACCGGCCG
3651  GAGGAGGGGC  CACCAGGGCC  TCTAGGCAGG  ACTGCCATGC  AGTGAAGCCC   STOP CODON
3701  TCAGTGAGCT  GCCACTGAGT  CGGGAGCCCA  GAGGAACGGC  GTGAAGCCAC
3751  TGGACCCTCT  CCCGGGACCT  CCTGCTGGCT  CCTCCTGCCC  AGCTTCCTAT
3801  GCAAGGCTTT  GTGTTTTCAG  GAAAGGGCCT  AGCTTCTGTG  TGGCCCACAG
3851  AGTTCACTGC  CTGTGAGGCT  TAGCACCAAG  TGCTGAGGCT  GGAAGAAAAA
3901  CGCACACCAG  ACGGGCAACA  AACAGTCTGG  GTCCCCAGCT  CGCTCTTGGT
3951  ACTTGGGACC  CCAGTGCCTC  GTTGAGGGCG  CCATTCTGAA  GAAAGGAACT
4001  GCAGCGCCGA  TTTGAGGGTG  GAGATATAGA  TAATAATAAT  ATTAATAATA
4051  ATAATGGCCA  CATGGATCGA  ACACTCATGA  TGTGCCAAGT  GCTGTGCTAA
4101  GTGCTTTACG  AACATTCGTC  ATATCAGGAT  GACCTCGAGA  GCTGAGGCTC
4151  TAGCCACCTA  AAACACGTGC  CCAAACCCAC  CAGTTTAAAA  CGGTGTGTGT
4201  TCGGAGGGGT  GAAAGCATTA  AGAAGCCCAG  TGCCCTCCTG  GAGTGAGACA
4251  AGGGCTCGGC  CTTAAGGAGC  TGAAGAGTCT  GGGTAGCTTG  TTTAGGGTAC
4301  AAGAAGCCTG  TTCTGTCCAG  CTTCAGTGAC  ACAAGCTGCT  TTAGCTAAAG
4351  TCCCGCGGGT  TCCGGCATGG  CTAGGCTGAG  AGCAGGGATC  TACCTGGCTT
4401  CTCAGTTCTT  TGGTTGGAAG  GAGCAGGAAA  TCAGCTCCTA  TTCTCCAGTG
4451  GAGAGATCTG  GCCTCAGCTT  GGGCTAGAGA  TGCCAAGGCC  TGTGCCAGGT
4501  TCCCTGTGCC  CTCCTCGAGG  TGGGCAGCCA  TCACCAGCCA  CAGTTAAGCC
4551  AAGCCCCCCA  ACATGTATTC  CATCGTGCTG  GTAGAAGAGT  CTTTGCTGTT
4601  GCTCCCGAAA  GCCGTGCTCT  CCAGCCTGGC  TGCCAGGGAG  GGTGGGCCTC
4651  TTGGTTCCAG  GCTCTTGAAA  TAGTGCAGCC  TTTTCTTCCT  ATCTCTGTGG
4701  CTTTCAGCTC  TGCTTCCTTG  GTTATTAGGA  GAATAGATGG  GTGATGTCTT
4751  TCCTTATGTT  GCTTTTTCAA  CATAGCAGAA  TTAATGTAGG  GAGCTAAATC
4801  CAGTGGTGTG  TGTGAATGCA  GAAGGGAATG  CACCCCACAT  TCCCATGATG
4851  GAAGTCTGCG  TAACCAATAA  ATTGTGCCTT  TCTTAAAAAT  TCGCGGCCGC
4901  GTCGACGTCG  ACGCGGCCGC  GAATTC
```

5' UNTRANSLATED REGION (3695-4925)

FIGURE 11 hSHIP Amino Acid Sequence

```
   1  MVPCWNHGNI  TRSKAEELLC  RTGKDGSPLV  RASESIFRAY  ALCVLYRNCV
  51  YTYRILPNED  DKFTVQASEG  VSMRFFTKLD  QLIEFYKKEN  MGLVTHLQYP
 101  VPLEEEDTGD  DPEEDTESVV  SPPELPPRNI  PLTASSCEAK  EVPFSNENPR
 151  ATETSRPSLS  ETLFQRLQSM  DTSGLPEEHL  KAIQDYLSTQ  LAQDSEFVKT
 201  GSSSLPHLKK  LTTLLCKELY  GEVIRTLPSL  ESLQRLFDQQ  LSPGLRPRPQ
 251  VPGEANPINM  VSKLSQLTSL  LSSIEDKVKA  LLHEGPESPH  RPSLIPPVTF
 301  EVKAESLGIP  QKMQLKVDVE  SGKLIIKKSK  DGSEDKFYSH  KKILQLIKSQ
 351  KFLNKLVILV  ETEKEKILRK  EYVFADSKKR  EGFCQLLQQM  KNKHSEQPEP
 401  DMITIFIGTW  NMGNAPPPKK  ITSWFLSKGQ  GKTRDDSADY  IPHDIYVIGT
 451  QEDPLSEKEW  LEILKHSLQE  ITSVTFKTVA  IHTLWNIRIV  VLAKPEHENR
 501  ISHICTDNVK  TGIANTLGNK  GAVGVSFMFN  GTSLGFVNSH  LTSGSEKKLR
 551  RNQNYMNILR  FLALGDKKLS  PFNITHRFTH  LFWFGDLNYR  VDLPTWEAET
 601  IIQKIKQQQY  ADLLSHDQLL  TERREQKVFL  HFEEEEITFA  PTYRFERLTR
 651  DKYAYTKQKA  TGMKYNLPSW  CDRVLWKSYP  LVHVVCQSYG  STSDIMTSDH
 701  SPVFATFEAG  VTSQFVSKNG  PGTVDSQGQI  EFLRCYATLK  TKSQTKFYLE
 751  FHSSCLESFV  KSQEGENEEG  SEGELVVKFG  ETLPKLKPII  SDPEYLLDQH
 801  ILISIKSSDS  DESYGEGCIA  LRLEATETQL  PIYTPLTHHG  ELTGHFQGEI
 851  KLQTSQGKTR  EKLYDFVKTE  RDESSGPKTL  KSLTSHDPMK  QWEVTSRAPP
 901  CSGSSITEII  NPNYMGVGPF  GPPMPLHVKQ  TLSPDQQPTA  WSYDQPPKDS
 951  PLGPCRGESP  PTPPGQPPIS  PKKFLPSTAN  RGLPPRTQES  RPSDLGKNAG
1001  DTLPQEDLPL  TKPEMFENPL  YGSLSSFPKP  APRKDQESPK  MPRKEPPPCP
1051  EPGILSPSIV  LTKAQEADRG  EGPGKQVPAP  RLRSFTCSSS  AEGRAAGGDK
1101  SQGKPKTPVS  SQAPVPAKRP  IKPSRSEINQ  QTPPTPTPRP  PLPVKSPAVL
1151  HLQHSKGRDY  RDNTELPHHG  KHRPEEGPPG  PLGRTAMQ
```

FIGURE 12

```
(Peptide) FASTA of: hshipcom.pep from: 1 to: 1188 April 3, 1996 13:17

TRANSLATE of: hshipcom.con check: 8429 from: 129 to: 3693
generated symbols 1 to: 1188.

TO: 145com.pep Sequences:          1 Symbols:       1,303 Word Size: 2
Scoring matrix: GenRunData:fastapep.cmp
Variable pamfactor used
Gap creation penalty: 12.0      Gap extension penalty: 4.0

The best scores are:                                  initl initn opt..

/gcg/users/patty/145com.pep TRANSLATE of: 145com.con che...4283 4937 5189 hshipcom.pep
/gcg/users/patty/145com.pep

TRANSLATE of: 145com.con check: 4805 from: 130 to: 4040
generated symbols 1 to: 1303.

SCORES         Initl: 4283 Initn: 4937 Opt: 5189
         87.2% identity in 1194 aa overlap 10        20        30        40        50
hshipc    MVPCWNHGNITRSKAEELLCRTGKDGSFLVRASESIFRAYALCVLYRNCVYTYRILP
          |||  |||||||||||||||:|:|||||||||||||| ||:||||:||||||||||
145com    MPAMVPGWNHGNITRSKAEELLSRAGKDGSPLVRASESIPRACALCVLPRNCVYTYRILP
                  10        20        30        40        50        60

60        70        80        90       100       110
hshipc    NEDDKFTVQASEGVSMRFFTKLDQLIEFYKKENMGLVTHLQYPVPLEEEDTGDDPEEDTE
          ||||||||||||||:|||||||||||||:|||||||||||||||||||||:  |::|||| 
145com    NEDDKFTVQASEGVPMRFFTKLDQLIDFYKKENMGLVTHLQYPVPLEEEDAIDEAEEDTE
                  70        80        90       100       110       120

120       130       140       150       160       170
hshipc    SVVSPPELPPRNIPLTASSCEAKEVPFSNENPRATETSRPSLSETLFQRLQSMDTSGLPE
          ||:|||||||||||:::|:::|||::|:::||||||:|::| |||||||||||||||||
145com    SVMSPPELPPRNIPMSAGPSEAKDLPLATENPRAPEVTRLSLSETLFQRLQSMDTSGLPE
                  130       140       150       160       170       180

180       190       200       210       220       230
hshipc    EHLKAIQDYLSTQLAQDSEFVKTGSSSLPHLKKLTTLLCKELYGEVIRTLPSLESLQRLF
          |||||||||||||| ||:|:|||||:|||||||| :||||||:|||||||||||||||||
145com    EHLKAIQDYLSTQLLLDSDFLKTGSSNLPHLKKLMSLLCKELHGEVIRTLPSLESLQRLF
                  190       200       210       220       230       240

240       250       260       270       280       290
hshipc    DQQLSPGLRPRPQVPGEANPINMVSKLSQLTSLLSSIEDKVKALLHEGPESPHRPSLIPP
          |||||||||||||||||||:||:||:|||||||||||||||||:|||||:||::|:|||||
145com    DQQLSPGLRPRPQVPGEASPITMVAKLSQLTSLLSSIEDKVKSLLHEGSESTNRRSLIPP
                  250       260       270       280       290       300

300       310       320       330       340       350
hshipc    VTFEVKAESLGIPQKMQLKVDVESGKLIIKKSKDGSEDKFYSHKKILQLIKSQKFLNKLV
```

FIGURE 12 CONT'D

```
          |||||| :||||||||||:||||||||||:||||||||||||||||||||||||||||
145com    VTFEVKSESLGIPQKMHLKVDVESGKLIVKKSKDGSEDKFYSHKKILQLIKSQKFLNKLV
             310       320       330       340       350       360

360       370       380       390       400       410
hshipc    ILVETEKEKILRKEYVPADSKKREGFCQLLQQMKNKHSEQPEPDMITIFIGTWNMGNAPP
          ||||||||||||||||||||||||||||||||||||||||||||||||||||||||||||
145com    ILVETEKEKILRKEYVPADSKKREGFCQLLQQMKNKHSEQPEPDMITIFIGTWNMGNAPP
             370       380       390       400       410       420

420       430       440       450       460       470
hshipc    PKKITSWFLSKGQGKTRDDSADYIPHDIYVIGTQEDPLSEKEWLEILKHSLQEITSVTFK
          ||||||||||||||||||||||||||||||||||||||||:||||||:|:|||||:||:|||
145com    PKKITSWFLSKGQGKTRDDSADYIPHDIYVIGTQEDPLGEKEWLELLRHSLQEVTSMTPK
             430       440       450       460       470       480

480       490       500       510       520       530
hshipc    TVAIHTLWNIRIVVLAKPEHENRISHICTDNVKTGIANTLGNKGAVGVSFMFNGTSLGFV
          ||||||||||||||||||||||||||||||||||||||||||||||||||||||||||||
145com    TVAIHTLWNIRIVVLAKPEHENRISHICTDNVKTGIANTLGNKGAVGVSFMFNGTSLGFV
             490       500       510       520       530       540

540       550       560       570       580       590
hshipc    NSHLTSGSEKKLRRNQNYMNILRFLALGDKKLSPFNITHRFTHLFWFGDLNYRVDLPTWE
          |||||||||||||||||||||||||||||||||||||||||||:||||||:|||||
145com    NSHLTSGSEKKLRRNQNYMNILRFLALGDKKLSPFNITHRFTHLFWLGDLNYRVELPTWE
             550       560       570       580       590       600

600       610       620       630       640       650
hshipc    AETIIQKIKQQQYADLLSHDQLLTERREQKVFLHFEEEEITFAPTYRFERLTRDKYAYTK
          ||:||||||||||:|||:||||| ||::||||||||||||||||||||||||||||||||
145com    AEAIIQKIKQQQYSDLLAHDQLLLERKDQKVFLHFEEEEITFAPTYRFERLTRDKYAYTK
             610       620       630       640       650       660

660       670       680       690       700       710
hshipc    QKATGMKYNLPSWCDRVLWKSYPLVHVVCQSYGSTSDIMTSDHSPVFATFEAGVTSQFVS
          ||||||||||||||||||||||||||||||||||||||||||||||||||||||||||||
145com    QKATGMKYNLPSWCDRVLWKSYPLVHVVCQSYGSTSDIMTSDHSPVFATFEAGVTSQFVS
             670       680       690       700       710       720

720       730       740       750       760      .770'
hshipc    KNGPGTVDSQGQIEFLRCYATLKTKSQTKFYLEFHSSCLESFVKSQEGENEEGSEGELVV
          .||||||||||||||| |||||||||||||||||||||||||||||||||||||||||||
145com    KNGPGTVDSQGQIEFLACYATLKTKSQTKFYLEFHSSCLESFVKSQEGENEEGSEGELVV
             730       740       750       760       770       780

780       790       800       810       820       830
hshipc    KFGETLPKLKPIISDPEYLLDQHILISIKSSDSDESYGEGCIALRLEATETQLPIYTPLT
          :|||||||||||||||||||||||||||||||||||||||||||||||||:||:|  ||||||||
145com    RPGETLPKLKPIISDPEYLLDQHILISIKSSDSDESYGEGCIALRLETTEAQHPIYTPLT
             790       800       810       820       830       840

840       850       860       870       880       890
hshipc    HHGELTGHPQGEIKLQTSQGKTREKLYDPVKTERDESSGPKTLKSLTSHDPMKQWEVTSR
          ||||:|||||:|||||||||||  |||||||||||||||||||| | ||:|||||||:|||  ::|
145com    HHGEMTGHFRGEIKLQTSQGKMREKLYDPVKTERDESSGMKCLKNLTSHDPMRQWEPSGR
             850       860       870       880       890       900

900       910       920       930       940       950
hshipc    APPCSGSSITEIINPNYMGVGPFGPPMPLHVKQTLSPDQQPTAWSYDQPPKDSPLGPCRG
```

FIGURE 12 CONT'D

```
              :|:|:  ||::|:|||||:|:|||:   ||| | |||||||| |||||||  ||||:||| ||
145com  VPACGVSSLNEMINPNYIGMGPPGQ--PLHGKSTLSPDQQLTAWSYDQLPKDSSLGPGRG
              910       920       930       940       950

960       970       980       990      1000      1010
hshipc  ESPPTPPGQPPISPKKFLPSTANRGLPPRTQESRPSDLGKNAGDTLPQEDLPLTKPEMPE
        |:|||||:|||:||||||  :||:|||   ||:||:||:||||    ::| ||||  ||||||||
145com  EGPPTPPSQPPLSPKKFSSSTTNRGPCPRVQEARPGDLGK--VEALLQEDLLLTKPEMPE
             960       970       980       990       1000     1010

1020      1030      1040      1050      1060      1070
hshipc  NPLYGSLSSPPKPAPRKDQESPKMPRKEPPPCPEPGILSPSIVLTKAQEADRGEGPGKQV
        ||||||:||||| :|||:||||||  ||||||||:|||  ||||||:||||::: :|::||:
145com  NPLYGSVSSPPKLVPRKEQESPKMLRKEPPPCPDPGISSPSIVLPKAQEVESVKGTSKQA
            1020      1030      1040      1050      1060      1070

1080      1090      1100      1110      1120      1130
hshipc  ------PAPRLRSFTCSSSAEGRAAGGDKSQGKPKTPVSSQAPVPAKRPIKPSRSEINQQ
              |:||:|||||||||||  ::|||||||:::|||||||:|||:||||||::||
145com  PVPVLGPTPRIRSFTCSSSAEGRMTSGDKSQGKPKASASSQAPVPVKRPVKPSRSEMSQQ
              1080      1090      1100      1110      1120      1130

1140      1150      1160      1170      1180
hshipc  TPPTPTPRPPLPVKSPAVLHLQHSKGRDYRDNTELPHHGKHRPEEGPPGPLGRTAMQ
        |:|:|:|||||||||||||:|||||||||||||||||||||||:||  | ||||||||
145com  TTPIPAPRPPLPVKSPAVLQLQHSKGRDYRDNTELPHHGKHRQEE---GLLGRTAMQXAA
            1140      1150      1160      1170      1180      1190

145com  GDRSLEEQHKADLRPLSGCLSQDASWRTSCXLPLPSPKSQAVYFFSGNGLTSLWSKKCAA
            1200      1210      1220      1230      1240      1250
```

```
! CPU time used:
!       Database scan:    0:00:00.6
! Post-scan processing:   0:00:00.5
!         Total CPU time: 0:00:01.3
! Output File: b.
```

FIGURE 13

(Nucleotide) FASTA of: hshipcom.con from: 20 to: 4896  April 3, 1996 13:08

TO: 145com.con Sequences:       1  Symbols:    4,040  Word Size: 6
Scoring matrix: GenRunData:fastadna.cmp
Constant pamfactor used
Gap creation penalty: 12.0     Gap extension penalty: 4.0

The best scores are:                                  init1 initn opt..

/gcg/users/patty/145com.con                           8658  10037 10667 hshipcom.con
/gcg/users/patty/145com.con

SCORES        Init1: 8658 Initn: 10037 Opt: 10667
              81.6% identity in 4019 bp overlap

```
                        20         30         40         50
hshipc                  CCCAAGAGGCAACGGGCGGCAGGTTGCAG--TGG
                        |||||||||| ||||||||| |||  | |
145com  CCCTGGTAGGAGCAGCAGAGGCAATTTCTGAGAGGCAACAGGCGGCAGGTCTCAGCCTAG
            10         20         30         40         50         60

60         70         80         90        100        110
hshipc  AGGGGCCTCCGCTC-CCCTCGGTGGTGTGTGGGTCCTGGGGGTGCCTGCCGGCCCAGCCG
        || ||  |   |    |  |   ||| ||||  ||||||||| |||  |||||| | |
145com  AGAGGGCCCTGAACTACTTTGCTGGAGTGTCCGTCCTGGGAGTGGCTGCTGACCCAGTCC
            70         80         90        100        110        120

120        130        140        150        160        170
hshipc  AGGAGGCCCACGCCCACCATGGTCCCCTGCTGGAACCATGGCAACATCACCCGCTCCAAG
        ||||| ||||  ||||||||||||||  | ||||||||||||||||||||||||||||||
145com  AGGAGACCCATGCCTGCCATGGTCCCTGGGTGGAACCATGGCAACATCACCCGCTCCAAG
            130        140        150        160        170        180

180        190        200        210        220        230
hshipc  GCGGAGGAGCTGCTTTGCAGGACAGGCAAGGACGGGAGCTTCCTCGTGCGTGCCAGCGAG
        || ||||||||| ||||| ||| | |||||||||||||||||| ||||||||||||||||
145com  GCAGAGGAGCTACTTTCCAGAGCCGGCAAGGACGGGAGCTTCCTTGTGCGTGCCAGCGAG
            190        200        210        220        230        240

240        250        260        270        280        290
hshipc  TCCATCTTCCGGGCATACGCGCTCTGCGTGCTGTATCGGAATTGCGTTTATACTTACAGA
        ||||||  ||||||  || ||||||||||||||| |||||||| ||||| |||||||| |
145com  TCCATCCCCCGGGCCTGCGCACTCTGCGTGCTGTTCCGGAATTGTGTTTACACTTACAGG
            250        260        270        280        290        300

300        310        320        330        340        350
hshipc  ATTCTGCCCAATGAAGATGATAAATTCACTGTTCAGGCATCCGAAGGCGTCTCCATGAGG
        |||||||||||||||| | ||||||||||||||||||||||||||||  ||| |||||||
145com  ATTCTGCCCAATGAGGACGATAAATTCACTGTTCAGGCATCCGAAGGTGTCCCCATGAGG
            310        320        330        340        350        360
```

FIGURE 13 CONT'D

```
               360        370        380        390        400        410
hshipc  TTCTTCACCAAGCTGGACCAGCTCATCGAGTTTTACAAGAAGGAAAACATGGGGCTGGTG
        |||||||  ||||||||||||||||||||| |||||||||||||||||||||||||||||
145com  TTCTTCACGAAGCTGGACCAGCTCATCGACTTTTACAAGAAGGAAAACATGGGGCTGGTG
               370        380        390        400        410        420

420        430        440        450        460        470
hshipc  ACCCATCTGCAATACCCTGTGCCGCTGGAGGAAGAGGACACAGGCGACGACCCTGAGGAG
        |||||  |||||  |||||  |||||  ||||||||||  ||||| | || ||||||||
145com  ACCCACCTGCAGTACCCCGTGCCCCTGGAGGAGGAGGATGCTATTGATGAGGCTGAGGAG
               430        440        450        460        470        480

480        490        500        510        520        530
hshipc  GACACAGAAAGTGTCGTGTCTCCACCCGAGCTGCCCCCAAGAAACATCCCGCTGACTGCC
        ||||| |||||||||| ||||| |||||||||||  ||||||||||| ||  || |||||
145com  GACACTGAAAGTGTCATGTCACCACCTGAGCTGCCTCCCAGAAACATTCCTATGTCTGCC
               490        500        510        520        530        540

540        550        560        570        580        590
hshipc  AGCTCCTGTGAGGCCAAGGAGGTTCCTTTTTCAAACGAGAATCCCCGAGCGACCGAGACC
         | || | ||||||||||||  ||||| ||  |||  |||||| |||||| |  ||| |
145com  GGGCCCAGCGAGGCCAAGGACCTTCCTCTTGCAACAGAGAACCCCCGAGCCCCTGAGGTC
               550        560        570        580        590        600

600        610        620        630        640        650
hshipc  AGCCGGCCGAGCCTCTCCGAGACATTGTTCCAGCGACTGCAAAGCATGGACACCAGTGGG
        | |||||  ||| |||||||||||| ||||| || ||  || ||||||||| ||||||||
145com  ACCCGGCTGAGTCTCTCCGAGACACTGTTTCAGCGTCTACAGAGCATGGATACCAGTGGG
               610        620        630        640        650        660

660        670        680        690        700        710
hshipc  CTTCCAGAAGAGCATCTTAAGGCCATCCAAGATTATTTAAGCACTCAGCTCGCCCAGGAC
        ||||| || |||||| ||  ||||||||||| ||||| | ||||||||||||  || |||
145com  CTTCCCGAGGAGCACCTGAAAGCCATCCAGGATTATCTGAGCACTCAGCTCCTCCTGGAT
               670        680        690        700        710        720

720        730        740        750        760        770
hshipc  TCTGAATTTGTGAAGACAGGGTCCAGCAGTCTTCCTCACCTGAAGAAACTGACCACACTG
        || || ||| |||| ||  || ||||||||  ||| |||||||||||||  |||  |||||
145com  TCCGACTTTTTGAAAACGGGCTCCAGCAACCTCCCTCACCTGAAGAAGCTGATGTCACTG
               730        740        750        760        770        780

780        790        800        810        820        830
hshipc  CTCTGCAAGGAGCTCTATGGAGAAGTCATCCGGACCCTCCCATCCCTGGAGTCTCTGCAG
        ||||||||||||||| ||||| |||||||||| ||||| ||||||||||||||||||||
145com  CTCTGCAAGGAGCTCCATGGGGAAGTCATCAGGACTCTGCCATCCCTGGAGTCTCTGCAG
               790        800        810        820        830        840

840        850        860        870        880        890
hshipc  AGGTTATTTGACCAGCAGCTCTCCCCGGGCCTCCGTCCACGTCCTCAGGTTCCTGGTGAG
        ||||| ||||||||| |||||||||| ||||| || ||||| ||||||||  || || |
145com  AGGTTGTTTGACCAACAGCTCTCCCCAGGCCTTCGCCCACGACCTCAGGTGCCCGGAGAG
               850        860        870        880        890        900

900        910        920        930        940        950
hshipc  GCCAATCCCATCAACATGGTGTCCAAGCTCAGCCAACTGACAAGCCTGTTGTCATCCATT
        ||||  |||||||| |||||  ||||||||||||||  |||||||| || |||| |||||
145com  GCCAGTCCCATCACCATGGTTGCCAAACTCAGCCAATTGACAAGTCTGCTGTCTTCCATT
               910        920        930        940        950        960
```

FIGURE 13 CONT'D

```
              960        970        980        990        1000       1010
hshipc  GAAGACAAGGTCAAGGCCTTGCTGCACGAGGGTCCTGAGTCTCCGCACCGGCCCTCCCTT
        |||||  |||||||||| |||||||||||||||| | || ||| |  || ||| ||||||
145com  GAAGATAAGGTCAAGTCCTTGCTGCACGAGGGCTCAGAATCTACCAACAGGCGTTCCCTT
              970        980        990        1000       1010       1020

1020       1030       1040       1050       1060       1070
hshipc  ATCCCTCCAGTCACCTTTGAGGTGAAGGCAGAGTCTCTGGGGATTCCTCAGAAAATGCAG
        |||||||| ||||||||||||||||||| ||||||  ||||| |||||||||||||||| 
145com  ATCCCTCCGGTCACCTTTGAGGTGAAGTCAGAGTCCCTGGGCATTCCTCAGAAAATGCAT
              1030       1040       1050       1060       1070       1080

1080       1090       1100       1110       1120       1130
hshipc  CTCAAAGTCGACGTTGAGTCTGGGAAACTGATCATTAAGAAGTCCAAGGATGGTTCTGAG
        |||||||| |||||||||||||||||||||||| ||||||||||||||||||||||||||
145com  CTCAAAGTGGACGTTGAGTCTGGGAAACTGATCGTTAAGAAGTCCAAGGATGGTTCTGAG
              1090       1100       1110       1120       1130       1140

1140       1150       1160       1170       1180       1190
hshipc  GACAAGTTCTACAGCCACAAGAAAATCCTGCAGCTCATTAAGTCACAGAAATTTCTGAAT
        |||||||||||||||||||| |||||||||||||||||||||| ||||| ||||| ||
145com  GACAAGTTCTACAGCCACAAAAAAATCCTGCAGCTCATTAAGTCCCAGAAGTTTCTAAAC
              1150       1160       1170       1180       1190       1200

1200       1210       1220       1230       1240       1250
hshipc  AAGTTGGTGATCTTGGTGGAAACAGAGAAGGAGAAGATCCTGCGGAAGGAATATGTTTTT
        |||||||||| |||||| || |||||||||||||||| ||||| ||||||||||||||||
145com  AAGTTGGTGATTTTGGTGGAGACGGAGAAGGAGAAAATCCTGAGGAAGGAATATGTTTTT
              1210       1220       1230       1240       1250       1260

1260       1270       1280       1290       1300       1310
hshipc  GCTGACTCCAAAAAGAGAGAAGGCTTCTGCCAGCTCCTGCAGCAGATGAAGAACAAGCAC
        ||||||||| || || ||||||||||||||| || ||||||||||||||||||||||||
145com  GCTGACTCTAAGAAAAGAGAAGGCTTCTGTCAACTCCTGCAGCAGATGAAGAACAAGCAT
              1270       1280       1290       1300       1310       1320

1320       1330       1340       1350       1360       1370
hshipc  TCAGAGCAGCCGGAGCCCGACATGATCACCATCTTCATCGGCACCTGGAACATGGGTAAC
        || |||||||| ||||| ||||||||||||||||||||| |||| |||||||||||||| 
145com  TCGGAGCAGCCAGAGCCTGACATGATCACCATCTTCATTGGCACTTGGAACATGGGTAAT
              1330       1340       1350       1360       1370       1380

1380       1390       1400       1410       1420       1430
hshipc  GCCCCCCCTCCCAAGAAGATCACGTCCTGGTTTCTCTCCAAGGGGCAGGGAAAGACGCGG
        || |||||||||||||||||||||||||||||||||||||||||||||||||||| |||
145com  GCACCCCCTCCCAAGAAGATCACGTCCTGGTTTCTCTCCAAGGGGCAGGGAAAGACACGG
              1390       1400       1410       1420       1430       1440

1440       1450       1460       1470       1480       1490
hshipc  GACGACTCTGCGGACTACATCCCCCATGACATTTACGTGATCGGCACCCAAGAGGACCCC
        |||||||||| ||||||||||||||||||| ||||| |||||| ||||| ||||| |||
145com  GACGACTCTGCTGACTACATCCCCCATGACATCTATGTGATTGGCACCCAGGAGGATCCC
              1450       1460       1470       1480       1490       1500

1500       1510       1520       1530       1540       1550
hshipc  CTGAGTGAGAAGGAGTGGCTGGAGATCCTCAAACACTCCCTGCAAGAAATCACCAGTGTG
        ||  | |||||||||||||||||| |||| |||| ||||||||||||| |||||||| ||
145com  CTTGGAGAGAAGGAGTGGCTGGAGCTACTCAGGCACTCCCTGCAAGAAGTCACCAGCATG
              1510       1520       1530       1540       1550       1560
```

FIGURE 13 CONT'D

```
              1560      1570      1580      1590      1600      1610
hshipc  ACTTTTAAAACAGTCGCCATCCACACGCTCTGGAACATCCGCATCGTGGTGCTGGCCAAG
        ||  ||||||||||| ||||||||||| ||||||||||| ||||| |||||||| ||||||
145com  ACATTTAAAACAGTTGCCATCCACACCCTCTGGAACATTCGCATAGTGGTGCTTGCCAAG
              1570      1580      1590      1600      1610      1620

1620      1630      1640      1650      1660      1670
hshipc  CCTGAGCACGAGAACCGGATCAGCCACATCTGTACTGACAACGTGAAGACAGGCATTGCA
        ||  ||||| ||||| |||||||||||  |||| |||||||||||||||||||||| ||
145com  CCAGAGCATGAGAATCGGATCAGCCATATCTGCACTGACAACGTGAAGACAGGCATCGCC
              1630      1640      1650      1660      1670      1680

1680      1690      1700      1710      1720      1730
hshipc  AACACACTGGGGAACAAGGGAGCCGTGGGGGTGTCGTTCATGTTCAATGGAACCTCCTTA
        |||||  ||||| ||||||||||| ||||| |||| |||||||||||||||||||||||
145com  AACACCCTGGGAAACAAGGGAGCAGTGGGAGTGTCCTTCATGTTCAATGGAACCTCCTTG
              1690      1700      1710      1720      1730      1740

1740      1750      1760      1770      1780      1790
hshipc  GGGTTCGTCAACAGCCACTTGACTTCAGGAAGTGAAAAGAAACTCAGGCGAAACCAAAAC
        |||||||||||||||||||||||||| |||||||||||||| |||||| |||| ||||||
145com  GGGTTCGTCAACAGCCACTTGACTTCTGGAAGTGAAAAAAAGCTCAGGAGAAATCAAAAC
              1750      1760      1770      1780      1790      1800

1800      1810      1820      1830      1840      1850
hshipc  TATATGAACATTCTCCGGTTCCTGGCCCTGGGCGACAAGAAGCTGAGTCCCTTTAACATC
        |||||||||| || |||||||||||||||||| ||||||||||||| || ||||||||||
145com  TATATGAACATCCTGCGGTTCCTGGCCCTGGGAGACAAGAAGCTAAGCCCATTTAACATC
              1810      1820      1830      1840      1850      1860

1860      1870      1880      1890      1900      1910
hshipc  ACTCACCGCTTCACGCACCTCTTCTGGTTTGGGGATCTTAACTACCGTGTGGATCTGCCT
        ||  |||||||||| | ||||||||||| ||||||||| ||||||||| || ||  ||||
145com  ACCCACCGCTTCACCCACCTCTTCTGGCTTGGGGATCTCAACTACCGCGTGGAGCTGCCC
              1870      1880      1890      1900      1910      1920

1920      1930      1940      1950      1960      1970
hshipc  ACCTGGGAGGCAGAAACCATCATCCAAAAAATCAAGCAGCAGCAGTACGCAGACCTCCTG
        || ||||||||| |  |||||||||| ||||||||||| |||||||| ||||||  |||
145com  ACTTGGGAGGCAGAGGCCATCATCCAGAAGATCAAGCAACAGCAGTATTCAGACCTTCTG
              1930      1940      1950      1960      1970      1980

1980      1990      2000      2010      2020      2030
hshipc  TCCCACGACCAGCTGCTCACAGAGAGGAGGGAGCAGAAGGTCTTCCTACACTTCGAGGAG
        |||||||||| |||||| |  |||||| ||| ||||||||||||||| | ||||||||||
145com  GCCCACGACCAACTGCTCCTGGAGAGGAAGGACCAGAAGGTCTTCCTGCACTTTGAGGAG
              1990      2000      2010      2020      2030      2040

2040      2050      2060      2070      2080      2090
hshipc  GAAGAAATCACGTTTGCCCCAACCTACCGTTTTGAGAGACTGACTCGGGACAAATACGCC
        ||||| |||||| || |||| |||| || ||||| |||||||| |||||||||| || |
145com  GAAGAGATCACCTTCGCCCCCACCTATCGATTTGAAAGACTGACCCGGGACAAGTATGCA
              2050      2060      2070      2080      2090      2100

2100      2110      2120      2130      2140      2150
hshipc  TACACCAAGCAGAAAGCGACAGGGATGAAGTACAACTTGCCTTCCTGGTGTGACCGAGTC
        |||||  |||||||||| ||||||||||||||||||||||| | |||||||| |||||||
145com  TACACGAAGCAGAAAGCAACAGGGATGAAGTACAACTTGCCGTCCTGGTGCGACCGAGTC
              2110      2120      2130      2140      2150      2160
```

FIGURE 13 CONT'D

```
                2160       2170       2180       2190       2200       2210
hshipc  CTCTGGAAGTCTTATCCCTGGTGCACGTGGTGTGTCAGTCTTATGGCAGTACCAGCGAC
        ||||||||||||| || |||||||| ||||| |||||||| ||||||||||||||| |||
145com  CTCTGGAAGTCTTACCCGCTGGTGCATGTGGTCTGTCAGTCCTATGGCAGTACCAGTGAC
                2170       2180       2190       2200       2210       2220

2220       2230       2240       2250       2260       2270
hshipc  ATCATGACGAGTGACCACAGCCCTGTCTTTGCCACATTTGAGGCAGGAGTCACTTCCCAG
        |||||||||||||||||||||||||||||||||||||||| ||||| |||||||||| |||
145com  ATCATGACGAGTGACCACAGCCCTGTCTTTGCCACGTTTGAAGCAGGAGTCACATCTCAA
                2230       2240       2250       2260       2270       2280

2280       2290       2300       2310       2320       2330
hshipc  TTTGTCTCCAAGAACGGTCCCGGGACTGTTGACAGCCAAGGACAGATTGAGTTTCTCAGG
        || ||||||||||| ||||| || |||||| || ||||||||| ||||| ||||||||
145com  TTCGTCTCCAAGAATGGTCCTGGCACTGTAGATAGCCAAGGGCAGATCGAGTTTCTTGCA
                2290       2300       2310       2320       2330       2340

2340       2350       2360       2370       2380       2390
hshipc  TGCTATGCCACATTGAAGACCAAGTCCCAGACCAAATTCTACCTGGAGTTCCACTCGAGC
        ||||| |||||| |||||||||||||||||||||||| || |||||| |||||||||||| |||
145com  TGCTACGCCACACTGAAGACCAAGTCCCAGACTAAGTTCTACTTGGAGTTCCACTCAAGC
                2350       2360       2370       2380       2390       2400

2400       2410       2420       2430       2440       2450
hshipc  TGCTTGGAGAGTTTTGTCAAGAGTCAGGAAGGAGAAAATGAAGAAGGAAGTGAGGGGGAG
        ||||| ||||||||+||||||||||||||||||||||| |||||||| |||||||| || |||
145com  TGCTTAGAGAGTTTTGTCAAGAGTCAGGAAGGAGAGAATGAAGAGGGAAGTGAAGGAGAG
                2410       2420       2430       2440       2450       2460

2460       2470       2480       2490       2500       2510
hshipc  CTGGTGGTGAAGTTTGGTGAGACTCTTCCAAAGCTGAAGCCCATTATCTCTGACCCTGAG
        ||||||||   ||||||  |||||||||| ||||| ||||||||||||||||||||| |||
145com  CTGGTGGTACGGTTTGGAGAGACTCTTCCCAAGCTAAAGCCGATTATCTCTGACCCCGAG
                2470       2480       2490       2500       2510       2520

2520       2530       2540       2550       2560       2570
hshipc  TACCTGCTAGACCAGCACATCCTCATCAGCATCAAGTCCTCTGACAGCGACGAATCCTAT
        ||| | || ||||||||| ||||| |||||||| || |||||||||||| ||||| |||||||
145com  TACTTACTGGACCAGCATATCCTGATCAGCATTAAATCCTCTGACAGTGACGAGTCCTAT
                2530       2540       2550       2560       2570       2580

2580       2590       2600       2610       2620       2630
hshipc  GGCGAGGGCTGCATTGCCCTTCGGTTAGAGGCCACAGAAACGCAGCTGCCCATCTACACG
        || || |||||||||||||||||| || ||| ||||||| | |||| || ||||||||||
145com  GGTGAAGGCTGCATTGCCCTTCGCTTGGAGACCACAGAGGCTCAGCATCCTATCTACACG
                2590       2600       2610       2620       2630       2640

2640       2650       2660       2670       2680       2690
hshipc  CCTCTCACCCACCATGGGGAGTTGACAGGCCACTTCCAGGGGGAGATCAAGCTGCAGACC
        |||||||||||||||||||| |||| |||||||||| ||| |||||| ||||||||||||
145com  CCTCTCACCCACCATGGGGAGATGACTGGCCACTTCAGGGGAGAGATTAAGCTGCAGACC
                2650       2660       2670       2680       2690       2700

2700       2710       2720       2730       2740       2750
hshipc  TCTCAGGGCAAGACGAGGGAGAAGCTCTATGACTTTGTGAAGACGGAGCGTGATGAATCC
        || |||||||||| |||||||||||||||||||||||||||||||| ||||| |||||||||
145com  TCCCAGGGCAAGATGAGGGAGAAGCTCTATGACTTTGTGAAGACAGAGCGGGATGAATCC
                2710       2720       2730       2740       2750       2760
```

FIGURE 13 CONT'D

```
            2760       2770       2780       2790       2800       2810
hshipc  AGTGGGCCAAAGACCCTGAAGAGCCTCACCAGCCACGACCCCATGAAGCAGTGGGAAGTC
        |||||  ||  | |||||||  |||||||||||| |||||  ||||  |||  |||||
145com  AGTGGAATGAAATGCTTGAAGAACCTCACCAGCCATGACCCTATGAGGCAATGGGAGCCT
            2770       2780       2790       2800       2810       2820

2820       2830       2840       2850       2860       2870
hshipc  ACTAGCAGGGCCCCTCCGTGCAGTGGCTCCAGCATCACTGAAATCATCAACCCCAACTAC
        ||  ||||||| ||||  | ||   ||| |||||||  ||| ||| || ||||| ||||||
145com  TCTGGCAGGGTCCCTGCATGTGGTGTCTCCAGCCTCAATGAGATGATCAATCCAAACTAC
            2830       2840       2850       2860       2870       2880

2880       2890       2900       2910       2920       2930
hshipc  ATGGGAGTGGGGCCCTTTGGGCCACCAATGCCCCTGCACGTGAAGCAGACCTTGTCCCCT
        ||  ||  |||||||  |||||        | |||||||||| |  |||   ||| |||||||
145com  ATTGGTATGGGGCCTTTTGG------ACAGCCCCTGCATGGGAAATCAACCCTGTCCCCA
            2890       2900              2910       2920       2930

2940       2950       2960       2970       2980      .2990
hshipc  GACCAGCAGCCCACAGCCTGGAGCTACGACCAGCCGCCCAAGGACTCCCCGCTGGGGCCC
        || |||||  | ||||||  |||||  || |||||||  |||||  ||||||| | |||||||||
145com  GATCAGCAACTCACAGCTTGGAGTTATGACCAGCTACCCAAAGACTCCTCCCTGGGGCCT
            2940       2950       2960       2970       2980       2990

3000       3010       3020       3030       3040       3050
hshipc  TGCAGGGGAGAAAGTCCTCCGACACCTCCCGGCCAGCCGCCCATATCACCCAAGAAGTTT
        | ||||||  ||  |||||||  ||  ||||||  ||| || || | ||| || ||||||||||
145com  GGGAGGGGGGAGGGTCCTCCAACCCCTCCCTCCCAACCACCTCTGTCGCCAAAGAAGTTT
            3000       3010       3020       3030       3040       3050

3060       3070       3080       3090       3100       3110
hshipc  TTACCCTCAACAGCAAACCGGGTCTCCCTCCCAGGACACAGGAGTCAAGGCCCAGTGAC
        | | | || ||| | |||||| ||||  |   |||||| || ||| |||| ||  | ||
145com  TCATCTTCCACAACCAACCGAGGTCCCTGCCCCAGGGTGCAAGAGGCAAGACCTGGGGAT
            3060       3070       3080       3090       3100       3110

3120       3130       3140       3150       3160       3170
hshipc  CTGGGGAAGAACGCAGGGGACACGCTGCCTCAGGAGGACCTGCCGCTGACGAAGCCCGAG
        ||||| |||       | ||| |  |||| ||||||||||||||| |||||||||||||||
145com  CTGGGAAAG------GTGGAAGCTCTGCTCCAGGAGGACCTGCTGCTGACGAAGCCCGAG
            3120              3130       3140       3150       3160

3180       3190       3200       3210       3220       3230
hshipc  ATGTTTGAGAACCCCCTGTATGGGTCCCTGAGTTCCTTCCCTAAGCCTGCTCCCAGGAAG
        |||||||||||||||| ||||||||| ||| |||||||||||||||||| |  |||||||||
145com  ATGTTTGAGAACCCACTGTATGGATCCGTGAGTTCCTTCCCTAAGCTGGTGCCCAGGAAA
            3170       3180       3190       3200       3210       3220

3240       3250       3260       3270       3280       3290
hshipc  GACCAGGAATCCCCCAAAATGCCGCGGAAGGAACCCCCGCCCTGCCCGGAACCCGGCATC
        || |||||| || ||||  |||| |||||||||| ||||||||| ||  || || || |||
145com  GAGCAGGAGTCTCCCAAGATGCTGCGGAAGGAGCCCCCGCCCTGTCCAGACCCAGGAATC
            3230       3240       3250       3260       3270       3280

3300       3310       3320       3330       3340       3350
hshipc  TTGTCGCCCAGCATCGTGCTCACCAAAGCCCAGGAGGCTGATCGCGGCGAGGGGCCCGGC
        |  || |||||||||||||||||  |||||||| |||||  || |  |  |||||| | | ||
145com  TCATCACCCAGCATCGTGCTCCCCAAAGCCCAAGAGGTGGAGAGTGTCAAGGGGACAAGC
            3290       3300       3310       3320       3330       3340
```

FIGURE 13 CONT'D

```
              3359        3360       3370       3380       3390
hshipc  AAGCAGG----TG--------------CCCGCGCCCCGGCTGCGCTCCTTCACGTGCTCA
        || ||||   ||              ||| | |||||| | |||||||| || || ||
145com  AAACAGGCCCCTGTGCCTGTCCTTGGCCCCACACCCCGGATCCGCTCCTTTACCTGTTCT
          3350       3360       3370       3380       3390       3400

3400       3410       3420       3430       3440       3450
hshipc  TCCTCTGCCGAGGGCAGGGCGGCCGGCGGGGACAAGAGCCAAGGGAAGCCCAAGACCCCG
        || ||||| ||||||||  | || ||||||||||||||||||||||||||||||| || |
145com  TCTTCTGCTGAGGGCAGAATGACCAGTGGGGACAAGAGCCAAGGGAAGCCCAAGGCCTCA
          3410       3420       3430       3440       3450       3460

3460       3470       3480       3490       3500       3510
hshipc  GTCAGCTCCCAGGCCCCGGTGCCGGCCAAGAGGCCCATCAAGCCTTCCAGATCGGAAATC
        | |||  |||||| ||||| | ||||||||| |||||||||| |||||||||| || |||||
145com  GCCAGTTCCCAAGCCCCAGTGCCAGTCAAGAGGCCTGTCAAGCCTTCCAGGTCAGAAATG
          3470       3480       3490       3500       3510       3520

3520       3530       3540       3550       3560       3570
hshipc  AACCAGCAGACCCCGCCCACCCCGACGCCGCGGCCGCCGCTGCCAGTCAAGAGCCCGGCG
        | |||||||||  | |||| ||| | || ||||| || |||||||||||||| || ||
145com  AGCCAGCAGACAACACCCCATCCCAGCTCCACGGCCACCCCTGCCAGTCAAGAGTCCTGCT
          3530       3540       3550       3560       3570       3580

3580       3590       3600       3610       3620       3630
hshipc  GTGCTGCACCTCCAGCACTCCAAGGGCCGCGACTACCGCGACAACACCGAGCTCCCGCAT
        || |||||  || || || |||||  ||| | |||||||||||||||||||| |||| ||
145com  GTCCTGCAGCTGCAACATTCCAAAGGCAGAGACTACCGTGACAACACAGAACTCCCCCAC
          3590       3600       3610       3620       3630       3640

3640        3650       3660       3670       3680       3690
hshipc  CACGGCAAGCACCGGCCGGAGGAGGGGCCACCAGGGCCTCTAGGCAGGACTGCCATGCAG
        || |||||||||||| | ||||||       |||| || |||||||||||||||||||||
145com  CATGGCAAGCACCGCCAAGAGGAG--------GGGCTGCTTGGCAGGACTGCCATGCAG
          3650       3660       3670            3680       3690

3700       3710       3720       3730       3740
hshipc  TGAAGCCCTCAGTGAGCTGCCACTGAGTCGGGAGCCCAGAG--GAACGGCG---------
        || |||      ||||  || | |||     ||| || ||  || | |||
145com  TG-AGCTGCTGGTGATCGGAGCCTGGAGGAACAGCACAAAGCAGACCTGCGACCTCTCTC
          3700       3710       3720       3730       3740       3750

3750       3760       3770       3780       3790
hshipc  -TGAAGCCACT----GGA-CCCTCTCCCGGGACCTCCTGCTGGCTCCTCCTGCCCAGCTT
         || ||| ||    ||| |||  |||| ||||||||||||| |||| || |||| |||||
145com  AGGATGCCTCTCTCAGGATGCCTCTTGGAGGACCTCCTGCTAGCTCTTCTTGCCTAGCTT
          3760       3770       3780       3790       3800       3810

3800       3810       3820       3830       3840       3850
hshipc  CCTATGCAAGGCTTTGTGTTTTCAGGAAAGGGCCTAGCTTCTGTGTGGCCCACAGAGTTC
        |   |  ||||||| ||| ||||     |||   || || |  | |     |  | |||  |
145com  CAAGTCCCAGGCTGTGTATTTT-TTTTCAGGAAACGGCCTCACT---TCTCTGTG-GTCC
          3820       3830       3840       3850       3860       3870

3860       3870       3880       3890       3900       3910
hshipc  ACTGCCTGTGAGGCTTAGCACCAAGTGCTGAGGCTGGAAGAAAAAC-GCACACCAGACGG
        |   ||||  |||   |||    || ||| |    |||  |   | || |||
145com  AAGAAGTGTGCTGCTGGCTGCCACACTGTGCGGCAGATGCTAAAGCTGGATGACAAACGC
          3880       3890       3900       3910       3920       3930
```

FIGURE 13 CONT'D

```
            3920       3930       3940       3950       3960       3970
hshipc  GCAACAAACAGTCTG-GGTCCCCAG--CTCGCTCTTGGTACTTGGGACCCCAGTGCCTCG
        |  ||  ||||  |  |   |  |   |  |   ||  |  |||   |  ||||  |||   ||   |  ||||
145com  ACGCCATACAGACAGCAGACAGCGGCACTGGGTCTCAGAACTT-GGATTCCTGGGCCTTC
            3940       3950       3960       3970       3980       3990

3980       3990       4000       4010       4020       4030
hshipc  TTGAGGGCGCCATTCTGAAGAAAGGAACTGCAGCGCCGATTTGAGGGTGGAGATATAGAT
         ||    |  |||| ||  |  |||||||||||
145com  TTCCAGTCGCCGTTTTAAAGAAAGGAACTAACGGAGCTGCTCATCCGA
            4000       4010       4020       4030       4040
```

```
! CPU time used:
!        Database scan:    0:00:00.8
! Post-scan processing:    0:00:01.4
!         Total CPU time:  0:00:02.4
! Output File: b.
```

SH2-CONTAINING INOSITOL-PHOSPHATASE

This application claims benefit to U.S. provisional application No. 60/006,063, filed Sep. 27, 1995 and application Ser. No. 60/007,788, filed Nov. 30, 1995 and application Ser. No. 60/015,217 filed Apr. 9, 1996.

FIELD OF THE INVENTION

The invention relates to a novel SH2-containing inositol-phosphatase, truncations, analogs, homologs and isoforms thereof; nucleic acid molecules encoding the protein and truncations, analogs, and homologs of the protein; and, uses of the protein and nucleic acid molecules.

BACKGROUND OF THE INVENTION

Many growth factors regulate the proliferative, differentiative and metabolic activities of their target cells by binding to, and activating cell surface receptors that have tyrosine kinase activity (Cantley, L. C., et al. 1991, Cell 64:281–302; and Ullrich, A., and J. Schlessinger. 1990, Cell 61:203–212). The activated receptors become tyrosine phosphorylated through intermolecular autophosphorylation events, and then stimulate intracellular signalling pathways by binding to, and phosphorylating cytoplasmic signalling proteins (Cantley, L. C., et al. 1991, Cell 64:281–302; and, Ullrich, A., and J. Schlessinger, 1990, Cell 61:203–212). Many cytoplasmic signalling proteins share a common structural motif, known as the src homology 2 (SH2) domain, that mediates their association with specific phosphotyrosine-containing sites on activated receptors (Heldin, C. H. 1991, Trends Biochem. Sci. 16:450–452; Koch, C. A., et al., 1991, Science 252:669–674; Margolis, B. 1992, Cell Growth Differ. 3:73–80; McGlade, C. J., et al, 1992, Mol. Cell. Biol. 12: 991–997; Moran, M. F., et al., 1990, Proc. Natl. Acad. Sci. USA 87:8622–8626; and Reedijk, M., et al., 1992, EMBO J. 11:1365–1372).

Two SH2-containing proteins, Grb2 and Shc, have been implicated in the Ras signalling pathway (Lowenstein, E. J.,et al., 1992, Cell 70:431–442, and, Pelicci, G., et al., 1992, Cell 70 93–104.). Grb2 and Shc act upstream of Ras and bind directly to activated receptors (Buday, L., and J. Downward, 1993, Cell 73:611–620; Matuoka, K. et al., 1993, EMBO J. 12:3467–3473, Oakley, B. R. et al., 1980, Anal. Biochem. 105:361–363., Reedijk, M., et al., 1992, EMBO J. 11:1365–1372; Rozakis-Adcock, M., et al., 1992 Nature 360: 689–692; and, Songyang, Z., et al., 1993, Cell 72:767–778), or to designated SH2 docking proteins, such as the insulin receptor substrate 1 (IRS-1), which is tyrosine phosphorylated in response to insulin (Baltensperger, K., et al., Science 260:1950–1952; Pelicci, G., et al., 1992, Cell 70:93–104; Skolnik, E. Y., 1993, EMBO J. 12:1929–1936; Skolnik, E. Y., et al., 1993, Science 260:1953–1955; and Suen, K-L., et al., 1993 Mol. Cell. Biol. 13: 5500–5512).

Grb2 is a 25 kDa adapter protein with two SH3 domains flanking one SH2 domain. It has been shown in fibroblasts to shuttle its constitutively bound Ras guanine nucleotide exchange factor, Sos1, to activated receptors (or to IRS-1 (Skolnik, E. Y., 1993, EMBO J. 12:1929–1936; and Skolnik, E. Y., et al., 1993, Science 260:1953–1955), (Baltensperger, K., et al., Science 260:1950–1952; Buday, L., and J. Downward, 1993, Cell 73:611–620; Egan, S. E. et al., 1993, Nature (London) 367:87–90; Gale, N. W., et al., 1993, Nature (London) 363:88–92; Li, N., et al., 1993, Nature (London) 363-85–88; Olivier, J. P. et al., 1993, Cell 73:179–191; and Rozakis-Adcock, M., et al., 1993 Nature (London) 363:83–85). Binding of the SH2 domain of Grb2 to tyrosine phosphorylated proteins activates Sos1 which then catalyzes the activation of Ras by exchanging GDP for GTP (Buday, L., and J. Downward. 1993. Cell 73:611–620 12,,20; Egan, S. E. Et al, 1993, Nature 363:45–51; Gale, N. W et al., 1993 Nature 363:88–92; Li, N., et al., 1993 Nature 363:85–88).

Shc is also an adapter protein that is widely expressed in all tissues. The protein contains an N-terminal phosphotyrosine binding (PTB) domain (Kavanaugh, V. M. Et al., 1995 Science, 268:1177–1179; Craparo, A., et al., 1995, J. Biol. Chem. 270:15639–15643; van der Geer, P., & Pawson, T., 1995, TIBS 20:277–280; Batzer, A. G., et al., Mol. Cell. Biol. 1995, 15:4403–4409; and Trub, T., et al., 1995, J. Biol. Chem. 270:18205–18208) and a C-terminal SH2 domain (Pelicci, G., et al., 1992. Cell 70:93–104) and can associate, in its tyrosine phosphorylated form, with Grb2-Sos1 complexes and may increase Grb2-Sos1 interactions following growth factor stimulation (Egan, S. E. Et al, 1993, Nature 363:45–51; Rozakis-Adcock, M., et al., 1992, Nature 360:689–692; and Ravichandran, K. S., 1995, Mol. Cell. Biol. 15:593–600). Shc appears to function as a bridge between Grb2-Sos1 complexes and tyrosine kinases where the latter are incapable, for lack of an appropriate consensus sequence, of binding Grb2-Sos1 directly (Egan, S. E. Et al, 1993, Nature 363:45–51).

Preliminary evidence suggests that Shc and Grb2 may be used by members of the hemopoietin receptor superfamily (Cutler, R. L., et al., 1993, J. Biol. Chem. 268:21463–21465, Damen, J. E., et al., 1993, Blood 82:2296–2303). Although members of this family lack endogenous kinase activity, following ligand binding, they are apparently tyrosine phosphorylated by a closely associated JAK family member (Argetsinger, L. S., et al., 1993, Cell 74:237–244; Lutticken, C., et al., 1994, Science 263:89–92; Silvennoinen, O., et al., 1993, Proc. Natl. Acad. Sci. USA 90:8429–8433; and Witthuhn, B. A., et al., 1993, Cell 74:227–236). The hemopoietic growth factors, erythropoietin (Ep), interleukin-3 (IL-3) and steel factor (SF) (which utilizes a receptor with endogenous tyrosine kinase activity, i.e., c-kit, (Chabot, B., et al., 1988, Nature (London) 335:88–89)), have been shown to induce the tyrosine phosphorylation of Shc and its subsequent association with Grb2 (Cutler, R. L., et al., 1993, J. Biol. Chem. 268:21463–21465). Stimulation of members of the hemopoietin receptor superfamily has also been reported to result in the association of Shc with uncharacterized proteins with molecular masses of 130 kDa (Smit, L., et al., J. of Biol. Chem. 269(32):20209, 1994), 150 kDa (Lioubin, M. N., et al., Mol. Cell. Biol. 14(9):5682, 1994), and 145 kDa (Damen, J., et al., Blood 82(8):2296, 1993, and Saxton, T. M. et al., J. Immunol. 623, 1994).

SUMMARY OF THE INVENTION

The present inventor has identified and characterized a protein that associates with Shc in response to multiple cytokines. The unique protein, herein referred to as "SH2-containing inositol-phosphatase" or "SHIP" (for SH2-containing, inositol 5-phosphatase), contains an amino terminal src homology 2 (SH2) domain, two phosphotyrosine binding (PTB) consensus sequences, a proline rich region, and two motifs highly conserved among inositol polyphosphate-5-phosphatases (phosphoIns-5-ptases). Cell lysates immunoprecipitated with antiserum to the protein exhibit phosphoIns-5-ptase activity, in particular, both phosphatidylinositol trisphosphate (PtdIns-3,4,5-P$_3$) and inositol tetraphosphate (Ins-1,3,4,5-P$_4$) 5-phosphatase activity. This activity implicates SHIP in the regulation of signalling pathways that control gene expression, cell proliferation, differentiation, activation, and metabolism, in particular, the Ras and phospholipid signalling pathways. This finding permits the identification of substances which affect SHIP and which may be used in the treatment of conditions involving perturbation of signalling pathways.

The present invention therefore provides a purified and isolated nucleic acid molecule comprising a sequence encoding an SH2-containing inositol-phosphatase which has a src homology 2 (SH2) domain and exhibits phosphoIns-5-ptase activity. The SH2-containing inositol-phosphatase is further characterized by it ability to associate with Shc and by having two phosphotyrosine binding (PTB) consensus sequences, a proline rich region, and motifs highly conserved among inositol polyphosphate-5-phosphatases (phosphoIns-5-ptases).

In an embodiment of the invention, the purified and isolated nucleic acid molecule comprises (i) a nucleic acid sequence encoding an SH2-containing inositol-phosphatase having the amino acid sequence as shown in SEQ ID NO:2 or FIG. 2(A); and, (ii) nucleic acid sequences complementary to (i). In another embodiment of the invention, the purified and isolated nucleic acid molecule comprises (i) a nucleic acid sequence encoding an SH2-containing inositol-phosphatase having the amino acid sequence as shown in SEQ ID NO:8 or FIG. 11; and, (ii) nucleic acid sequences complementary to (i).

In a preferred embodiment of the invention, the purified and isolated nucleic acid molecule comprises (i) a nucleic acid sequence encoding an SH2-containing inositol-phosphatase having the nucleic acid sequence as shown in SEQ ID NO:1 or FIG. 3, wherein T can also be U;

(ii) a nucleic acid sequence complementary to (i), preferably complementary to the full length nucleic acid sequence shown in SEQ ID NO: 1 or FIG. 3; or (iii) a nucleic acid molecule differing from any of the nucleic acids of (i) and (ii) in codon sequences due to the degeneracy of the genetic code.

In another preferred embodiment of the invention, the purified and isolated nucleic acid molecule comprises (i) a nucleic acid sequence encoding an SH2-containing inositol-phosphatase having the nucleic acid sequence as shown in SEQ ID NO:7 or FIG. 10, wherein T can also be U;

(ii) a nucleic acid sequence complementary to (i), preferably complementary to the full length nucleic acid sequence shown in SEQ ID NO: 7 or FIG. 10;

(iii) a nucleic acid molecule differing from any of the nucleic acids of (i) and (ii) in codon sequences due to the degeneracy of the genetic code.

The invention also contemplates (a) a nucleic acid molecule comprising a sequence encoding a truncation of the SH2-containing inositol-phosphatase, an analog or homolog of the SH2-containing inositol-phosphatase or a truncation thereof, (herein collectively referred to as "SHIP related protein" or "SHIP related proteins"); (b) a nucleic acid molecule comprising a sequence which hybridizes under high stringency conditions to the nucleic acid encoded by a SH2-containing inositol-phosphatase having the amino acid sequence as shown in SEQ ID NO:2 or FIG. 2(A), or SEQ ID NO:8 or FIG. 11, wherein T can also be U, or complementary sequences thereto, or by a SHIP related protein; and (c) a nucleic acid molecule comprising a sequence which hybridizes under high stringency conditions to the nucleic acid encoded by the SH2-containing inositol-phosphatase having the nucleic acid sequence as shown in SEQ ID NO:1 or FIG. 3, or SEQ ID NO:7 or FIG. 10, wherein T can also be U, or complementary sequences thereto.

The invention further contemplates a purified and isolated double stranded nucleic acid molecule containing a nucleic acid molecule of the invention, hydrogen bonded to a complementary nucleic acid base sequence.

The nucleic acid molecules of the invention may be inserted into an appropriate expression vector, i.e. a vector which contains the necessary elements for the transcription and translation of the inserted coding sequence. Accordingly, recombinant expression vectors adapted for transformation of a host cell may be constructed which comprise a nucleic acid molecule of the invention and one or more transcription and translation elements operatively linked to the nucleic acid molecule.

The recombinant expression vector can be used to prepare transformed host cells expressing SH2-containing inositol-phosphatase or a SHIP related protein. Therefore, the invention further provides host cells containing a recombinant molecule of the invention. The invention also contemplates transgenic non-human mammals whose germ cells and somatic cells contain a recombinant molecule comprising a nucleic acid molecule of the invention which encodes an analog of SH2-containing inositol-phosphatase, i.e. the protein with an insertion, substitution or deletion mutation.

The invention further provides a method for preparing a novel SH2-containing inositol-phosphatase, or a SHIP related protein utilizing the purified and isolated nucleic acid molecules of the invention. In an embodiment a method for preparing an SH2-containing inositol-phosphatase or a SHIP related protein is provided comprising (a) transferring a recombinant expression vector of the invention into a host cell; (b) selecting transformed host cells from untransformed host cells; (c) culturing a selected transformed host cell under conditions which allow expression of the SH2-containing inositol-phosphatase or SHIP related protein; and (d) isolating the SH2-containing inositol-phosphatase or SHIP related protein.

The invention further broadly contemplates a purified and isolated SH2-containing inositol-phosphatase which contains an SH2 domain and which exhibits phosphoIns-5-ptase activity. In an embodiment of the invention, a purified SH2-containing inositol-phosphatase is provided which has the amino acid sequence as shown in SEQ ID NO:2 or FIG. 2(A). In another embodiment of the invention, a purified SH2-containing inositol-phosphatase is provided which has the amino acid sequence as shown in SEQ ID NO:8 or FIG. 11. The purified and isolated protein of the invention may be activated i.e. phosphorylated. The invention also includes truncations of the protein and analogs, homologs, and isoforms of the protein and truncations thereof (i.e. "SHIP related proteins").

The SH2-containing inositol-phosphatase or SHIP related proteins of the invention may be conjugated with other molecules, such as proteins to prepare fusion proteins. This may be accomplished, for example, by the synthesis of N-terminal or C-terminal fusion proteins.

The invention further contemplates antibodies having specificity against an epitope of SH2-containing inositol-phosphatase or a SHIP related protein of the invention. Antibodies may be labelled with a detectable substance and they may be used to detect the SH2-containing inositol-phosphatase or a SHIP related protein of the invention in tissues and cells.

The invention also permits the construction of nucleotide probes which are unique to the nucleic acid molecules of the invention and accordingly to SHIP or a SHIP related protein of the invention. Thus, the invention also relates to a probe comprising a sequence encoding SH2-containing inositol-phosphatase or an SHIP related protein. The probe may be labelled, for example, with a detectable substance and it may be used to select from a mixture of nucleotide sequences a nucleotide sequence coding for a protein which displays one or more of the properties of SHIP.

The invention still further provides a method for identifying a substance which is capable of binding to SHIP, or a SHIP related protein or an activated form thereof, comprising reacting SHIP, or a SHIP related protein, or an activated form thereof, with at least one substance which potentially can bind with SHIP, or a SHIP related protein or an activated form thereof, under conditions which permit the formation of complexes between the substance and SHIP or SHIP related protein or an activated form thereof, and assaying for complexes, for free substance, for non-complexed SHIP or SHIP related protein or an activated form thereof, or for activation of SHIP.

Still further, the invention provides a method for assaying a medium for the presence of an agonist or antagonist of the interaction of SHIP, or a SHIP related protein or an activated form thereof, and a substance which binds to SHIP, a SHIP related protein or an activated form thereof. In an embodiment, the method comprises providing a known concentration of SHIP, or a SHIP related protein, with a substance which is capable of binding to SHIP, or SHIP related protein and a test substance under conditions which permit the formation of complexes between the substance and SHIP, or SHIP related protein, and assaying for complexes, for free substance, for non-complexed SHIP or SHIP related protein, or for activation of SHIP, or SHIP related protein. In a preferred embodiment of the invention, the substance is Shc or a part thereof, or an SH3-containing protein or part thereof.

Still further the invention contemplates a method for assaying for the affect of a substance on the phosphoIns-5-ptase activity of SHIP or a SHIP related protein having phosphoIns-5-ptase activity comprising reacting a substrate which is capable of being hydrolyzed by SHIP or a SHIP related protein to produce a hydrolysis product, with a test substance under conditions which permit the hydrolysis of the substrate, determining the amount of hydrolysis product, and comparing the amount of hydrolysis product obtained with the amount obtained in the absence of the substance to determine the affect of the substance on the phosphoIns-5-ptase activity of SHIP or the SHIP related protein.

Substances which affect SHIP or a SHIP related protein may also be identified using the methods of the invention by comparing the pattern and level of expression of SHIP or a SHIP related protein of the invention in tissues and cells in the presence, and in the absence of the substance.

The substances identified using the method of the invention may be used in the treatment of conditions involving the perturbation of signalling pathways, and in particular in the treatment of proliferative disorders. Accordingly, the substances may be formulated into pharmaceutical compositions for adminstration to individuals suffering from one of these conditions.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 3 shows the nucleic acid sequence of murine SHIP;

FIG. 7 shows the amino acid sequence of Shc;

FIG. 8 shows the nucleic acid sequence of Shc;

FIG. 9 shows the amino acid and nucleic acid sequences of Grb2;

FIG. 10 shows the nucleic acid sequence of human SHIP;

FIG. 11 shows the amino acid sequence of human SHIP;

FIG. 12 shows a comparison of the amino acid sequences of human and murine SHIP; and FIG. 13 shows a comparison of the nucleic acid sequences of human and murine SHIP.

DETAILED DESCRIPTION OF THE INVENTION

Figure 1:
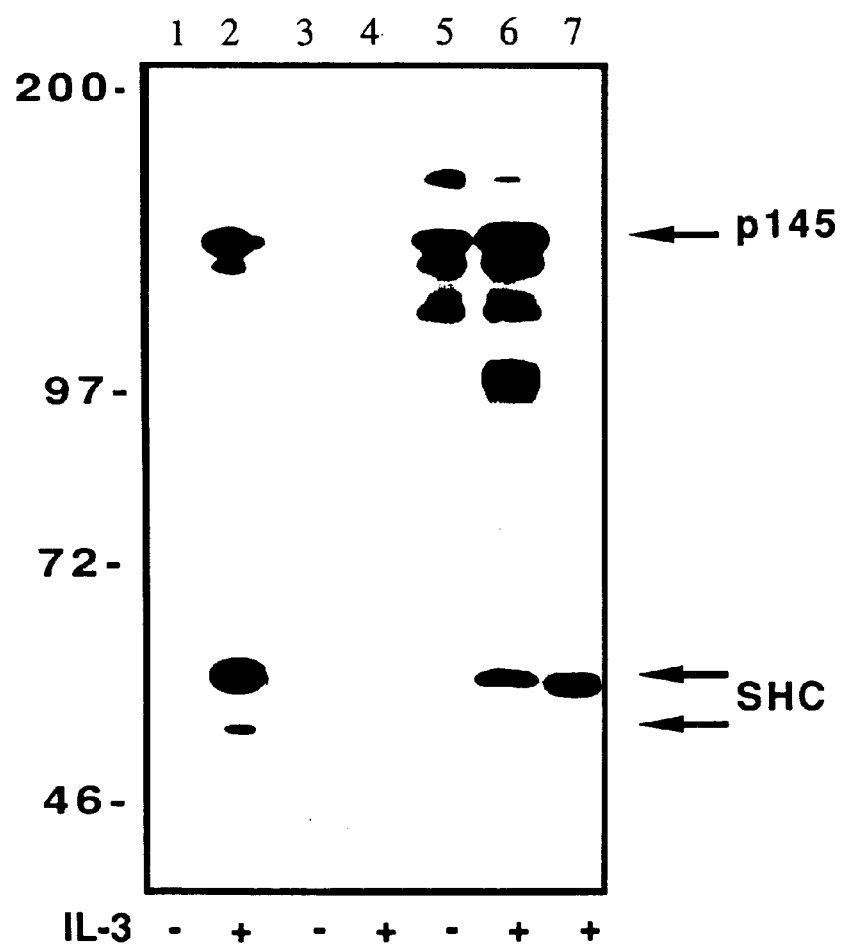
FIG. 1 are immunoblots showing lysates prepared from B6SUtA$_1$ cells, treated ±IL-3, immunoprecipitated with anti-Shc, followed by protein A Sepharose (lanes 1&2) or incubated with GSH bead bound GST-N-SH3 (lanes 3&4) or GSH bead bound GST-C-SH3 (lanes 5&6)

The following standard abbreviations for the amino acid residues are used throughout the specification: A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

I. Nucleic Acid Molecules of the Invention

As hereinbefore mentioned, the invention provides an isolated and purified nucleic acid molecule having a sequence encoding an SH2-containing inositol-phosphatase (SHIP) which contains an SH2 domain and exhibits phosphoIns-5-ptase activity. The term "isolated and purified" refers to a nucleic acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e., sequences located at the 5' and 3' ends of the nucleic acid) from which the nucleic acid is derived. The term "nucleic acid" is intended to include DNA and RNA and can be either double stranded or single stranded.

The murine SHIP coding region was cloned by purifying the protein based on Grb2-C-SH3 affinity chromatography. An unambiguous sequence obtained from the purified protein, VPAEGVSSLNEMINP (SEQ ID NO:11), was used to construct a degenerate oligonucleotide probe. The full length cDNA was cloned using a PCR based strategy and a B6SUtA$_1$ cDNA library as more particularly described in the Example herein. The nucleic acid sequence of murine SHIP is shown in FIG. 3 or in SEQ. I.D. NO. 1. The underlined ATG is the likely start site (starting at nucleic acid 139). However, the predicted protein sequence shown in FIG. 2(A) (SEQ.ID.NO. 2) is from an in frame ATG starting slightly upstream at nucleotide 130. The nucleotides from approximately 151 to 444 code for the SH2 domain; the nucleotides from 1886 to 1934, and 2144 to 2167 code for 5-phosphatase motifs; the nucleotides from 1783 to 2130 code for the 5-ptase domain; nucleotides 2866–2880 and 3175 to 3189 code for the PTB domain target sequences, INPNY (SEQ.ID.NO:9) and ENPLY (SEQ.ID.NO:10); and, the nucleotides 3013 to 3580 code for the proline-rich domain.

The nucleic acid sequence of human SHIP is shown in FIG. 10 and and FIG. 13 (or in SEQ.ID.NO. 7). The human SHIP gene was mapped to chromosome 2 at the junction between q36 and q37. The nucleotides from approximately 141 to 434 in FIG. 10 (SEQ.ID.NO. 7) code for the SH2 domain; the nucleotides from 1876 to 1924 and 2134 to 2157 in FIG. 10 code for 5-phosphatase motifs; the nucleotides from 1773 to 2120 in FIG. 10 code for the 5-ptase domain; nucleotides 2856 to 2870 and 3177 to 3191 in FIG. 10 code for the PTB domain target sequences, INPNY and ENPLY; and the nucleotides 3009 to 3564 in FIG. 10 code for the proline-rich domain. FIG. 13 shows a comparison of the nucleic acid sequences encoding human SHIP and murine SHIP. The nucleic acid sequences encoding human and murine SHIP are 81.6% identical.

The invention includes nucleic acids having substantial homology or identity with the nucleic acid sequences encoding human and murine SHIP. Homology or identity refers to sequence similarity between the nucleic acid sequences and it may be determined by comparing a position in each sequence which is aligned for purposes of comparison. When a position in the compared sequence is occupied by the same nucleotide base, then the molecules are identical or homologous at that position.

It will be appreciated that the invention includes nucleic acid molecules encoding truncations of SHIP, and analogs and homologs of SHIP and truncations thereof (i.e., SHIP related proteins), as described herein. It will further be appreciated that variant forms of the nucleic acid molecules of the invention which arise by alternative splicing of an mRNA corresponding to a cDNA of the invention are encompassed by the invention.

Another aspect of the invention provides a nucleic acid molecule which hybridizes under high stringency conditions to a nucleic acid molecule which comprises a sequence which encodes SHIP having the amino acid sequence shown in FIG. 2(A) or SEQ ID NO:2, or FIG. 11 or SEQ ID NO:8, or to a SHIP related protein, and preferably having the activity of SHIP. Appropriate stringency conditions which promote DNA hybridization are known to those skilled in the art, or can be found in Current Protocols in Molecular Biology, John Wiley & Sons, N.Y. (1989), 6.3.1–6.3.6. For example, 6.0×sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

Isolated and purified nucleic acid molecules encoding a protein having the activity of SHIP as described herein, and having a sequence which differs from the nucleic acid sequence shown in SEQ ID NO:1 or FIG. 3, or SEQ ID NO:7 or FIG. 10, due to degeneracy in the genetic code are also within the scope of the invention. Such nucleic acids encode functionally equivalent proteins (e.g., a protein having SH2-containing inositol-phosphatase activity) but differ in sequence from the sequence of SEQ ID NO:1 or FIG. 3, or SEQ ID NO:7 or FIG. 10, due to degeneracy in the genetic code.

In addition, DNA sequence polymorphisms within the nucleotide sequence of SHIP (especially those within the third base of a codon) may result in "silent" mutations in the DNA which do not affect the amino acid encoded. However, DNA sequence polymorphisms may lead to changes in the amino acid sequences of SHIP within a population. It will be appreciated by one skilled in the art that these variations in one or more nucleotides (up to about 3–4% of the nucleotides) of the nucleic acids encoding proteins having the activity of SHIP may exist among individuals within a population due to natural allelic variation. Any and all such nucleotide variations and resulting amino acid polymorphisms are within the scope of the invention.

An isolated and purified nucleic acid molecule of the invention which comprises DNA can be isolated by preparing a labelled nucleic acid probe based on all or part of the nucleic acid sequence shown in SEQ ID NO: 1 or FIG. 3, (for example, nucleotides 2830 to 2874 encoding VPAEGVSSLNEMINP (SEQ.ID.NO:11); nucleotides encoding NEMINP (SEQ.ID.NO:12) or VPAEGV (SEQ.ID.NO:13); or nucleotides 151 to 444 encoding the SH2 domain), or based on all or part of the nucleic acid sequence shown in SEQ ID NO: 7 or FIG. 10, and using this labelled nucleic acid probe to screen an appropriate DNA library (e.g. a cDNA or genomic DNA library). For instance, a cDNA library made from hemopoietic cells can be used to isolate a cDNA encoding a protein having SHIP activity by screening the library with the labelled probe using standard techniques. Alternatively, a genomic DNA library can be similarly screened to isolate a genomic clone encompassing a gene encoding a protein having SH2-containing inositol-phosphatase activity. Nucleic acids isolated by screening of a cDNA or genomic DNA library can be sequenced by standard techniques.

An isolated and purified nucleic acid molecule of the invention which is DNA can also be isolated by selectively amplifying a nucleic acid encoding SHIP using the polymerase chain reaction (PCR) methods and cDNA or genomic DNA. It is possible to design synthetic oligonucleotide primers from the nucleotide sequence shown in SEQ ID NO:1 or FIG. 3, or shown in SEQ ID NO:7 or FIG. 10, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated and purified nucleic acid molecule of the invention which is RNA can be isolated by cloning a cDNA encoding SHIP into an appropriate vector which allows for transcription of the cDNA to produce an RNA molecule which encodes a protein which exhibits phosphoIns-5-ptase activity. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a protein having SHIP activity can be accomplished by expressing the cDNA in an appropriate host cell by standard techniques, and testing the ability of the expressed protein to associate with Shc and/or hydrolyze a substrate as described herein. A cDNA having the biological activity of SHIP so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of SHIP or a SHIP related protein may be determined using currently available computer software designed for the purpose, such as PC/Gene (IntelliGenetics Inc., Calif.). The intron-exon structure and the transcription regulatory sequences of the gene encoding the SHIP protein may be identified by using a nucleic acid molecule of the invention encoding SHIP to probe a genomic DNA clone library. Regulatory elements can be identified using conventional techniques. The function of the elements can be confirmed by using these elements to express a reporter gene such as the bacterial gene lacZ which is operatively linked to the elements. These constructs may be introduced into cultured cells using standard procedures or into non-human transgenic animal models. In addition to identifying regulatory elements in DNA, such constructs may also be used to identify nuclear proteins interacting with the elements, using techniques known in the art.

The 5' untranslated region of murine SHIP comprises nucleotides 1 to 138 in FIG. 2(A) or SEQ ID. NO. 1, and the 5' untranslated region of human SHIP comprises nucleotides 1 to 128 in FIG. 10 or SEQ ID. NO. 7.

The sequence of a nucleic acid molecule of the invention may be inverted relative to its normal presentation for transcription to produce an antisense nucleic acid molecule. An antisense nucleic acid molecule may be constructed using chemical synthesis and enzymatic ligation reactions using procedures known in the art.

II. SHIP Proteins of the Invention

The amino acid sequence of murine SHIP is shown in SEQ.ID.No.2 or in FIG. 2(A) and the amino acid sequence of human SHIP is shown in SEQ.ID.No. 8 or in FIG. 11. SHIP contains a number of well-characterized regions including an amino terminal src homology 2 (SH2) domain containing the sequence DGSFLVR (SEQ.ID.NO:14) which is highly conserved among SH2 domains; two phosphotyrosine binding (PTB) consensus sequences; proline rich regions near the carboxy terminus containing a class I sequence (PPSQPPLSP) (SEQ.ID.NO:15) and class II sequences (PVKPSR (SEQ.ID.NO:16), PPLSPKK (SEQ.ID.NO:17), AND PPLPVK (SEQ.ID.NO:18)); and two motifs highly conserved among inositol polyphosphate-5-phosphatases (i.e. the sequences WLGDLNYR (SEQ.ID.NO:19) and KYNLPSWCDRVLW (SEQ.ID.NO:20)).

The SHIP protein is expressed in many cell types including hemopoietic cells, bone marrow, lung, spleen, muscles, testes, and kidney.

In addition to the full length SHIP amino acid sequence (SEQ. ID.NO:2 or FIG. 2(A); SEQ. ID.NO:8 or FIG. 11), the proteins of the present invention include truncations of SHIP, and analogs, and homologs of SHIP and truncations thereof as described herein. Truncated proteins may comprise peptides of between 3 and 1090 amino acid residues, ranging in size from a tripeptide to a 1090 mer polypeptide. For example, a truncated protein may comprise the SH2 domain (the amino acids encoded by nucleotides 151 to 444 as shown in FIG. 3 and encoded by nucleotides 141 to 434 in FIG. 10); the proline rich regions (the amino acids encoded by nucleotides 3013 to 3580 in FIG. 3 and encoded by nucleotides 3009 to 3564 in FIG. 10); the 5-phosphatase motifs (amino acids encoded by nucleotides 1886 to 1934 and 2144 to 2167 in FIG. 3 and encoded by nucleotides 1876 to 1924 and 2134 to 2157 in FIG. 10); the 5-ptase domain (the amino acids encoded by nucleotides 1783 to 2130 in FIG. 3 and encoded by nucleotides 1773 to 2120 in FIG. 10); the PTB domain target sequences, INPNY and ENPLY (the amino acids encoded by nucleotides 2866–2880 and 3175 to 3189 in FIG. 3 and encoded by nucleotides 2856 to 2870 and 3177 to 3191 in FIG. 10)); or NPXY (SEQ.ID.NO:21) sequence of SHIP.

The truncated proteins may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end. An isoprenoid may also be attached to a truncated protein comprising the 5-ptase domain to localize SHIP 5-ptase to the inside of the plasma membrane.

The proteins of the invention may also include analogs of SHIP as shown in SEQ. ID. NO. 2 or FIG. 2(A), or as shown in SEQ. ID. NO. 8 or FIG. 11, and/or truncations thereof as described herein, which may include, but are not limited to, SHIP (SEQ. ID. NO. 2 or FIG. 2(A); SEQ. ID. NO. 8 or FIG. 11), containing one or more amino acid substitutions, insertions, and/or deletions. Amino acid substitutions may be of a conserved or non-conserved nature. Conserved amino acid substitutions involve replacing one or more amino acids of the SHIP amino acid sequence with amino acids of similar charge, size, and/or hydrophobicity characterisitics. When only conserved substitutions are made the resulting analog should be functionally equivalent to SHIP (SEQ. ID. NO. 2 or FIG. 2(A); SEQ. ID. NO. 8 or FIG. 11). Non-conserved substitutions involve replacing one or more amino acids of the SHIP amino acid sequence with one or more amino acids which possess dissimilar charge, size, and/or hydrophobicity characteristics. By way of example, D675 may be replaced with A675 in FIG. 2(A) (or 672 in FIG. 11) to create an analog which does not have 5-ptase activity.

One or more amino acid insertions may be introduced into SHIP (SEQ. ID. NO. 2 or FIG. 2(A); SEQ. ID. NO. 8 or FIG. 11). Amino acid insertions may consist of single amino acid residues or sequential amino acids ranging from 2 to 15 amino acids in length. For example, amino acid insertions may be used to destroy the PTB domain target sequences or the proline-rich consensus sequences so that SHIP can no longer bind SH3-containing proteins.

Deletions may consist of the removal of one or more amino acids, or discrete portions (e.g. one or more of the SH2 domain, PTB consensus sequences; the sequences conserved among inositol polyphosphate-5-phosphatases) from the SHIP (SEQ. ID. NO. 2 or FIG. 2(A), SEQ. ID. NO. 8 or FIG. 11) sequence. The deleted amino acids may or may not be contiguous. The lower limit length of the resulting analog with a deletion mutation is about 10 amino acids, preferably 100 amino acids.

It is anticipated that if amino acids are replaced, inserted or deleted in sequences outside the amino terminal src homology 2 (SH2) domain, the phosphotyrosine binding (PTB) consensus sequences, the proline rich region and motifs highly conserved among inositol polyphosphate-5-phosphatases, that the resulting analog of SHIP will associate with Shc and exhibit phosphoIns-5-ptase activity.

The proteins of the invention also include homologs of SHIP (SEQ. ID. NO. 2 or FIG. 2(A); SEQ. ID. NO. 8 or FIG. 11) and/or truncations thereof as described herein. Homology or identity refers to sequence similarity between sequences and it may be determined by comparing a position in each sequence which may be aligned for purposes of comparison. A degree of homology between sequences is a function of the number of matching positions shared by the sequences. Homologs will generally have the same regions which are characteristic of SHIP, namely an amino terminal src homology 2 (SH2) domain, two phosphotyrosine binding (PTB) consensus sequences, a proline rich region and two motifs highly conserved among inositol polyphosphate-5-phosphatases. It is anticipated that, outside of the well-characterized regions of SHIP specified herein (i.e. SH2 domain, PTB domain etc), a protein comprising an amino acid sequence which is about 50% similar, preferably 80 to 90% similar, with the amino acid sequences shown in SEQ ID NO:2 or FIG. 2(A), or SEQ. ID. NO. 8 or FIG. 11, will exhibit phosphoIns-5-ptase activity and associate with Shc.

A comparison of the amino acid sequences of murine and human SHIP are shown in FIG. 12. As shown in FIG. 12, human and murine SHIP are 87.2% identical at the amino acid level.

The invention also contemplates isoforms of the protein of the invention. An isoform contains the same number and kinds of amino acids as the protein of the invention, but the isoform has a different molecular structure. The isoforms contemplated by the present invention are those having the same properties as the protein of the invention as described herein.

The present invention also includes SHIP or a SHIP related protein conjugated with a selected protein, or a selectable marker protein (see below) to produce fusion proteins. Further, the present invention also includes activated or phosphorylated SHIP proteins of the invention. Additionally, immunogenic portions of SHIP and SHIP related proteins are within the scope of the invention.

SHIP and SHIP related proteins of the invention may be prepared using recombinant DNA methods. Accordingly, the nucleic acid molecules of the present invention having a sequence which encodes SHIP or a SHIP related protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein sequence. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native SHIP and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, or an RNA molecule which is antisense to the nucleotide sequence of SEQ ID NO: 1 or FIG. 2(A), or SEQ. ID. NO. 8 or FIG. 11. Regulatory sequences operatively linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The recombinant expression vectors of the invention may also contain a selectable marker gene which facilitates the selection of host cells transformed or transfected with a recombinant molecule of the invention. Examples of selectable marker genes are genes encoding a selectable marker protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase (GST), maltose E binding protein, or protein A, respectively, to the recombinant protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include *E. coli, B. subtilis, Salmonella typhimurium,* and various species within the genus' Pseudomonas, Streptomyces, and Staphylococcus, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Amann et al., (1988) Gene 69:301–315) and pET 11d (Studier et al., Gene Expression Technology: Methods in Enzymology 185, Academic Press, San Diego, Calif. (1990) 60–89).

Yeast and fungi host cells suitable for carrying out the present invention include, but are not limited to *Saccharomyces cerevisae,* the genera Pichia or Kluyveromyces and various species of the genus Aspergillus. Examples of vectors for expression in yeast *S. cerivisae* include pYepSec1 (Baldari. et al., (1987) Embo J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.). Protocols for the transformation of yeast and fungi are well known to those of ordinary skill in the art.(see Hinnen et al., PNAS USA 75:1929, 1978; Itoh et al., J. Bacteriology 153:163, 1983, and Cullen et al. (Bio/Technology 5:369, 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., (1987) Nature 329:840) and pMT2PC (Kaufman et al. (1987), EMBOJ. 6:187–195).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47–58, 1987, which reviews the use of *Agrobacterium rhizogenes* vectors; see also Zambryski et al., Genetic Engineering, Principles and Methods, Hollaender and Setlow (eds.), Vol. VI, pp. 253–278, Plenum Press, New York, 1984, which describes the use of expression vectors for plant cells, including, among others, pAS2022, pAS2023, and pAS2034).

Insect cells suitable for carrying out the present invention include cells and cell lines from Bombyx or Spodotera species. Baculovirus vectors available for expression of proteins in cultured insect cells (SF 9 cells) include the pAc series (Smith et al., (1983) Mol. Cell Biol. 3:2156–2165) and the pVL series (Lucklow, V. A., and Summers, M. D., (1989) Virology 170:31–39).

Alternatively, the proteins of the invention may also be expressed in non-human transgenic animals such as, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

N-terminal or C-terminal fusion proteins comprising SHIP or a SHIP related protein of the invention conjugated with other molecules, such as proteins may be prepared by fusing, through recombinant techniques, the N-terminal or C-terminal of SHIP or a SHIP related protein, and the sequence of a selected protein or selectable marker protein with a desired biological function. The resultant fusion proteins contain SHIP or a SHIP related protein fused to the selected protein or marker protein as described herein. Examples of proteins which may be used to prepare fusion proteins include immunoglobulins, glutathione-S-transferase (GST), hemagglutinin (HA), and truncated myc. The present inventor has made GST fusion proteins containing the SH2 domain of SHIP and GST fusion proteins containing the 5-ptase domain attached to an isoprenoid to localize SHIP 5-ptase to the inside of the plasma membrane.

Phosphorylated or activated SHIP or SHIP related proteins of the invention may be prepared using the method described in Reedijk et al. The EMBO Journal 11(4):1365, 1992. For example, tyrosine phosphorylation may be induced by infecting bacteria harbouring a plasmid containing a nucleotide sequence of the invention, with a λgt11 bacteriophage encoding the cytoplasmic domain of the Elk tyrosine kinase as an Elk fusion protein. Bacteria containing the plasmid and bacteriophage as a lysogen are isolated. Following induction of the lysogen, the expressed protein becomes phosphorylated by the tyrosine kinase.

IV. Utility of the Nucleic Acid Molecules and Proteins of the Invention

The nucleic acid molecules of the invention allow those skilled in the art to construct nucleotide probes for use in the detection of nucleic acid sequences in biological materials. Suitable probes include nucleic acid molecules based on nucleic acid sequences encoding at least 6 sequential amino acids from regions of the SHIP protein as shown in SEQ.ID NO:2 or FIG. 2(A), and SEQ.ID NO:8 or FIG. 11. For example, a probe may be based on the nucleotides 2830 to 2874 in FIG. 3 (or SEQ ID.NO. 1) encoding VPAEGVSSL-NEMINP (SEQ.ID.NO:11); the nucleotides encoding NEMINP (SEQ.ID.NO:12) or VPAEGV (SEQ.ID.NO:13); or the nucleotides 151 to 445 in FIG. 3 (or SEQ ID.NO. 1) encoding the SH2 domain. Preferably, the probe comprises a 1 to 1.5 kb segment corresponding to the 5' and 3' ends of the 5 Kb SHIP mRNA. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode SHIP, and SHIP related proteins. The nucleotide probes may therefore be useful in the diagnosis of disorders of the hemopoietic system including chronic myelogenous leukemia, and acute lymphocytic leukemia, etc.

SHIP or a SHIP related protein of the invention can be used to prepare antibodies specific for the proteins. Antibodies can be prepared which bind a distinct epitope in an unconserved region of the protein. An unconserved region of the protein is one which does not have substantial sequence homology to other proteins, for example the regions outside the well-characterized regions of SHIP as described herein. Alternatively, a region from one of the well-characterized domains (e.g. SH2 domain) can be used to prepare an antibody to a conserved region of SHIP or a SHIP related protein. Antibodies having specificity for SHIP or a SHIP related protein may also be raised from fusion proteins created by expressing for example, trpE-SHIP fusion proteins in bacteria as described herein.

Conventional methods can be used to prepare the antibodies. For example, by using a peptide of SHIP or a SHIP related protein, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for SHIP or a SHIP related protein as described herein.

The term "antibody" as used herein is intended to include fragments thereof which also specifically react with a protein, or peptide thereof, having the activity of SHIP. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of SHIP antigens of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816, 567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.) Specific antibodies, or antibody fragments, reactive against proteins of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). Alternatively, a SCID-hu mouse, for example the model developed by Genpharm, can be used to produce antibodies, or fragments thereof.

Antibodies specifically reactive with SHIP or a SHIP related protein, or derivatives thereof, such as enzyme conjugates or labeled derivatives, may be used to detect SHIP in various biological materials, for example they may be used in any known immunoassays which rely on the binding interaction between an antigenic determinant of SHIP or a SHIP related protein, and the antibodies. Examples of such assays are radioimmunoassays, enzyme immunoassays (e.g. ELISA), immunofluorescence, immunoprecipitation, latex agglutination, hemagglutination, and histochemical tests. Thus, the antibodies may be used to detect and quantify SHIP in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect SHIP, to localise it to particular cells and tissues and to specific subcellular locations, and to quantitate the level of expression.

Cytochemical techniques known in the art for localizing antigens using light and electron microscopy may be used to detect SHIP. Generally, an antibody of the invention may be labelled with a detectable substance and SHIP may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against SHIP. By way of example, if the antibody having specificity against SHIP is a rabbit IgG antibody, the second antibody may be goat anti-rabbit gamma-globulin labelled with a detectable substance as described herein.

Where a radioactive label is used as a detectable substance, SHIP may be localized by radioautography. The results of radioautography may be quantitated by determining the density of particles in the radioautographs by various optical methods, or by counting the grains.

As discussed herein, SHIP associates with Shc following cytokine stimulation of hemopoietic cells, and it has a role in regulating proliferation, differentiation, activation and metabolism of cells of the hemopoietic system. Therefore, the above described methods for detecting nucleic acid molecules of the invention and SHIP, can be used to monitor proliferation, differentiation, activation and metabolism of cells of the hemopoietic system by detecting and localizing SHIP and nucleic acid molecules encoding SHIP. It would also be apparent to one skilled in the art that the above described methods may be used to study the developmental expression of SHIP and, accordingly, will provide further insight into the role of SHIP in the hemopoietic system.

SHIP has unique and important roles in the regulation of signalling pathways that control gene expression, cell proliferation, differentiation, activation, and metabolism. This finding permits the identification of substances which affect SHIP regulatory systems and which may be used in the treatment of conditions involving perturbation of signalling pathways. The term "SHIP regulatory system" refers to the interaction of SHIP or a SHIP related protein and Shc or a part thereof, to form a SHIP-Shc complex thereby activating a series of regulatory pathways that control gene expression, cell division, cytoskeletal architecture and cell metabolism. Such pathways include the Ras pathway, the pathway that regulates the breakdown of polyphosphoinositides through phospholipase C, and PI-3-kinase activated pathways, such as the emerging rapamycin-sensitive protein kinase B (PKB/Akt) pathway.

A substance which affects SHIP and accordingly a SHIP regulatory system may be assayed using the above described methods for detecting nucleic acid molecules and SHIP and SHIP related proteins, and by comparing the pattern and level of expression of SHIP or SHIP related proteins in the presence and absence of the substance.

Substances which affect SHIP can also be identified based on their ability to bind to SHIP or a SHIP related protein. Therefore, the invention also provides methods for identifying substances which are capable of binding to SHIP or a SHIP related protein. In particular, the methods may be used to identify substances which are capable of binding to, and in some cases activating (i.e., phosphorylating) SHIP or a SHIP related protein of the invention.

Substances which can bind with SHIP or a SHIP related protein of the invention may be identified by reacting SHIP or a SHIP related protein with a substance which potentially binds to SHIP or a SHIP related protein, under conditions which permit the formation of substance -SHIP or -SHIP related protein complexes and assaying for complexes, for free substance, or for non-complexed SHIP or SHIP related protein, or for activation of SHIP or SHIP related protein. Conditions which permit the formation of substance SHIP or SHIP related protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against SHIP or SHIP related protein or the substance, or labelled SHIP or SHIP related protein, or a labelled substance may be utilized. The antibodies, proteins, or substances may be labelled with a detectable substance as described above.

Substances which bind to and activate SHIP or a SHIP related protein of the invention may be identified by assaying for phosphorylation of the tyrosine residues of the protein, for example using antiphosphotyrosine antibodies and labelled phosphorus.

SHIP or SHIP related protein, or the substance used in the method of the invention may be insolubilized. For example, SHIP or SHIP related protein or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinylether-maleic acid copolymer, amino acid copolymer, ethylene-maleic acid copolymer, nylon, silk, etc. The carrier may be in the shape of, for example, a tube, test plate, beads, disc, sphere etc.

The insolubilized protein or substance may be prepared by reacting the material with a suitable insoluble carrier using known chemical or physical methods, for example, cyanogen bromide coupling.

The proteins or substance may also be expressed on the surface of a cell using the methods described herein.

The invention also contemplates a method for assaying for an agonist or antagonist of the binding of SHIP or a SHIP related protein with a substance which is capable of binding with SHIP or a SHIP related protein. The agonist or antagonist may be an endogenous physiological substance or it may be a natural or synthetic substance. Substances which are capable of binding with SHIP or a SHIP related protein may be identified using the methods set forth herein. In a preferred embodiment, the substance is Shc, or a part of Shc, in particular the SH2 domain of Shc, PTB recognition sequences of Shc, or the region containing $Y^{317}$ of Shc (i.e. amino acids 310 to 322) or an activated form thereof. The nucleic acid sequence and the amino acid sequence of Shc are shown in FIGS. 7 & 8 (SEQ ID. Nos. 3 and 4), respectively. Shc, or a part of Shc, may be prepared using conventional methods, or they may be prepared as fusion proteins (See Lioubin, M. N. Et al., Mol. Cell. Biol. 14(9) :5682, 1994, and Kavanaugh, W. M., and L. T. Williams, Science 266:1862, 1994 for methods for making Shc and Shc fusion proteins). Shc, or part of Shc may be activated i.e. phosphorylated using the methods described for example by Reedijk et al. (The EMBO Journal, 11(4):1365, 1992) for producing a tyrosine phosphorylated protein. The substance may also be an SH3 containing protein such as Grb2, or a part of Grb2, in particular the SH3 domain of Grb2. The nucleic acid sequence and the amino acid sequence of Grb2 are shown in FIG. 9 (SEQ. ID. 5 and NO. 6, respectively).

Therefore, in accordance with a preferred embodiment, a method is provided which comprises providing a known concentration of SHIP or a SHIP related protein, incubating SHIP or the SHIP related protein with Shc, or a part of Shc, and a suspected agonist or antagonist under conditions which permit the formation of Shc-SHIP or Shc-SHIP related protein complexes, and assaying for Shc-SHIP or Shc-SHIP related protein complexes, for free Shc, for non-complexed SHIP or SHIP related proteins, or for activation of SHIP or SHIP related proteins. Conditions which permit the formation of Shc-SHIP or Shc-SHIP related protein complexes and methods for assaying for Shc-SHIP or Shc-SHIP related protein complexes, for free Shc, for non-complexed SHIP or SHIP related protein, or for activation of SHIP or SHIP related protein are described herein.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of SHIP or a SHIP related protein with a substance which is capable of binding to SHIP or a SHIP related protein. Thus, the invention may be used to assay for a substance that competes for the same binding site of SHIP or a SHIP related protein.

The methods described above may be used to identifying a substance which is capable of binding to an activated SHIP or SHIP related protein, and to assay for an agonist or antagonist of the binding of activated SHIP or SHIP related protein, with a substance which is capable of binding with activated SHIP or activated SHIP related protein. An activated (i.e. phosphorylated) SHIP or SHIP related protein may be prepared using the methods described for example in Reedijk et al. The EMBO Journal, 11(4):1365, 1992 for producing a tyrosine phosphorylated protein.

It will also be appreciated that intracellular substances which are capable of binding to SHIP or a SHIP related protein may be identified using the methods described herein. For example, tyrosine phosphorylated proteins (such as the 97 kd and 75 kd proteins) and non-tyrosine phosphorylated proteins which bind to SHIP or a SHIP related protein may be isolated using the method of the invention, cloned, and sequenced.

The invention also contemplates a method for assaying for the affect of a substance on the phosphoIns-5-ptase activity of SHIP or a SHIP related protein having phosphoIns-5-ptase activity comprising reacting a substrate which is capable of being hydrolyzed by SHIP or SHIP related protein to produce a hydrolysis product, with a substance which is suspected of affecting the phosphoIns-5-ptase activity of SHIP or a SHIP related protein, under conditions which permit the hydrolysis of the substrate, determining the amount of hydrolysis product, and comparing the amount of hydrolysis product obtained with the amount obtained in the absence of the substance to determine the affect of the substance on the phosphoIns-5-ptase activity of SHIP or SHIP related proteins. Suitable substrates include phosphatidylinositol trisphosphate (PtdIns-3,4,5-$P_3$) and inositol tetraphosphate (Ins-1,3,4,5-$P_4$). The former substrate is hydroylzed to PtdIns-3,4-$P_2$ which may be identified by incubation with phosphoIns-4-ptase which converts the bis phosphate product to PtdIns-3-P. The latter is hydrolyzed to Ins-1,3,4-$P_3$ which is identified by treatment with phosphoIns-1-ptase and phosphoIns-4-ptase. Conditions which permit the hydrolysis of the substrate, may be selected having regard to factors such as the nature and amounts of the substance, substrate, and the amount of SHIP or SHIP related proteins.

The invention further provides a method for assaying for a substance that affects a SHIP regulatory pathway comprising administering to a non-human animal or to a tissue of an animal, a substance suspected of affecting a SHIP regulatory pathway, and quantitating SHIP or nucleic acids encoding SHIP, or examining the pattern and/or level of expression of SHIP, in the non-human animal or tissue. SHIP may be quantitated and its expression may be examined using the methods described herein.

The substances identified by the methods described herein, may be used for modulating SHIP regulatory pathways and accordingly may be used in the treatment of conditions involving perturbation of SHIP signalling pathways. In particular, the substances may be particularly useful in the treatment of disorders of the hemopoietic system such as chronic myelogenous leukemia, and acute lymphocytic leukemia.

SHIP is believed to enhance proliferation. Therefore, inhibitors of SHIP (e.g. truncated or point mutants or antisense) may be useful in reversing disorders involving excessive proliferation, and stimulators of SHIP may be useful in the treatment of disorders requiring stimulation of proliferation. Accordingly, the substances identified using the methods of the invention may be used to stimulate or inhibit cell proliferation associated with disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, arthrosclerosis, angiogenesis, and viral infections, in particular HIV infections; and autoimmune diseases including systemic lupus erythematosus, Wegener's granulomatosis, rheumatoid arthritis, sarcoidosis, polyarthritis, pemphigus, pemphigoid, erythema multiforme, Sjogren's syndrome, inflammatory bowel disease, multiple sclerosis, myasthenia gravis, keratitis, scleritis, Type I diabetes, insulin-dependent diabetes mellitus, Lupus Nephritis, allergic encephalomyelitis. Substances which stimulate cell proliferation identified using the methods of the invention may be useful in the treatment of conditions involving damaged cells including conditions in which degeneration of tissue occurs such as arthropathy, bone resorption, inflammatory disease, degenerative disorders of the central nervous system; and for promoting wound healing.

The substances may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., U.S.A. 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The reagents suitable for applying the methods of the invention to identify substances that affect a SHIP regulatory system may be packaged into convenient kits providing the necessary materials packaged into suitable containers. The kits may also include suitable supports useful in performing the methods of the invention.

The invention also provides methods for examining the function of the SHIP protein. Cells, tissues, and non-human animals lacking in SHIP expression or partially lacking in SHIP expression may be developed using recombinant expression vectors of the invention having specific deletion or insertion mutations in the SHIP gene. For example, the PTB recognition sequences, SH2 domain, 5-ptase domain, or proline-rich sequences may be deleted. A recombinant expression vector may be used to inactivate or alter the endogenous gene by homologous recombination, and thereby create a SHIP deficient cell, tissue or animal.

Null alleles may be generated in cells, such as embryonic stem cells by deletion mutation. A recombinant SHIP gene may also be engineered to contain an insertion mutation which inactivates SHIP. Such a construct may then be introduced into a cell, such as an embryonic stem cell, by a technique such as transfection, electroporation, injection etc. Cells lacking an intact SHIP gene may then be identified, for example by Southern blotting, Northern Blotting or by assaying for expression of SHIP using the methods described herein. Such cells may then be fused to embryonic stem cells to generate transgenic non-human animals deficient in SHIP. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on SHIP expression.

The following non-limiting example are illustrative of the present invention:

EXAMPLES

The following materials and methods were utilized in the investigations outlined in example 1:

Purification Protocol 20 liters of B6SUtA$_1$ cells, grown to confluence in RPMI containing 10% FCS and 5 ng/ml of GM-CSF, were lysed at 2×107 cells/ml with PSB containing 0.5% NP40 (Liu et al., Mol. Cell. Biol. 14, 6926 (1994)) and incubated with GSH-beads bearing GST-Grb2-C-SH3. Bound material was eluted by boiling with 1% SDS, 50 mM Tris-Cl, pH 7.5, and diluted to reduce the SDS to <0.2% for Amicon YM100, Microcon 30 concentration and 3 rounds of Bio-Sep SEC S3000 (Phenomenex) HPLC to remove GST-Grb2-C-SH3 and other low molecular weight material. Following 2D-PAGE (P. H. O'Farrell, J. Biol. Chem. 250, 4007 (1975)), transfer to a PVDF membrane (Liu et al., Mol. Cell. Biol. 14, 6926 (1994)), and Ponceau S staining, the 145-kD spot was excised and sent to the Harvard Microchemistry Facility for trypsin digestion, C$_{18}$ HPLC and amino acid sequencing.

Cloning of cDNA for p145

Degenerate 3' oligonucleotides were synthesized based on the peptide sequence NEMINP, ie 5' GACATCGATGG(G,A)TT(T,G,A)ATCAT(C,T)TC (A,G)TT-3' (SEQ.ID.NO:22) to carry out PCR amplification 3' and 5' from a plasmid library of randomly primed B6SUtA$_1$ cDNA employing 5' PCR primers based on plasmid vector sequence flanking the cDNA insertion site. PCR reactions (Expand™ Long Template PCR System, Boehringer Mannheim) were separated on TAE-agarose gels, transferred to Hybond-N+ Blotting membrane (Amersham) and probed for hybridizing bands with a γ-$^{32}$P-dATP end-labelled degenerate oligonucleotide based on the upstream, but not overlapping, peptide sequence VPAEGV:5'GTAACGGGT(C,T,A,G)CC(C,T,A,G)GC (C,T,A,G)GA(A,G)G(C,T,A,G)GT-3' (SEQ.ID.NO:23). A 314 bp hybridizing DNA fragment was identified, gel purified, subcloned into Bluescript KS+, sequenced and the projected translation confirmed to match that of the original amino acid sequence obtained with the exception of E→C at amino acid #4: VPA CGVSSLNEMINP (SEQ.ID NO:24). Specific primers were synthesized based on the DNA sequence to proceed both 3' and 5' of the 314 bp original clone to clone 3 overlapping cDNAs totalling 4047 bp in length and encoding a complete coding sequence of 1190 amino acids. DNA sequence was obtained for both strands (Amplicycle, Perkin Elmer), employing both subcloning and oligomer primers. Data base comparisons were performed with the MPSearch program, using the Blitz server operated by the European Molecular Biology Laboratory (Heidelberg, Germany).

Determining if p145 is a PhosphoIns-5-ptase

PtdIns[$^{32}$P]-3,4,5-P$_3$ was prepared using PtdIns-4,5-P$_2$ and recombinant PtdIns-3-kinase provided by Dr. L. Williams (Chiron Corp) (17). 5-ptase activity was measured by evaporating 30,000 cpm of TLC purified PtdIns[$^{32}$P]-3,4,5-P$_3$ with 150 ug phosphatidylserine under N$_2$ and resuspending by sonication in assay buffer. Reaction mixtures (25 μl) containing immunoprecipitate or 5-ptase II, 50 mM Tris-Cl, pH 7.5, 10 mM MgCl$_2$ and substrate were rocked for 30 min at 37° C. Reactions were stopped and the product separated by TLC (L. A. Norris and P. W. Majerus, J. Biol. Chem. 269, 8716 (1994)). Hydrolysis of [3H]Ins-1,3,4,5-P4 by immunoprecipitates was measured as above in 25 μl containing 16 μM [3H]Ins-1,3,4,5-P4 (6000 cpm/nmol) under conditions where the reaction was linear with time (20 min, 37° C.) and enzyme amount (C. A. Mitchell et al., J. Biol. Chem. 264, 8873 (1989)). Proof that the InsP3 product was [3H]Ins-1,3,4-P3 was obtained by incubation with recombinant inositol-polyphosphate-4- and 1-phosphatase and the bis phosphate products separated on Dowex-formate.

Legends for Figures Discussed in Example 1

FIG. 1. The Grb2-C-SH3 domain specifically binds the tyrosine phosphorylated, Shc-associated p145. Lysates prepared from B6SUtA$_1$ cells (2), treated ±IL-3, were either immunoprecipitated with anti-Shc (Transduction Laboratories), followed by protein A Sepharose (lanes 1&2) or incubated with GSH bead bound GST-Grb2-N-SH3 (lanes 3&4) or GSH bead bound GST-Grb2-C-SH3 (lanes 5&6). Proteins were eluted by boiling in SDS sample buffer and subjected to Western analysis using 4G10. For lane 7, lysates from IL-3-stimulated B6SUtA$_1$ cells were incubated with GSH bead bound GST-Grb2-C-SH3, and anti-Shc immunoprecipitates carried out with the unbound material.

Figure 2:
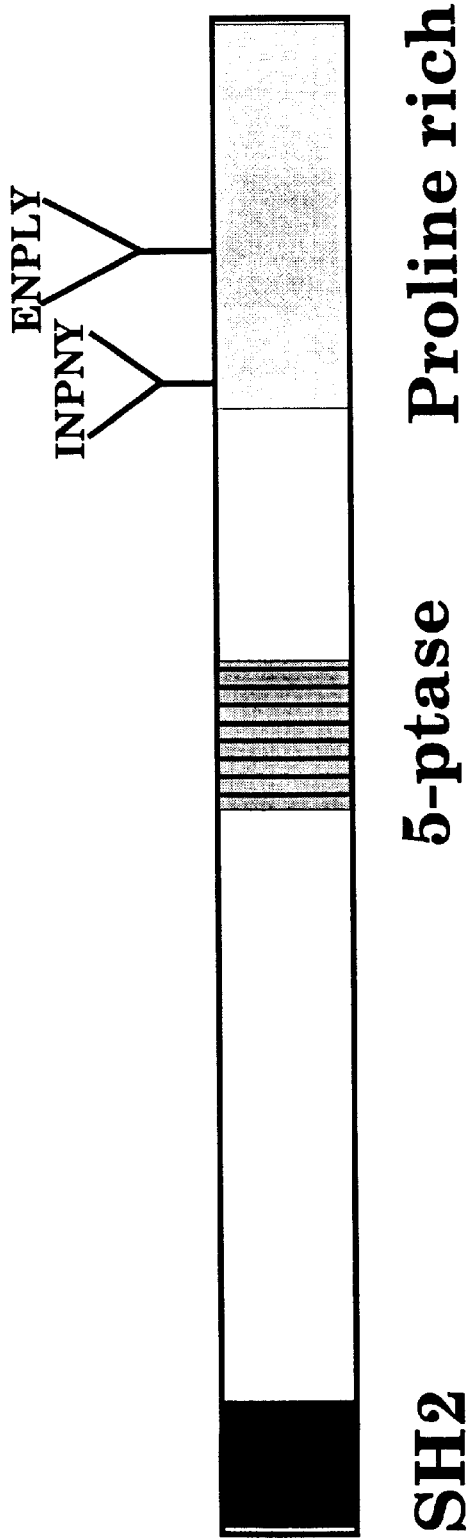
FIGS. 2A and 2B show the amino acid sequence of murine SHIP (A) and a schematic diagram of the domains of the novel protein of the invention (B)

FIG. 2. Amino acid sequence of p145. (A) Deduced amino acid sequence of p145. The hatched box indicates the SH2 domain; the heavily underlined amino acids, the 2 target sequences for binding to PTB domains; the asterisks, the location of the proline rich motifs; and the lightly underlined amino acids, the 2 conserved 5-ptase motifs. Data base comparisons were performed with the MPSearch program using the Blitz server operated by the European Molecular Biology Laboratory (Heidelberg, Germany). (B) Diagrammatic representation of the various domains within p145.

Figure 4:
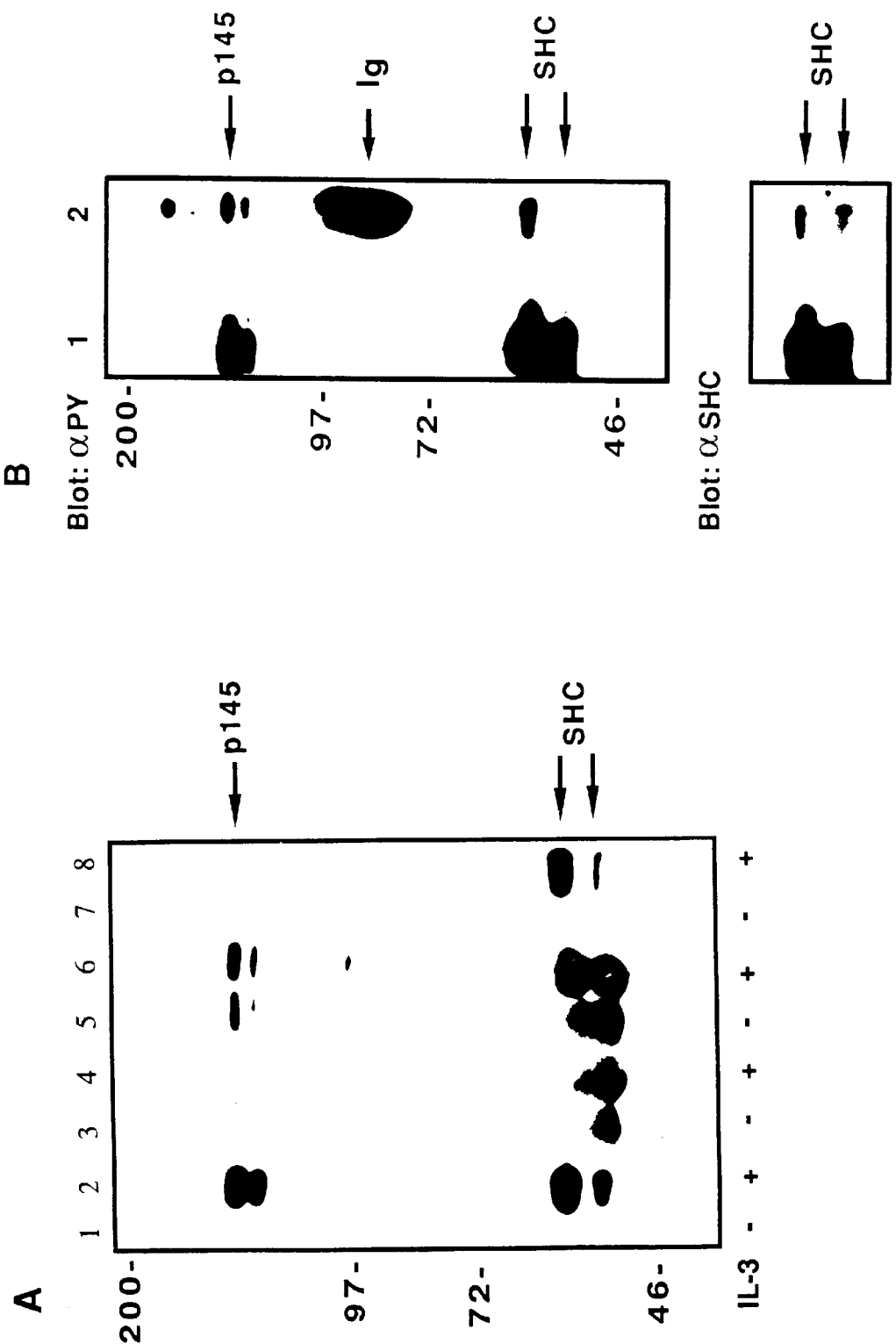
FIGS. 4A and 4B show immunoblots of lysates from B6SUtA$_1$ cells, treated ±IL-3, immunoprecipitated with anti-Shc (lanes 1&2), NRS (lanes 3&4) or anti-15mer (lanes 5&6) or precleared with anti-15$^{mer}$ and then immunoprecipitated with anti-Shc (lanes 7&8) (A); and lysates from B6SUtA$_1$ cells, stimulated with IL-3, immunoprecipitated with anti-Shc (lane 1) or anti-15$^{mer}$ (lane 2) and bound proteins eluted with SDS-sample buffer containing N-ethylmaleimide in lieu of 2-mercaptoethanol (B)

FIG. 4. Anti-15$^{mer}$ antiserum recognizes the Shc-associated p145 and co-precipitates Shc. (A) Lysates from B6SUtA$_1$ cells, treated ±IL-3, were either immunoprecipitated with anti-Shc (lanes 1&2), NRS (lanes 3&4) or anti-15$^{mer}$ (lanes 5&6) or precleared with anti-15$^{mer}$ and then immunoprecipitated with anti-Shc (lanes 7&8). Western analysis was then performed with 4G10. (B) Lysates from B6SUtA$_1$ cells, stimulated with IL-3, were immunoprecipitated with anti-Shc or anti-15$^{mer}$ and the bound proteins eluted at 23° C. for 30 min with SDS-sample buffer containing 1 mM N-ethylmaleimide in lieu of 2-mercaptoethanol. Western blotting was then carried out with 4G10 (upper panel) and the blot reprobed with anti-Shc (lower panel).

Figure 5:
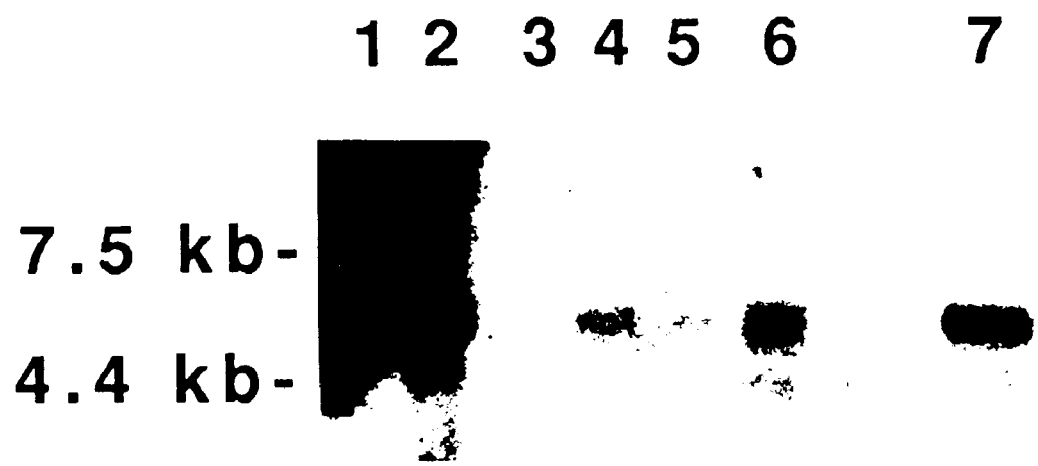
FIG. 5 shows Northern blot analysis of 2 $\mu$g of polyA RNA from various tissues probed with a random primer-labeled PCR fragment encompassing a 1.5-kb fragment corresponding to the 3' end of the p145 cDNA (lanes 1–6, spleen, lung, liver, skeletal muscle, kidney and testes, respectively (Clontech); lane 7, separately prepared blot of bone marrow.

FIG. 5. Expression of p145 RNA in murine tissues. Northern blot analysis of 2 μg of polyA RNA from various tissues probed with a random primer-labeled PCR fragment encompassing a 1.5-kb fragment corresponding to the 3' end of the p145 cDNA (lanes 1–6, spleen, lung, liver, skeletal muscle, kidney and testes, respectively (Clontech); lane 7, separately prepared blot of bone marrow). Similar intensities were observed upon probing with a random primer-labeled PCR fragment encompassing a 1.5-kb fragment corresponding to the 5' end. Exposure time was 30 hrs. In addition to the prominant 5-kb band, a faint band of 4.5-kb was apparent on the autoradiogram.

Figure 6:
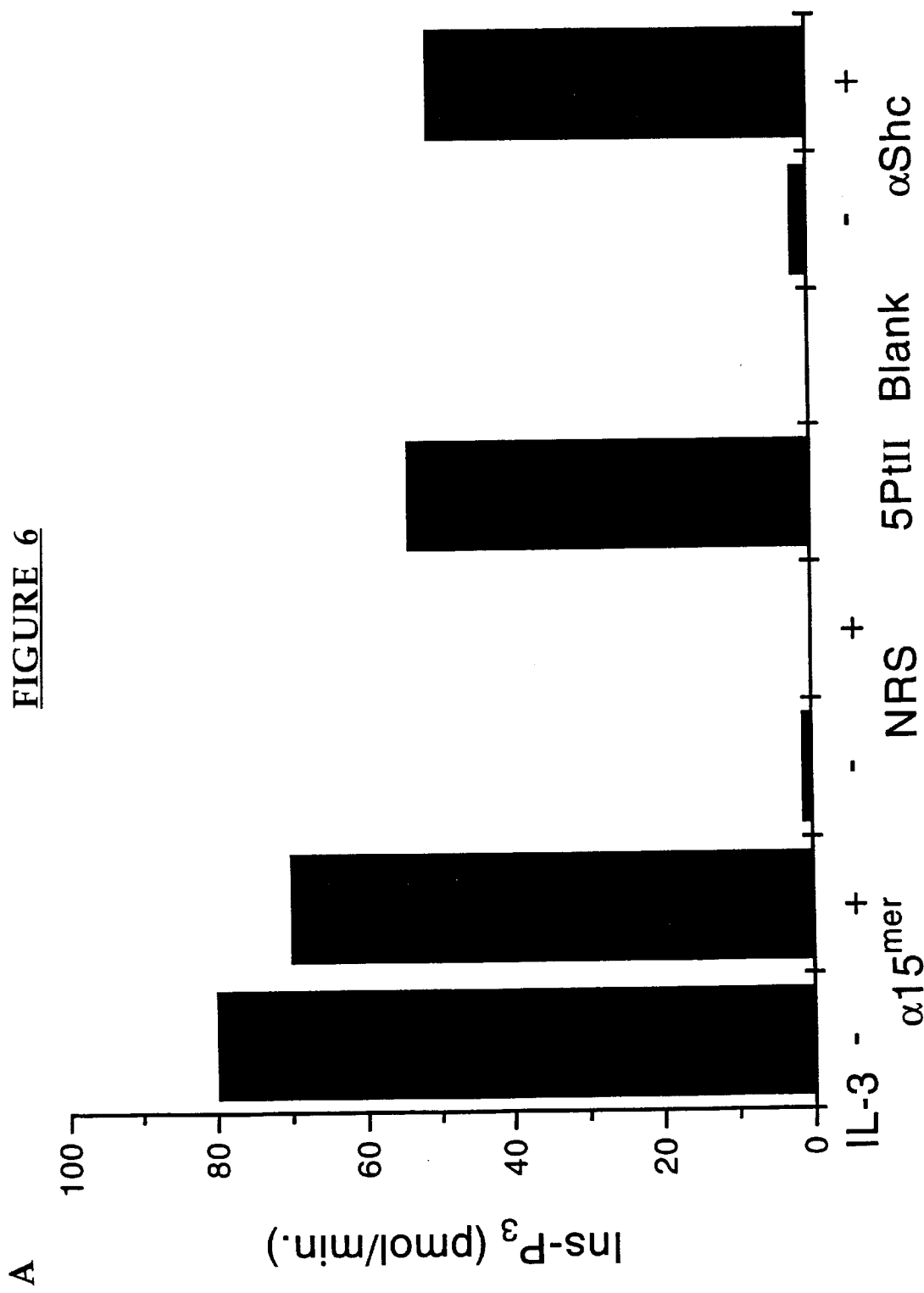
FIGS. 6A and 6B are a graph showing the results of anti-15$^{mer}$, anti-Shc and NRS immunoprecipitates with B6SUtA$_1$ cell lysate incubated with [$^3$H]Ins-1,3,4,5-P$_4$ under conditions where product formation was linear with time (A); and shows immunoblots of anti-15$^{mer}$, NRS and anti-Shc immunoprecipitates (as well as ±recombinant 5-ptase II, ie. PtII&BL (blank)) incubated with PtdIns[$^{32}$P]-3,4,5-P$_3$ under conditions where product formation was linear with time and the reaction mixture chromatographed on TLC(B)
Figure 6:
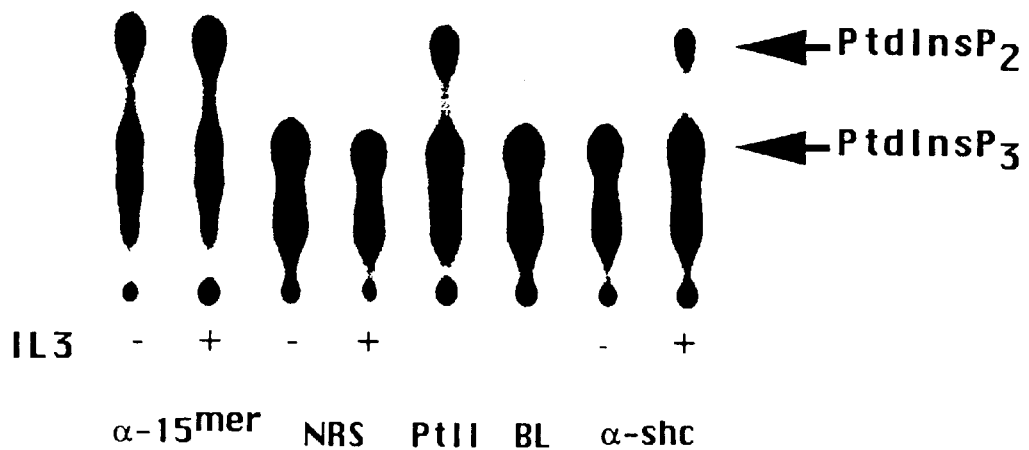

FIG. 6. p145 contains Ins-1,3,4,5-$P_4$ and PtdIns-3,4,5-$P_3$ 5-phosphatase activity. (A) 2×10$^7$ B6SUtA$_1$ cells were lysed and anti-15$^{mer}$, anti-Shc and NRS immunoprecipitates incubated with [$^3$H]Ins-1,3,4,5-$P_4$ under conditions where product formation was linear with time. Assays were also carried out ±recombinant 5-ptase II as controls. (B) 1/10th of anti-15$^{mer}$, NRS and anti-Shc immunoprecipitates (as well as ±recombinant 5-ptase II, ie. PtII&BL(blank))) were incubated with PtdIns[$^{32}$P]-3,4,5-$P_3$ under conditions where product formation was linear with time and the reaction mixture chromatographed on TLC (18).

Example 1

In preliminary studies aimed at purifying p145, immobilized GST fusion proteins containing the C-terminal (but not the N-terminal) SH3 domain of Grb2 were found to bind a prominent tyrosine phosphorylated protein doublet from B6SUtA$_1$ cell lysates that possessed the same mobility in SDS-gels as p145 (FIG. 1, lanes 1–6). Silver stained gels of Grb2-C-SH3 bound material indicated this doublet was prominent in terms of protein level as well, and most abundant in B6SUtA$_1$ cells (compared to MO7E, TF1, Ba/F3, DA-3 and 32D cells, data not shown). To determine if this Grb2-C-SH3 purified doublet was p145, B6SUtA$_1$ cell lysates were precleared with Grb2-C-SH3 beads and this dramatically depleted p145 in subsequent anti-Shc immunoprecipitates (FIG. 1, lane 7). Further proof was obtained by carrying out 2D-PAGE (P. H. O'Farrell, *J. Biol. Chem.* 250, 4007 (1975)) with the two preparations, followed by Western analysis, using anti-PY antibodies. An identical pattern of multiple spots was obtained in the 145-kD range, with isoelectric points ranging from 7.2 to 7.8.

Based on these findings, a purification protocol was devised as described above and two sequences were obtained from the purified protein; VPAEGVSSLNEMINP (SEQ.ID.NO:11), which was used to construct degenerate oligonucleotides, and DGSFLVR (SEQ.ID.NO:14), which strongly suggested the presence of an SH2 domain.

The full length cDNA for p145 was then cloned using a PCR based strategy and a B6SUtA$_1$ cDNA library as described above. The deduced 1190 amino acid sequence, possessing a theoretical pI of 7.75 (consistent with the 2D-gel results) revealed several interesting motifs (FIG. 2). Close to the amino terminus is the DGSFLVR (SEQ.ID.NO:14) sequence that is highly conserved among SH2 domains and, taken together with sequences surrounding this motif, suggests that p145 contains an SH2 domain most homologous, at the protein level, to those within Abl, Bruton's tyrosine kinase and Grb2. There are also two motifs, ie., INPNY (SEQ.ID.NO:9) and ENPLY (SEQ.ID.NO:10), that, in their phosphorylated forms, are theoretically capable of binding to PTB domains (P. Blaikie et al., *J. Biol. Chem.* 269, 32031 (1994); W. M. Kavanaugh et al., *Science* 268, 1177 (1995); I. Dikic et al.,*J. Biol. Chem.* 270, 15125 (1995); P. Bork and B. Margolis, *Cell* 80, 693 (1995); Z. Songyang et al., *J. Biol. Chem.* 270, 14863 (1995); A. Craparo et al.,*J. Biol. Chem.* 270, 15639 (1995); P. van der Geer and T. Pawson, *TIBS* 20, 277 (1995); A. G. Batzer et al.,*Mol. Cell. Biol.* 15, 4403 (1995); T. Trub et al., *J. Biol. Chem.* 270, 18205 (1995)). As well, several predicted proline-rich motifs are present near the carboxy terminus, including both class I (eg, PPSQPPLSP) (SEQ.ID.NO:15) and class II (eg, PVKPSR, (SEQ.ID.NO:16) PPLSPKK, (SEQ.ID.NO:17) PPLPVK (SEQ.ID.NO:18) (K. Alexandropoulos et al., *Proc. Natl. Acad. Sci. U.S.A.* 92, 3110 (1995); C. Schumacher et al., *J. Biol. Chem.* 270, 15341 (1995)). Most interestingly, there are 2 motifs that are highly conserved among 5-ptases, ie, WLGDLNYR (SEQ.ID.NO:19) and, 73 amino acids C-terminal to this, KYNLPSWCDRVLW (SEQ.ID.NO:20) (X. Zhang et al., *Proc. Natl. Acad. Sci. U.S.A.* 92,4853 (1995).

To identify tyrosine phosphorylated proteins that interact with p145 in vivo and to confirm p145 had been sequenced, lysates from B6SUtA$_1$ cells were immunoprecipitated with rabbit antiserum (ie, anti-15$^{mer}$) generated against the 15$^{mer}$ used for cloning E. Harlow and D. Lane, *Antibodies, A Laboratory Manual*. Cold Spring Harbor Laboratory, (1988)). Western analysis, using anti-PY, revealed, as expected, a 145-kD tyrosine phosphorylated doublet with an identical mobility in SDS gels to p145 (FIG. 4(A), lanes 1&2 and 5&6). Pre-immune serum did not immunoprecipitate this or any other tyrosine phosphorylated protein (FIG. 4(A), lanes 3&4). Moreover, anti-Shc immunoprecipitates of lysates precleared with anti-15$^{mer}$ no longer contained p145 (FIG. 4(A), lane 8). Interestingly, anti-15$^{mer}$ immunoprecipitates from lysates of IL-3-stimulated B6SUtA$_1$ cells consistently contained 50–55-kD and, occasionally, 75- and 97-kD tyrosine phosphorylated proteins (FIG. 4(A), lane 6). The 50–55-kD protein was shown to be Shc by treating anti-15$^{mer}$ immunoprecipitates with N-ethylmaleimide prior to SDS-PAGE to alter the mobility of the interfering IgH chain (M. R. Block et al., *Proc. Natl. Acad. Sci. U.S.A.* 85, 7852 (1988)), and then carrying out Western analysis with anti-PY (FIG. 4(B), upper panel) and anti-Shc antibodies (FIG. 4(B), lower panel).

To examine whether the expression of p145 was restricted to hemopoietic cells, Northern blot analysis was carried out with polyA purified RNA from various murine tissues. A 5.0-kb p145 transcript was found to be expressed in bone marrow, lung, spleen, muscle, testes and kidney, suggesting the presence of this protein in many cell types (FIG. 5).

Lastly, to determine if p145 was indeed a 5-ptase, lysates from B6SUtA$_1$ cells were immunoprecipitated with anti-15$^{mer}$, anti-Shc or normal rabbit serum (NRS) and the immunoprecipitates tested with various 5-ptase substrates (X. Zhang et al., *Proc. Natl. Acad. Sci. U.S.A.* 92,4853 (1995) and as described herein). As can be seen in FIG. 6(A), anti-15$^{mer}$, but not NRS, immunoprecipitates hydrolyzed [$^3$H]Ins-1,3,4,5-$P_4$ to [$^3$H]Ins-1,3,4-$P_3$. The product of the reaction was shown to be [$^3$H]Ins-1,3,4-$P_3$ by incubation with recombinant inositol-polyphosphate-1- and 4-phosphatases, followed by the separation of the bisphosphate product on Dowex-formate (Zhang, X., et al., Proc. .Natl.Acad.Sci.U.S.A. 92:4853–4856, 1995 and Jefferson, A. B. And Majerus, P. W. J. Biol. Chem. 270:9370–9377, 1955). In the presence of 3 mM EDTA, no hydrolysis of [$^3$H]Ins-1,3,4,5-$P_4$ was observed, suggesting that this 5-ptase is Mg$^{++}$-dependent. Interestingly, no significant difference in activity was observed between anti-15$^{mer}$ immunoprecipitates from stimulated and unstimulated cells. Moreover, as one might expect, anti-Shc immunoprecipitates possessed 5-ptase activity, but only after IL-3-stimulation. In addition, anti-15$^{mer}$, but not NRS, immunoprecipitates catalyzed the hydrolysis of PtdIns[$^{32}$P]-3,4,5-$P_3$, as did recombinant 5-ptase II (FIG. 6(B)). Once again there was no significant difference in activity between IL-3-stimulated and unstimulated cells and anti-Shc immunoprecipitates possessed 5-ptase activity only after cells were stimulated. This suggests that IL-3 affects only the localization of p145 and not its 5-ptase activity. In studies with other 5-ptase substrates, anti-15$^{mer}$ immunoprecipitates did not hydrolyse Ins-1,4,5-$P_3$ or PtdIns-4,5-$P_2$. P145 5-ptase substrate specificity is therefore distinct from that of other 5-ptases such as 5-ptase II, OCRL 5-ptase and a novel Mg$^{++}$-independent 5-ptase (Zhang, X., et al., Proc.Natl.Acad.Sci.U.S.A. 92:4853–4856, 1995; Jefferson, A. B. And Majerus, P. W. J. Biol. Chem. 270:9370–9377, 1955; and Jackson, S. P. Et al., EMBO J. 14:4490–4500, 1995).

Of the 5-ptases cloned to date (X. Zhang et al., *Proc. Natl. Acad. Sci. U.S.A.* 92,4853 (1995)), p145 is the first to possess an SH2 domain and to be tyrosine phosphorylated. Thus, p145 may play an important role in cytokine mediated signalling. In this regard, Cullen et al just reported that Ins-1,3,4,5-$P_4$, which is rapidly elevated in stimulated cells (I. R. Batty et al., *Biochem. J.* 232, 211 (1985)), binds to and stimulates a member of the GAP1 family (P. J. Cullen et al., *Nature* 376, 527 (1995)). It is therefore conceivable that p145, through its association with Shc, regulates Ras activity by hydrolyzing RasGAP bound Ins-1,3,4,5-$P_4$. In addition, with its multiple protein:protein interaction domains and its unique 5-ptase substrate specificity, p145 could play an important role in regulating Ca++-independent PKC activity (Toker, A., et al., J. Biol. Chem. 269:32358–32367, 1994), the emerging Akt/PKB pathway (Burgering, B. M. And Coffer, P. J., Nature 376:599–602, 1995) and other as yet uncharacterized PI-3-kinase stimulated cascades. In terms of its association with Shc, p145 may interact via its phosphorylated tyrosines with the SH2 of Shc, via its phosphorylated PTB recognition sequences with the PTB of Shc (as suggested by in vitro studies with the Shc-associated p145 in 3T3 cells (F. A. Norris and P. W. Majerus, *J. Biol. Chem.* 269, 8716 (1994)) and/or via its SH2 domain with $Y^{317}$ of Shc.

In summary, a tyrosine phosphorylated 145 kDa protein has been purified that associates with Shc in response to multiple cytokines from hemopoietic cells and shown it to be a novel, SH2-containing 5-ptase. Based on its properties it is suggested it be called SHIP for SH2-containing inositol-phosphatase.

Example 2

Cloning of hSHIP cDNA

Duplicate nitrocellulose (Schleicher & Schuell, Keene, N.H.) plaque-lifts were prepared from approximately 1×10$^6$ pfu of a custom-made MO7e/MO7-ER λgt11 cDNA library created from 10 μg of poly-A RNA (Clontech, Palo Alto, Calif.). Phage DNA bound to these membranes was denatured and hybridized (1.5×SSPE, 1% SDS, 1% Blotto, 0.25 mg/ml ssDNA) at 50° C. for 18 hours with non-overlapping, [$λ^{32}$P]dCTP randomly labeled cDNA fragments corresponding to either 1.5 kb of the 5'- most region (including the SH2 domain) or 1.1 kb of the central region (including the 5-Ptase domain) of murine SHIP. Probed membranes were washed three times with 0.5×SSC, 0.5% SDS at 50° C. for 30 minutes each. Membranes were exposed to Kodak X-Omat film (Rochester, N.Y.) and plaques which hybridized with both probes were identified and the phage isolated. Thirteen cDNA inserts were removed from "positive" phage by EcoRI digestion, gel purified, and subcloned into pBluescript KS+ for further analysis. One full-length cDNA, 4926 nt in length, was further digested with either PstI or XhoI and re-subcloned into pBluescript KS+ for automated ABI/Taq Polymerase sequencing (NAPS Unit, University of British Columbia, Vancouver, Canada) using standard T7 and T3 oligoprimers. Regions not overlapped by restriction fragments were sequenced using specific nucleotide oligoprimers. The human SHIP CDNA sequence is set out in FIG. 10 and in SEQ.ID.NO.12.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

I claim:

1. A purified and isolated SH2-containing inositol-phosphatase which comprises the amino acid sequence shown in SEQ.ID.NO.:2 or FIG. 2A.

2. A purified and isolated SH2-containing inositol-phosphatase which comprises the amino acid sequence shown in SEQ.ID.NO.:8 or FIG. 11.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 4040 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: murine (vii) IMMEDIATE SOURCE:
      (B) CLONE: mSHIP (ix) FEATURE:
      (A) NAME/KEY: CDS (B) LOCATION: 139..3693

(xi) SEQUENCE DESCRIPTION: SEQ ID NO:1:

```
CCCTGGTAGG AGCAGCAGAG GCAATTTCTG AGAGGCAACA GGCGGCAGGT CTCAGCCTAG      60

AGAGGGCCCT GAACTACTTT GCTGGAGTGT CCGTCCTGGG AGTGGCTGCT GACCCAGTCC     120

AGGAGACCCA TGCCTGCC ATG GTC CCT GGG TGG AAC CAT GGC AAC ATC ACC      171
                    Met Val Pro Gly Trp Asn His Gly Asn Ile Thr
                     1               5                      10

CGC TCC AAG GCA GAG GAG CTA CTT TCC AGA GCC GGC AAG GAC GGG AGC      219
Arg Ser Lys Ala Glu Glu Leu Leu Ser Arg Ala Gly Lys Asp Gly Ser
             15                  20                  25

TTC CTT GTG CGT GCC AGC GAG TCC ATC CCC CGG GCC TGC GCA CTC TGC      267
Phe Leu Val Arg Ala Ser Glu Ser Ile Pro Arg Ala Cys Ala Leu Cys
         30                  35                  40

GTG CTG TTC CGG AAT TGT GTT TAC ACT TAC AGG ATT CTG CCC AAT GAG      315
Val Leu Phe Arg Asn Cys Val Tyr Thr Tyr Arg Ile Leu Pro Asn Glu
     45                  50                  55

GAC GAT AAA TTC ACT GTT CAG GCA TCC GAA GGT GTC CCC ATG AGG TTC      363
Asp Asp Lys Phe Thr Val Gln Ala Ser Glu Gly Val Pro Met Arg Phe
 60                  65                  70                  75

TTC ACG AAG CTG GAC CAG CTC ATC GAC TTT TAC AAG AAG GAA AAC ATG      411
Phe Thr Lys Leu Asp Gln Leu Ile Asp Phe Tyr Lys Lys Glu Asn Met
                 80                  85                  90

GGG CTG GTG ACC CAC CTG CAG TAC CCC GTG CCC CTG GAG GAG GAG GAT      459
Gly Leu Val Thr His Leu Gln Tyr Pro Val Pro Leu Glu Glu Glu Asp
             95                 100                 105

GCT ATT GAT GAG GCT GAG GAG GAC ACT GAA AGT GTC ATG TCA CCA CCT      507
Ala Ile Asp Glu Ala Glu Glu Asp Thr Glu Ser Val Met Ser Pro Pro
         110                 115                 120

GAG CTG CCT CCC AGA AAC ATT CCT ATG TCT GCC GGG CCC AGC GAG GCC      555
Glu Leu Pro Pro Arg Asn Ile Pro Met Ser Ala Gly Pro Ser Glu Ala
     125                 130                 135

AAG GAC CTT CCT CTT GCA ACA GAG AAC CCC CGA GCC CCT GAG GTC ACC      603
Lys Asp Leu Pro Leu Ala Thr Glu Asn Pro Arg Ala Pro Glu Val Thr
140                 145                 150                 155

CGG CTG AGT CTC TCC GAG ACA CTG TTT CAG CGT CTA CAG AGC ATG GAT      651
Arg Leu Ser Leu Ser Glu Thr Leu Phe Gln Arg Leu Gln Ser Met Asp
                 160                 165                 170

ACC AGT GGG CTT CCC GAG GAG CAC CTG AAA GCC ATC CAG GAT TAT CTG      699
Thr Ser Gly Leu Pro Glu Glu His Leu Lys Ala Ile Gln Asp Tyr Leu
             175                 180                 185

AGC ACT CAG CTC CTC CTG GAT TCC GAC TTT TTG AAA ACG GGC TCC AGC      747
Ser Thr Gln Leu Leu Leu Asp Ser Asp Phe Leu Lys Thr Gly Ser Ser
         190                 195                 200

AAC CTC CCT CAC CTG AAG AAG CTG ATG TCA CTG CTC TGC AAG GAG CTC      795
Asn Leu Pro His Leu Lys Lys Leu Met Ser Leu Leu Cys Lys Glu Leu
     205                 210                 215

CAT GGG GAA GTC ATC AGG ACT CTG CCA TCC CTG GAG TCT CTG CAG AGG      843
His Gly Glu Val Ile Arg Thr Leu Pro Ser Leu Glu Ser Leu Gln Arg
220                 225                 230                 235

TTG TTT GAC CAA CAG CTC TCC CCA GGC CTT CGC CCA CGA CCT CAG GTG      891
Leu Phe Asp Gln Gln Leu Ser Pro Gly Leu Arg Pro Arg Pro Gln Val
                 240                 245                 250

CCC GGA GAG GCC AGT CCC ATC ACC ATG GTT GCC AAA CTC AGC CAA TTG      939
Pro Gly Glu Ala Ser Pro Ile Thr Met Val Ala Lys Leu Ser Gln Leu
             255                 260                 265

ACA AGT CTG CTG TCT TCC ATT GAA GAT AAG GTC AAG TCC TTG CTG CAC      987
Thr Ser Leu Leu Ser Ser Ile Glu Asp Lys Val Lys Ser Leu Leu His
         270                 275                 280
```

```
GAG GGC TCA GAA TCT ACC AAC AGG CGT TCC CTT ATC CCT CCG GTC ACC    1035
Glu Gly Ser Glu Ser Thr Asn Arg Arg Ser Leu Ile Pro Pro Val Thr
    285                 290                 295

TTT GAG GTG AAG TCA GAG TCC CTG GGC ATT CCT CAG AAA ATG CAT CTC    1083
Phe Glu Val Lys Ser Glu Ser Leu Gly Ile Pro Gln Lys Met His Leu
300                 305                 310                 315

AAA GTG GAC GTT GAG TCT GGG AAA CTG ATC GTT AAG AAG TCC AAG GAT    1131
Lys Val Asp Val Glu Ser Gly Lys Leu Ile Val Lys Lys Ser Lys Asp
                320                 325                 330

GGT TCT GAG GAC AAG TTC TAC AGC CAC AAA AAA ATC CTG CAG CTC ATT    1179
Gly Ser Glu Asp Lys Phe Tyr Ser His Lys Lys Ile Leu Gln Leu Ile
                335                 340                 345

AAG TCC CAG AAG TTT CTA AAC AAG TTG GTG ATT TTG GTG GAG ACG GAG    1227
Lys Ser Gln Lys Phe Leu Asn Lys Leu Val Ile Leu Val Glu Thr Glu
            350                 355                 360

AAG GAG AAA ATC CTG AGG AAG GAA TAT GTT TTT GCT GAC TCT AAG AAA    1275
Lys Glu Lys Ile Leu Arg Lys Glu Tyr Val Phe Ala Asp Ser Lys Lys
365                 370                 375

AGA GAA GGC TTC TGT CAA CTC CTG CAG CAG ATG AAG AAC AAG CAT TCG    1323
Arg Glu Gly Phe Cys Gln Leu Leu Gln Gln Met Lys Asn Lys His Ser
380                 385                 390                 395

GAG CAG CCA GAG CCT GAC ATG ATC ACC ATC TTC ATT GGC ACT TGG AAC    1371
Glu Gln Pro Glu Pro Asp Met Ile Thr Ile Phe Ile Gly Thr Trp Asn
                400                 405                 410

ATG GGT AAT GCA CCC CCT CCC AAG AAG ATC ACG TCC TGG TTT CTC TCC    1419
Met Gly Asn Ala Pro Pro Pro Lys Lys Ile Thr Ser Trp Phe Leu Ser
                415                 420                 425

AAG GGG CAG GGA AAG ACA CGG GAC GAC TCT GCT GAC TAC ATC CCC CAT    1467
Lys Gly Gln Gly Lys Thr Arg Asp Asp Ser Ala Asp Tyr Ile Pro His
            430                 435                 440

GAC ATC TAT GTG ATT GGC ACC CAG GAG GAT CCC CTT GGA GAG AAG GAG    1515
Asp Ile Tyr Val Ile Gly Thr Gln Glu Asp Pro Leu Gly Glu Lys Glu
            445                 450                 455

TGG CTG GAG CTA CTC AGG CAC TCC CTG CAA GAA GTC ACC AGC ATG ACA    1563
Trp Leu Glu Leu Leu Arg His Ser Leu Gln Glu Val Thr Ser Met Thr
460                 465                 470                 475

TTT AAA ACA GTT GCC ATC CAC ACC CTC TGG AAC ATT CGC ATA GTG GTG    1611
Phe Lys Thr Val Ala Ile His Thr Leu Trp Asn Ile Arg Ile Val Val
                480                 485                 490

CTT GCC AAG CCA GAG CAT GAG AAT CGG ATC AGC CAT ATC TGC ACT GAC    1659
Leu Ala Lys Pro Glu His Glu Asn Arg Ile Ser His Ile Cys Thr Asp
                495                 500                 505

AAC GTG AAG ACA GGC ATC GCC AAC ACC CTG GGA AAC AAG GGA GCA GTG    1707
Asn Val Lys Thr Gly Ile Ala Asn Thr Leu Gly Asn Lys Gly Ala Val
            510                 515                 520

GGA GTG TCC TTC ATG TTC AAT GGA ACC TCC TTG GGG TTC GTC AAC AGC    1755
Gly Val Ser Phe Met Phe Asn Gly Thr Ser Leu Gly Phe Val Asn Ser
            525                 530                 535

CAC TTG ACT TCT GGA AGT GAA AAA AAG CTC AGG AGA AAT CAA AAC TAT    1803
His Leu Thr Ser Gly Ser Glu Lys Lys Leu Arg Arg Asn Gln Asn Tyr
540                 545                 550                 555

ATG AAC ATC CTG CGG TTC CTG GCC CTG GGA GAC AAG AAG CTA AGC CCA    1851
Met Asn Ile Leu Arg Phe Leu Ala Leu Gly Asp Lys Lys Leu Ser Pro
                560                 565                 570

TTT AAC ATC ACC CAC CGC TTC ACC CAC CTC TTC TGG CTT GGG GAT CTC    1899
Phe Asn Ile Thr His Arg Phe Thr His Leu Phe Trp Leu Gly Asp Leu
                575                 580                 585

AAC TAC CGC GTG GAG CTG CCC ACT TGG GAG GCA GAG GCC ATC ATC CAG    1947
Asn Tyr Arg Val Glu Leu Pro Thr Trp Glu Ala Glu Ala Ile Ile Gln
```

-continued

```
            590                     595                     600
AAG ATC AAG CAA CAG CAG TAT TCA GAC CTT CTG GCC CAC GAC CAA CTG   1995
Lys Ile Lys Gln Gln Gln Tyr Ser Asp Leu Leu Ala His Asp Gln Leu
        605                     610                     615

CTC CTG GAG AGG AAG GAC CAG AAG GTC TTC CTG CAC TTT GAG GAG GAA   2043
Leu Leu Glu Arg Lys Asp Gln Lys Val Phe Leu His Phe Glu Glu Glu
620                     625                     630                     635

GAG ATC ACC TTC GCC CCC ACC TAT CGA TTT GAA AGA CTG ACC CGG GAC   2091
Glu Ile Thr Phe Ala Pro Thr Tyr Arg Phe Glu Arg Leu Thr Arg Asp
                        640                     645                     650

AAG TAT GCA TAC ACG AAG CAG AAA GCA ACA GGG ATG AAG TAC AAC TTG   2139
Lys Tyr Ala Tyr Thr Lys Gln Lys Ala Thr Gly Met Lys Tyr Asn Leu
            655                     660                     665

CCG TCC TGG TGC GAC CGA GTC CTC TGG AAG TCT TAC CCG CTG GTG CAT   2187
Pro Ser Trp Cys Asp Arg Val Leu Trp Lys Ser Tyr Pro Leu Val His
        670                     675                     680

GTG GTC TGT CAG TCC TAT GGC AGT ACC AGT GAC ATC ATG ACG AGT GAC   2235
Val Val Cys Gln Ser Tyr Gly Ser Thr Ser Asp Ile Met Thr Ser Asp
685                     690                     695

CAC AGC CCT GTC TTT GCC ACG TTT GAA GCA GGA GTC ACA TCT CAA TTC   2283
His Ser Pro Val Phe Ala Thr Phe Glu Ala Gly Val Thr Ser Gln Phe
700                     705                     710                     715

GTC TCC AAG AAT GGT CCT GGC ACT GTA GAT AGC CAA GGG CAG ATC GAG   2331
Val Ser Lys Asn Gly Pro Gly Thr Val Asp Ser Gln Gly Gln Ile Glu
                        720                     725                     730

TTT CTT GCA TGC TAC GCC ACA CTG AAG ACC AAG TCC CAG ACT AAG TTC   2379
Phe Leu Ala Cys Tyr Ala Thr Leu Lys Thr Lys Ser Gln Thr Lys Phe
            735                     740                     745

TAC TTG GAG TTC CAC TCA AGC TGC TTA GAG AGT TTT GTC AAG AGT CAG   2427
Tyr Leu Glu Phe His Ser Ser Cys Leu Glu Ser Phe Val Lys Ser Gln
        750                     755                     760

GAA GGA GAG AAT GAA GAG GGA AGT GAA GGA GAG CTG GTG GTA CGG TTT   2475
Glu Gly Glu Asn Glu Glu Gly Ser Glu Gly Glu Leu Val Val Arg Phe
765                     770                     775

GGA GAG ACT CTT CCC AAG CTA AAG CCC ATT ATC TCT GAC CCC GAG TAC   2523
Gly Glu Thr Leu Pro Lys Leu Lys Pro Ile Ile Ser Asp Pro Glu Tyr
780                     785                     790                     795

TTA CTG GAC CAG CAT ATC CTG ATC AGC ATT AAA TCC TCT GAC AGT GAC   2571
Leu Leu Asp Gln His Ile Leu Ile Ser Ile Lys Ser Ser Asp Ser Asp
                        800                     805                     810

GAG TCC TAT GGT GAA GGC TGC ATT GCC CTT CGC TTG GAG ACC ACA GAG   2619
Glu Ser Tyr Gly Glu Gly Cys Ile Ala Leu Arg Leu Glu Thr Thr Glu
            815                     820                     825

GCT CAG CAT CCT ATC TAC ACG CCT CTC ACC CAC CAT GGG GAG ATG ACT   2667
Ala Gln His Pro Ile Tyr Thr Pro Leu Thr His His Gly Glu Met Thr
        830                     835                     840

GGC CAC TTC AGG GGA GAG ATT AAG CTG CAG ACC TCC CAG GGC AAG ATG   2715
Gly His Phe Arg Gly Glu Ile Lys Leu Gln Thr Ser Gln Gly Lys Met
845                     850                     855

AGG GAG AAG CTC TAT GAC TTT GTG AAG ACA GAG CGG GAT GAA TCC AGT   2763
Arg Glu Lys Leu Tyr Asp Phe Val Lys Thr Glu Arg Asp Glu Ser Ser
860                     865                     870                     875

GGA ATG AAA TGC TTG AAG AAC CTC ACC AGC CAT GAC CCT ATG AGG CAA   2811
Gly Met Lys Cys Leu Lys Asn Leu Thr Ser His Asp Pro Met Arg Gln
                        880                     885                     890

TGG GAG CCT TCT GGC AGG GTC CCT GCA TGT GGT GTC TCC AGC CTC AAT   2859
Trp Glu Pro Ser Gly Arg Val Pro Ala Cys Gly Val Ser Ser Leu Asn
            895                     900                     905

GAG ATG ATC AAT CCA AAC TAC ATT GGT ATG GGG CCT TTT GGA CAG CCC   2907
```

```
Glu Met Ile Asn Pro Asn Tyr Ile Gly Met Gly Pro Phe Gly Gln Pro
    910                 915                 920

CTG CAT GGG AAA TCA ACC CTG TCC CCA GAT CAG CAA CTC ACA GCT TGG        2955
Leu His Gly Lys Ser Thr Leu Ser Pro Asp Gln Gln Leu Thr Ala Trp
    925                 930                 935

AGT TAT GAC CAG CTA CCC AAA GAC TCC TCC CTG GGG CCT GGG AGG GGG        3003
Ser Tyr Asp Gln Leu Pro Lys Asp Ser Ser Leu Gly Pro Gly Arg Gly
940                 945                 950                 955

GAG GGT CCT CCA ACC CCT CCC TCC CAA CCA CCT CTG TCG CCA AAG AAG        3051
Glu Gly Pro Pro Thr Pro Pro Ser Gln Pro Pro Leu Ser Pro Lys Lys
                960                 965                 970

TTT TCA TCT TCC ACA ACC AAC CGA GGT CCC TGC CCC AGG GTG CAA GAG        3099
Phe Ser Ser Ser Thr Thr Asn Arg Gly Pro Cys Pro Arg Val Gln Glu
            975                 980                 985

GCA AGA CCT GGG GAT CTG GGA AAG GTG GAA GCT CTG CTC CAG GAG GAC        3147
Ala Arg Pro Gly Asp Leu Gly Lys Val Glu Ala Leu Leu Gln Glu Asp
        990                 995                 1000

CTG CTG CTG ACG AAG CCC GAG ATG TTT GAG AAC CCA CTG TAT GGA TCC        3195
Leu Leu Leu Thr Lys Pro Glu Met Phe Glu Asn Pro Leu Tyr Gly Ser
    1005                1010                1015

GTG AGT TCC TTC CCT AAG CTG GTG CCC AGG AAA GAG CAG GAG TCT CCC        3243
Val Ser Ser Phe Pro Lys Leu Val Pro Arg Lys Glu Gln Glu Ser Pro
1020                1025                1030                1035

AAG ATG CTG CGG AAG GAG CCC CCG CCC TGT CCA GAC CCA GGA ATC TCA        3291
Lys Met Leu Arg Lys Glu Pro Pro Pro Cys Pro Asp Pro Gly Ile Ser
                1040                1045                1050

TCA CCC AGC ATC GTG CTC CCC AAA GCC CAA GAG GTG GAG AGT GTC AAG        3339
Ser Pro Ser Ile Val Leu Pro Lys Ala Gln Glu Val Glu Ser Val Lys
            1055                1060                1065

GGG ACA AGC AAA CAG GCC CCT GTG CCT GTC CTT GGC CCC ACA CCC CGG        3387
Gly Thr Ser Lys Gln Ala Pro Val Pro Val Leu Gly Pro Thr Pro Arg
        1070                1075                1080

ATC CGC TCC TTT ACC TGT TCT TCT TCT GCT GAG GGC AGA ATG ACC AGT        3435
Ile Arg Ser Phe Thr Cys Ser Ser Ser Ala Glu Gly Arg Met Thr Ser
    1085                1090                1095

GGG GAC AAG AGC CAA GGG AAG CCC AAG GCC TCA GCC AGT TCC CAA GCC        3483
Gly Asp Lys Ser Gln Gly Lys Pro Lys Ala Ser Ala Ser Ser Gln Ala
1100                1105                1110                1115

CCA GTG CCA GTC AAG AGG CCT GTC AAG CCT TCC AGG TCA GAA ATG AGC        3531
Pro Val Pro Val Lys Arg Pro Val Lys Pro Ser Arg Ser Glu Met Ser
                1120                1125                1130

CAG CAG ACA ACA CCC ATC CCA GCT CCA CGG CCA CCC CTG CCA GTC AAG        3579
Gln Gln Thr Thr Pro Ile Pro Ala Pro Arg Pro Pro Leu Pro Val Lys
            1135                1140                1145

AGT CCT GCT GTC CTG CAG CTG CAA CAT TCC AAA GGC AGA GAC TAC CGT        3627
Ser Pro Ala Val Leu Gln Leu Gln His Ser Lys Gly Arg Asp Tyr Arg
        1150                1155                1160

GAC AAC ACA GAA CTC CCC CAC CAT GGC AAG CAC CGC CAA GAG GAG GGG        3675
Asp Asn Thr Glu Leu Pro His His Gly Lys His Arg Gln Glu Glu Gly
    1165                1170                1175

CTG CTT GGC AGG ACT GCC ATGCAGTGAG CTGCTGGTGA TCGGAGCCTG              3723
Leu Leu Gly Arg Thr Ala
1180                1185

GAGGAACAGC ACAAAGCAGA CCTGCGACCT CTCTCAGGAT GCCTCTCTCA GGATGCCTCT      3783

TGGAGGACCT CCTGCTAGCT CTTCTTGCCT AGCTTCAAGT CCCAGGCTGT GTATTTTTTT      3843

TCAGGAAACG GCCTCACTTC TCTGTGGTCC AAGAAGTGTG CTGCTGGCTG CCACACTGTG      3903

CGGCAGATGC TAAAGCTGGA TGACAAACGC ACGCCATACA GACAGCAGAC AGCGGCACTG      3963
```

```
GGTCTCAGAA CTTGGATTCC TGGGCCTTCT TCCAGTCGCC GTTTTAAAGA AAGGAACTAA    4023

CGGAGCTGCT CATCCGA                                                   4040
```

(2) INFORMATION FOR SEQ ID NO:2:

(i) SEQUENCE CHARACTERISTICS:
        (A) LENGTH: 1185 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Pro Gly Trp Asn His Gly Asn Ile Thr Arg Ser Lys Ala Glu
  1               5                  10                  15

Glu Leu Leu Ser Arg Ala Gly Lys Asp Gly Ser Phe Leu Val Arg Ala
             20                  25                  30

Ser Glu Ser Ile Pro Arg Ala Cys Ala Leu Cys Val Leu Phe Arg Asn
         35                  40                  45

Cys Val Tyr Thr Tyr Arg Ile Leu Pro Asn Glu Asp Asp Lys Phe Thr
 50                  55                  60

Val Gln Ala Ser Glu Gly Val Pro Met Arg Phe Phe Thr Lys Leu Asp
 65                  70                  75                  80

Gln Leu Ile Asp Phe Tyr Lys Lys Glu Asn Met Gly Leu Val Thr His
             85                  90                  95

Leu Gln Tyr Pro Val Pro Leu Glu Glu Glu Asp Ala Ile Asp Glu Ala
            100                 105                 110

Glu Glu Asp Thr Glu Ser Val Met Ser Pro Glu Leu Pro Pro Arg
            115                 120                 125

Asn Ile Pro Met Ser Ala Gly Pro Ser Glu Ala Lys Asp Leu Pro Leu
130                 135                 140

Ala Thr Glu Asn Pro Arg Ala Pro Glu Val Thr Arg Leu Ser Leu Ser
145                 150                 155                 160

Glu Thr Leu Phe Gln Arg Leu Gln Ser Met Asp Thr Ser Gly Leu Pro
                165                 170                 175

Glu Glu His Leu Lys Ala Ile Gln Asp Tyr Leu Ser Thr Gln Leu Leu
            180                 185                 190

Leu Asp Ser Asp Phe Leu Lys Thr Gly Ser Ser Asn Leu Pro His Leu
        195                 200                 205

Lys Lys Leu Met Ser Leu Leu Cys Lys Glu Leu His Gly Glu Val Ile
    210                 215                 220

Arg Thr Leu Pro Ser Leu Glu Ser Leu Gln Arg Leu Phe Asp Gln Gln
225                 230                 235                 240

Leu Ser Pro Gly Leu Arg Pro Arg Pro Gln Val Pro Gly Glu Ala Ser
                245                 250                 255

Pro Ile Thr Met Val Ala Lys Leu Ser Gln Leu Thr Ser Leu Leu Ser
            260                 265                 270

Ser Ile Glu Asp Lys Val Lys Ser Leu Leu His Glu Gly Ser Glu Ser
        275                 280                 285

Thr Asn Arg Arg Ser Leu Ile Pro Pro Val Thr Phe Glu Val Lys Ser
    290                 295                 300

Glu Ser Leu Gly Ile Pro Gln Lys Met His Leu Lys Val Asp Val Glu
305                 310                 315                 320

Ser Gly Lys Leu Ile Val Lys Lys Ser Asp Gly Ser Glu Asp Lys
                325                 330                 335
```

```
Phe Tyr Ser His Lys Lys Ile Leu Gln Leu Ile Lys Ser Gln Lys Phe
                340                 345                 350

Leu Asn Lys Leu Val Ile Leu Val Glu Thr Glu Lys Glu Lys Ile Leu
            355                 360                 365

Arg Lys Glu Tyr Val Phe Ala Asp Ser Lys Arg Glu Gly Phe Cys
        370                 375                 380

Gln Leu Leu Gln Gln Met Lys Asn Lys His Ser Glu Gln Pro Glu Pro
385                 390                 395                 400

Asp Met Ile Thr Ile Phe Ile Gly Thr Trp Asn Met Gly Asn Ala Pro
                405                 410                 415

Pro Pro Lys Lys Ile Thr Ser Trp Phe Leu Ser Lys Gly Gln Gly Lys
                420                 425                 430

Thr Arg Asp Asp Ser Ala Asp Tyr Ile Pro His Asp Ile Tyr Val Ile
            435                 440                 445

Gly Thr Gln Glu Asp Pro Leu Gly Glu Lys Glu Trp Leu Glu Leu Leu
        450                 455                 460

Arg His Ser Leu Gln Glu Val Thr Ser Met Thr Phe Lys Thr Val Ala
465                 470                 475                 480

Ile His Thr Leu Trp Asn Ile Arg Ile Val Leu Ala Lys Pro Glu
                485                 490                 495

His Glu Asn Arg Ile Ser His Ile Cys Thr Asp Asn Val Lys Thr Gly
            500                 505                 510

Ile Ala Asn Thr Leu Gly Asn Lys Gly Ala Val Gly Val Ser Phe Met
        515                 520                 525

Phe Asn Gly Thr Ser Leu Gly Phe Val Asn Ser His Leu Thr Ser Gly
        530                 535                 540

Ser Glu Lys Lys Leu Arg Arg Asn Gln Asn Tyr Met Asn Ile Leu Arg
545                 550                 555                 560

Phe Leu Ala Leu Gly Asp Lys Lys Leu Ser Pro Phe Asn Ile Thr His
                565                 570                 575

Arg Phe Thr His Leu Phe Trp Leu Gly Asp Leu Asn Tyr Arg Val Glu
            580                 585                 590

Leu Pro Thr Trp Glu Ala Glu Ala Ile Ile Gln Lys Ile Lys Gln Gln
        595                 600                 605

Gln Tyr Ser Asp Leu Leu Ala His Asp Gln Leu Leu Glu Arg Lys
        610                 615                 620

Asp Gln Lys Val Phe Leu His Phe Glu Glu Glu Ile Thr Phe Ala
625                 630                 635                 640

Pro Thr Tyr Arg Phe Glu Arg Leu Thr Arg Asp Lys Tyr Ala Tyr Thr
                645                 650                 655

Lys Gln Lys Ala Thr Gly Met Lys Tyr Asn Leu Pro Ser Trp Cys Asp
                660                 665                 670

Arg Val Leu Trp Lys Ser Tyr Pro Leu Val His Val Val Cys Gln Ser
            675                 680                 685

Tyr Gly Ser Thr Ser Asp Ile Met Thr Ser Asp His Ser Pro Val Phe
        690                 695                 700

Ala Thr Phe Glu Ala Gly Val Thr Ser Gln Phe Val Ser Lys Asn Gly
705                 710                 715                 720

Pro Gly Thr Val Asp Ser Gln Gly Gln Ile Glu Phe Leu Ala Cys Tyr
                725                 730                 735

Ala Thr Leu Lys Thr Lys Ser Gln Thr Lys Phe Tyr Leu Glu Phe His
            740                 745                 750

Ser Ser Cys Leu Glu Ser Phe Val Lys Ser Gln Glu Gly Glu Asn Glu
```

-continued

```
                755                 760                 765
Glu Gly Ser Glu Gly Glu Leu Val Arg Phe Gly Glu Thr Leu Pro
770                 775                 780
Lys Leu Lys Pro Ile Ile Ser Asp Pro Glu Tyr Leu Leu Asp Gln His
785                 790                 795                 800
Ile Leu Ile Ser Ile Lys Ser Ser Asp Ser Asp Glu Ser Tyr Gly Glu
                    805                 810                 815
Gly Cys Ile Ala Leu Arg Leu Glu Thr Thr Glu Ala Gln His Pro Ile
            820                 825                 830
Tyr Thr Pro Leu Thr His His Gly Glu Met Thr Gly His Phe Arg Gly
            835                 840                 845
Glu Ile Lys Leu Gln Thr Ser Gln Gly Lys Met Arg Glu Lys Leu Tyr
            850                 855                 860
Asp Phe Val Lys Thr Glu Arg Asp Glu Ser Ser Gly Met Lys Cys Leu
865                 870                 875                 880
Lys Asn Leu Thr Ser His Asp Pro Met Arg Gln Trp Glu Pro Ser Gly
                    885                 890                 895
Arg Val Pro Ala Cys Gly Val Ser Ser Leu Asn Glu Met Ile Asn Pro
            900                 905                 910
Asn Tyr Ile Gly Met Gly Pro Phe Gly Gln Pro Leu His Gly Lys Ser
            915                 920                 925
Thr Leu Ser Pro Asp Gln Gln Leu Thr Ala Trp Ser Tyr Asp Gln Leu
            930                 935                 940
Pro Lys Asp Ser Ser Leu Gly Pro Gly Arg Gly Glu Gly Pro Pro Thr
945                 950                 955                 960
Pro Pro Ser Gln Pro Pro Leu Ser Pro Lys Lys Phe Ser Ser Ser Thr
                    965                 970                 975
Thr Asn Arg Gly Pro Cys Pro Arg Val Gln Glu Ala Arg Pro Gly Asp
            980                 985                 990
Leu Gly Lys Val Glu Ala Leu Gln Glu Asp Leu Leu Thr Lys
            995                 1000                1005
Pro Glu Met Phe Glu Asn Pro Leu Tyr Gly Ser Val Ser Ser Phe Pro
            1010                1015                1020
Lys Leu Val Pro Arg Lys Glu Gln Glu Ser Pro Lys Met Leu Arg Lys
1025                1030                1035                1040
Glu Pro Pro Pro Cys Pro Asp Pro Gly Ile Ser Ser Pro Ser Ile Val
                    1045                1050                1055
Leu Pro Lys Ala Gln Glu Val Glu Ser Val Lys Gly Thr Ser Lys Gln
            1060                1065                1070
Ala Pro Val Pro Val Leu Gly Pro Thr Pro Arg Ile Arg Ser Phe Thr
            1075                1080                1085
Cys Ser Ser Ser Ala Glu Gly Arg Met Thr Ser Gly Asp Lys Ser Gln
            1090                1095                1100
Gly Lys Pro Lys Ala Ser Ala Ser Ser Gln Ala Pro Val Pro Val Lys
1105                1110                1115                1120
Arg Pro Val Lys Pro Ser Arg Ser Glu Met Ser Gln Gln Thr Thr Pro
                    1125                1130                1135
Ile Pro Ala Pro Arg Pro Pro Leu Pro Val Lys Ser Pro Ala Val Leu
            1140                1145                1150
Gln Leu Gln His Ser Lys Gly Arg Asp Tyr Arg Asp Asn Thr Glu Leu
            1155                1160                1165
Pro His His Gly Lys His Arg Gln Glu Glu Gly Leu Leu Gly Arg Thr
            1170                1175                1180
```

Ala
1185

(2) INFORMATION FOR SEQ ID NO:3:

(i) SEQUENCE CHARACTERISTICS:
        (A) LENGTH: 3031 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens
        (B) STRAIN: Shc Proteins (ix) FEATURE:
        (A) NAME/KEY: CDS
        (B) LOCATION: 82..1503

(xi) SEQUENCE DESCRIPTION: SEQ ID NO:3:

```
GCGGTAACCT AAGCTGGCAG TGGCGTGATC CGGCACCAAA TCGGCCCGCG GTGCGTGCGG         60

AGACTCCATG AGGCCCTGGA C ATG AAC AAG CTG AGT GGA GGC GGC GGG CGC         111
                       Met Asn Lys Leu Ser Gly Gly Gly Gly Arg
                        1               5                   10

AGG ACT CGG GTG GAA GGG GGC CAG CTT GGG GGC GAG GAG TGG ACC CGC         159
Arg Thr Arg Val Glu Gly Gly Gln Leu Gly Gly Glu Glu Trp Thr Arg
             15                  20                  25

CAC GGG AGC TTT GTC AAT AAG CCC ACG CGG GGC TGG CTG CAT CCC AAC         207
His Gly Ser Phe Val Asn Lys Pro Thr Arg Gly Trp Leu His Pro Asn
         30                  35                  40

GAC AAA GTC ATG GGA CCC GGG GTT TCC TAC TTG GTT CGG TAC ATG GGT         255
Asp Lys Val Met Gly Pro Gly Val Ser Tyr Leu Val Arg Tyr Met Gly
     45                  50                  55

TGT GTG GAG GTC CTC CAG TCA ATG CGT GCC CTG GAC TTC AAC ACC CGG         303
Cys Val Glu Val Leu Gln Ser Met Arg Ala Leu Asp Phe Asn Thr Arg
 60                  65                  70

ACT CAG GTC ACC AGG GAG GCC ATC AGT CTG GTG TGT GAG GCT GTG CCG         351
Thr Gln Val Thr Arg Glu Ala Ile Ser Leu Val Cys Glu Ala Val Pro
 75                  80                  85                  90

GGT GCT AAG GGG GCG ACA AGG AGG AGA AAG CCC TGT AGC CGC CCG CTC         399
Gly Ala Lys Gly Ala Thr Arg Arg Arg Lys Pro Cys Ser Arg Pro Leu
                 95                 100                 105

AGC TCT ATC CTG GGG AGG AGT AAC CTG AAA TTT GCT GGA ATG CCA ATC         447
Ser Ser Ile Leu Gly Arg Ser Asn Leu Lys Phe Ala Gly Met Pro Ile
             110                 115                 120

ACT CTC ACC GTC TCC ACC AGC AGC CTC AAC CTC ATG GCC GCA GAC TGC         495
Thr Leu Thr Val Ser Thr Ser Ser Leu Asn Leu Met Ala Ala Asp Cys
                 125                 130                 135

AAA CAG ATC ATC GCC AAC CAC CAC ATG CAA TCT ATC TCA TTT GCA TCC         543
Lys Gln Ile Ile Ala Asn His His Met Gln Ser Ile Ser Phe Ala Ser
 140                 145                 150

GGC GGG GAT CCG GAC ACA GCC GAG TAT GTC GCC TAT GTT GCC AAA GAC         591
Gly Gly Asp Pro Asp Thr Ala Glu Tyr Val Ala Tyr Val Ala Lys Asp
155                 160                 165                 170

CCT GTG AAT CAG AGA GCC TGC CAC ATT CTG GAG TGT CCC GAA GGG CTT         639
Pro Val Asn Gln Arg Ala Cys His Ile Leu Glu Cys Pro Glu Gly Leu
                 175                 180                 185

GCC CAG GAT GTC ATC AGC ACC ATT GGC CAG GCC TTC GAG TTG CGC TTC         687
Ala Gln Asp Val Ile Ser Thr Ile Gly Gln Ala Phe Glu Leu Arg Phe
             190                 195                 200
```

```
AAA CAA TAC CTC AGG AAC CCA CCC AAA CTG GTC ACC CCT CAT GAC AGG      735
Lys Gln Tyr Leu Arg Asn Pro Pro Lys Leu Val Thr Pro His Asp Arg
        205                 210                 215

ATG GCT GGC TTT GAT GGC TCA GCA TGG GAT GAG GAG GAG GAA GAG CCA      783
Met Ala Gly Phe Asp Gly Ser Ala Trp Asp Glu Glu Glu Glu Glu Pro
    220                 225                 230

CCT GAC CAT CAG TAC TAT AAT GAC TTC CCG GGG AAG GAA CCC CCC TTG      831
Pro Asp His Gln Tyr Tyr Asn Asp Phe Pro Gly Lys Glu Pro Pro Leu
235                 240                 245                 250

GGG GGG GTG GTA GAC ATG AGG CTT CGG GAA GGA GCC GCT CCA GGG GCT      879
Gly Gly Val Val Asp Met Arg Leu Arg Glu Gly Ala Ala Pro Gly Ala
                255                 260                 265

GCT CGA CCC ACT GCA CCC AAT GCC CAG ACC CCC AGC CAC TTG GGA GCT      927
Ala Arg Pro Thr Ala Pro Asn Ala Gln Thr Pro Ser His Leu Gly Ala
            270                 275                 280

ACA TTG CCT GTA GGA CAG CCT GTT GGG GGA GAT CCA GAA GTC CGC AAA      975
Thr Leu Pro Val Gly Gln Pro Val Gly Gly Asp Pro Glu Val Arg Lys
        285                 290                 295

CAG ATG CCA CCT CCA CCA CCC TGT CCA GGC AGA GAG CTT TTT GAT GAT     1023
Gln Met Pro Pro Pro Pro Pro Cys Pro Gly Arg Glu Leu Phe Asp Asp
    300                 305                 310

CCC TCC TAT GTC AAC GTC CAG AAC CTA GAC AAG GCC CGG CAA GCA GTG     1071
Pro Ser Tyr Val Asn Val Gln Asn Leu Asp Lys Ala Arg Gln Ala Val
315                 320                 325                 330

GGT GGT GCT GGG CCC CCC AAT CCT GCT ATC AAT GGC AGT GCA CCC CGG     1119
Gly Gly Ala Gly Pro Pro Asn Pro Ala Ile Asn Gly Ser Ala Pro Arg
                335                 340                 345

GAC CTG TTT GAC ATG AAG CCC TTC GAA GAT GCT CTT CGG GTG CCT CCA     1167
Asp Leu Phe Asp Met Lys Pro Phe Glu Asp Ala Leu Arg Val Pro Pro
            350                 355                 360

CCT CCC CAG TCG GTG TCC ATG GCT GAG CAG CTC CGA GGG GAG CCC TGG     1215
Pro Pro Gln Ser Val Ser Met Ala Glu Gln Leu Arg Gly Glu Pro Trp
        365                 370                 375

TTC CAT GGG AAG CTG AGC CGG CGG GAG GCT GAG GCA CTG CTG CAG CTC     1263
Phe His Gly Lys Leu Ser Arg Arg Glu Ala Glu Ala Leu Leu Gln Leu
    380                 385                 390

AAT GGG GAC TTC TTG GTA CGG GAG AGC ACG ACC ACA CCT GGC CAG TAT     1311
Asn Gly Asp Phe Leu Val Arg Glu Ser Thr Thr Thr Pro Gly Gln Tyr
395                 400                 405                 410

GTG CTC ACT GGC TTG CAG AGT GGG CAG CCT AAG CAT TTG CTA CTG GTG     1359
Val Leu Thr Gly Leu Gln Ser Gly Gln Pro Lys His Leu Leu Leu Val
                415                 420                 425

GAC CCT GAG GGT GTG GTT CGG ACT AAG GAT CAC CGC TTT GAA AGT GTC     1407
Asp Pro Glu Gly Val Val Arg Thr Lys Asp His Arg Phe Glu Ser Val
            430                 435                 440

AGT CAC CTT ATC AGC TAC CAC ATG GAC AAT CAC TTG CCC ATC ATC TCT     1455
Ser His Leu Ile Ser Tyr His Met Asp Asn His Leu Pro Ile Ile Ser
        445                 450                 455

GCG GGC AGC GAA CTG TGT CTA CAG CAA CCT GTG GAG CGG AAA CTG TGA     1503
Ala Gly Ser Glu Leu Cys Leu Gln Gln Pro Val Glu Arg Lys Leu  *
    460                 465                 470

TCTGCCCTAG CGCTCTCTTC CAGAAGATGC CCTCCAATCC TTTCCACCCT ATTCCCTAAC   1563

TCTCGGGACC TCGTTTGGGA GTGTTCTGTG GGCTTGGCCT TGTGTCAGAG CTGGGAGTAG   1623

CATGGACTCT GGGTTTCATA TCCAGCTGAG TGAGAGGGTT TGAGTCAAAA GCCTGGGTGA   1683

GAATCCTGCC TCTCCCCAAA CATTAATCAC CAAAGTATTA ATGTACAGAG TGGCCCCTCA   1743

CCTGGGCCTT TCCTGTGCCA ACCTGATGCC CCTTCCCCAA GAAGGTGAGT GCTTGTCATG   1803

GAAAATGTCC TGTGGTGACA GGCCCAGTGG AACAGTCACC CTTCTGGGCA AGGGGGAACA   1863
```

```
AATCACACCT CTGGGCTTCA GGGTATCCCA GACCCCTCTC AACACCCGCC CCCCCCATGT      1923

TTAAACTTTG TGCCTTTGAC CATCTCTTAG GTCTAATGAT ATTTTATGCA AACAGTTCTT      1983

GGACCCCTGA ATTCTTCAAT GACAGGGATG CCAACACCTT CTTGGCTTCT GGGACCTGTG      2043

TTCTTGCTGA GCACCCTCTC CGGTTTGGGT TGGGATAACA GAGGCAGGAG TGGCAGCTGT      2103

CCCCTCTCCC TGGGGATATG CAACCCTTAG AGATTGCCCC AGAGCCCCAC TCCCGGCCAG      2163

GCGGGAGATG GACCCCTCCC TTGCTCAGTG CCTCCTGGCC GGGGCCCCTC ACCCCAAGGG      2223

GTCTGTATAT ACATTTCATA AGGCCTGCCC TCCCATGTTG CATGCCTATG TACTCTGCGC      2283

CAAAGTGCAG CCCTTCCTCC TGAAGCCTCT GCCCTGCCTC CCTTTCTGGG AGGGCGGGGT      2343

GGGGGTGACT GAATTTGGGC CTCTTGTACA GTTAACTCTC CCAGGTGGAT TTTGTGGAGG      2403

TGAGAAAAGG GGCATTGAGA CTATAAAGCA GTAGACAATC CCCACATACC ATCTGTAGAG      2463

TTGGAACTGC ATTCTTTTAA AGTTTTATAT GCATATATTT TAGGGCTGCT AGACTTACTT      2523

TCCTATTTTC TTTTCCATTG CTTATTCTTG AGCACAAAAT GATAATCAAT TATTACATTT      2583

ATACATCACC TTTTTGACTT TTCCAAGCCC TTTTACAGCT CTTGGCATTT TCCTCGCCTA      2643

GGCCTGTGAG GTAACTGGGA TCGCACCTTT TATACCAGAG ACCTGAGGCA GATGAAATTT      2703

ATTTCCATCT AGGACTAGAA AAACTTGGGT CTCTTACCGC GAGACTGAGA GGCAGAAGTC      2763

AGCCCGAATG CCTGTCAGTT TCATGGAGGG GAAACGCAAA ACCTGCAGTT CCTGAGTACC      2823

TTCTACAGGC CCGGCCCAGC CTAGGCCCGG GGTGGCCACA CCACAGCAAG CCGGCCCCCC      2883

CTCTTTTGGC CTTGTGGATA AGGGAGAGTT GACCGTTTTC ATCCTGGCCT CCTTTTGCTG      2943

TTTGGATGTT TCCACGGGTC TCACTTATAC CAAAGGGAAA ACTCTTCATT AAAGTCCCGT      3003

ATTTCTTCTA AAAAAAAAA AAAAAAA                                           3031

(2) INFORMATION FOR SEQ ID NO:4:

(i) SEQUENCE CHARACTERISTICS:
        (A) LENGTH: 473 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Lys Leu Ser Gly Gly Gly Arg Arg Thr Arg Val Glu Gly
  1               5                  10                  15

Gly Gln Leu Gly Gly Glu Glu Trp Thr Arg His Gly Ser Phe Val Asn
                 20                  25                  30

Lys Pro Thr Arg Gly Trp Leu His Pro Asn Asp Lys Val Met Gly Pro
         35                  40                  45

Gly Val Ser Tyr Leu Val Arg Tyr Met Gly Cys Val Glu Val Leu Gln
     50                  55                  60

Ser Met Arg Ala Leu Asp Phe Asn Thr Arg Thr Gln Val Thr Arg Glu
 65                  70                  75                  80

Ala Ile Ser Leu Val Cys Glu Ala Val Pro Gly Ala Lys Gly Ala Thr
                 85                  90                  95

Arg Arg Arg Lys Pro Cys Ser Arg Pro Leu Ser Ser Ile Leu Gly Arg
            100                 105                 110

Ser Asn Leu Lys Phe Ala Gly Met Pro Ile Thr Leu Thr Val Ser Thr
        115                 120                 125

Ser Ser Leu Asn Leu Met Ala Ala Asp Cys Lys Gln Ile Ile Ala Asn
    130                 135                 140
```

His His Met Gln Ser Ile Ser Phe Ala Ser Gly Gly Asp Pro Asp Thr
145                 150                 155                 160

Ala Glu Tyr Val Ala Tyr Val Ala Lys Asp Pro Val Asn Gln Arg Ala
                165                 170                 175

Cys His Ile Leu Glu Cys Pro Glu Gly Leu Ala Gln Asp Val Ile Ser
                180                 185                 190

Thr Ile Gly Gln Ala Phe Glu Leu Arg Phe Lys Gln Tyr Leu Arg Asn
            195                 200                 205

Pro Pro Lys Leu Val Thr Pro His Asp Arg Met Ala Gly Phe Asp Gly
210                 215                 220

Ser Ala Trp Asp Glu Glu Glu Glu Pro Pro Asp His Gln Tyr Tyr
225                 230                 235                 240

Asn Asp Phe Pro Gly Lys Glu Pro Pro Leu Gly Gly Val Val Asp Met
                245                 250                 255

Arg Leu Arg Glu Gly Ala Ala Pro Gly Ala Ala Arg Pro Thr Ala Pro
                260                 265                 270

Asn Ala Gln Thr Pro Ser His Leu Gly Ala Thr Leu Pro Val Gly Gln
                275                 280                 285

Pro Val Gly Gly Asp Pro Glu Val Arg Lys Gln Met Pro Pro Pro Pro
290                 295                 300

Pro Cys Pro Gly Arg Glu Leu Phe Asp Asp Pro Ser Tyr Val Asn Val
305                 310                 315                 320

Gln Asn Leu Asp Lys Ala Arg Gln Ala Val Gly Gly Ala Gly Pro Pro
                325                 330                 335

Asn Pro Ala Ile Asn Gly Ser Ala Pro Arg Asp Leu Phe Asp Met Lys
                340                 345                 350

Pro Phe Glu Asp Ala Leu Arg Val Pro Pro Pro Gln Ser Val Ser
                355                 360                 365

Met Ala Glu Gln Leu Arg Gly Glu Pro Trp Phe His Gly Lys Leu Ser
                370                 375                 380

Arg Arg Glu Ala Glu Ala Leu Leu Gln Leu Asn Gly Asp Phe Leu Val
385                 390                 395                 400

Arg Glu Ser Thr Thr Thr Pro Gly Gln Tyr Val Leu Thr Gly Leu Gln
                405                 410                 415

Ser Gly Gln Pro Lys His Leu Leu Leu Val Asp Pro Glu Gly Val Val
                420                 425                 430

Arg Thr Lys Asp His Arg Phe Glu Ser Val Ser His Leu Ile Ser Tyr
                435                 440                 445

His Met Asp Asn His Leu Pro Ile Ile Ser Ala Gly Ser Glu Leu Cys
450                 455                 460

Leu Gln Gln Pro Val Glu Arg Lys Leu
465                 470

(2) INFORMATION FOR SEQ ID NO:5:

(i) SEQUENCE CHARACTERISTICS:
        (A) LENGTH: 1109 base pairs
        (B) TYPE: nucleic acid
        (C) STRANDEDNESS: single
        (D) TOPOLOGY: linear (ii) MOLECULE TYPE: mRNA (vi) ORIGINAL SOURCE:
        (A) ORGANISM: Homo sapiens
        (B) STRAIN: GRB2

(ix) FEATURE:
    (A) NAME/KEY: CDS
    (B) LOCATION: 79..732

(xi) SEQUENCE DESCRIPTION: SEQ ID NO:5:

```
GCCAGTGAAT TCGGGGGCTC AGCCCTCCTC CCTCCCTTCC CCCTGCTTCA GGCTGCTGAG      60

CACTGAGCAG CGCTCAGA ATG GAA GCC ATC GCC AAA TAT GAC TTC AAA GCT      111
                    Met Glu Ala Ile Ala Lys Tyr Asp Phe Lys Ala
                     1               5                      10

ACT GCA GAC GAC GAG CTG AGC TTC AAA AGG GGG GAC ATC CTC AAG GTT      159
Thr Ala Asp Asp Glu Leu Ser Phe Lys Arg Gly Asp Ile Leu Lys Val
             15                  20                  25

TTG AAC GAA GAA TGT GAT CAG AAC TGG TAC AAG GCA GAG CTT AAT GGA      207
Leu Asn Glu Glu Cys Asp Gln Asn Trp Tyr Lys Ala Glu Leu Asn Gly
         30                  35                  40

AAA GAC GGC TTC ATT CCC AAG AAC TAC ATA GAA ATG AAA CCA CAT CCG      255
Lys Asp Gly Phe Ile Pro Lys Asn Tyr Ile Glu Met Lys Pro His Pro
     45                  50                  55

TGG TTT TTT GGC AAA ATC CCC AGA GCC AAG GCA GAA GAA ATG CTT AGC      303
Trp Phe Phe Gly Lys Ile Pro Arg Ala Lys Ala Glu Glu Met Leu Ser
 60                  65                  70                  75

AAA CAG CGG CAC GAT GGG GCC TTT CTT ATC CGA GAG AGT GAG AGC GCT      351
Lys Gln Arg His Asp Gly Ala Phe Leu Ile Arg Glu Ser Glu Ser Ala
                 80                  85                  90

CCT GGG GAC TTC TCC CTC TCT GTC AAG TTT GGA AAC GAT GTG CAG CAC      399
Pro Gly Asp Phe Ser Leu Ser Val Lys Phe Gly Asn Asp Val Gln His
             95                 100                 105

TTC AAG GTG CTC CGA GAT GGA GCC GGG AAG TAC TTC CTC TGG GTG GTG      447
Phe Lys Val Leu Arg Asp Gly Ala Gly Lys Tyr Phe Leu Trp Val Val
         110                 115                 120

AAG TTC AAT TCT TTG AAT GAG CTG GTG GAT TAT CAC AGA TCT ACA TCT      495
Lys Phe Asn Ser Leu Asn Glu Leu Val Asp Tyr His Arg Ser Thr Ser
125                 130                 135

GTC TCC AGA AAC CAG CAG ATA TTC CTG CGG GAC ATA GAA CAG GTG CCA      543
Val Ser Arg Asn Gln Gln Ile Phe Leu Arg Asp Ile Glu Gln Val Pro
140                 145                 150                 155

CAG CAG CCG ACA TAC GTC CAG GCC CTC TTT GAC TTT GAT CCC CAG GAG      591
Gln Gln Pro Thr Tyr Val Gln Ala Leu Phe Asp Phe Asp Pro Gln Glu
                160                 165                 170

GAT GGA GAG CTG GGC TTC CGC CGG GGA GAT TTT ATC CAT GTC ATG GAT      639
Asp Gly Glu Leu Gly Phe Arg Arg Gly Asp Phe Ile His Val Met Asp
            175                 180                 185

AAC TCA GAC CCC AAC TGG TGG AAA GGA GCT TGC CAC GGG CAG ACC GGC      687
Asn Ser Asp Pro Asn Trp Trp Lys Gly Ala Cys His Gly Gln Thr Gly
        190                 195                 200

ATG TTT CCC CGC AAT TAT GTC ACC CCC GTG AAC CGG AAC GTC TAA         732
Met Phe Pro Arg Asn Tyr Val Thr Pro Val Asn Arg Asn Val  *
    205                 210                 215

GAGTCAAGAA GCAATTATTT AAAGAAAGTG AAAAATGTAA AACACATACA AAAGAATTAA      792

ACCCACAAGC TGCCTCTGAC AGCAGCCTGT GAGGGAGTGC AGAACACCTG GCCGGGTCAC      852

CCTGTGACCC TCTCACTTTG GTTGGAACTT TAGGGGGTGG GAGGGGGCGT TGGATTTAAA      912

AATGCCAAAA CTTACCTATA AATTAAGAAG AGTTTTTATT ACAAATTTTC ACTGCTGCTC      972

CTCTTTCCCC TCCTTTGTCT TTTTTTTCAT CCTTTTTTCT CTTCTGTCCA TCAGTGCATG     1032

ACGTTTAAGG CCACGTATAG TCCTAGCTGA CGCCAATAAT AAAAAACAAG AAACCAAAAA     1092

AAAAAAACCC GAATTCA                                                   1109
```

(2) INFORMATION FOR SEQ ID NO:6:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Ala Ile Ala Lys Tyr Asp Phe Lys Ala Thr Ala Asp Asp Glu
 1               5                  10                  15

Leu Ser Phe Lys Arg Gly Asp Ile Leu Lys Val Leu Asn Glu Glu Cys
             20                  25                  30

Asp Gln Asn Trp Tyr Lys Ala Glu Leu Asn Gly Lys Asp Gly Phe Ile
         35                  40                  45

Pro Lys Asn Tyr Ile Glu Met Lys Pro His Pro Trp Phe Phe Gly Lys
     50                  55                  60

Ile Pro Arg Ala Lys Ala Glu Glu Met Leu Ser Lys Gln Arg His Asp
 65                  70                  75                  80

Gly Ala Phe Leu Ile Arg Glu Ser Glu Ser Ala Pro Gly Asp Phe Ser
             85                  90                  95

Leu Ser Val Lys Phe Gly Asn Asp Val Gln His Phe Lys Val Leu Arg
            100                 105                 110

Asp Gly Ala Gly Lys Tyr Phe Leu Trp Val Val Lys Phe Asn Ser Leu
        115                 120                 125

Asn Glu Leu Val Asp Tyr His Arg Ser Thr Ser Val Ser Arg Asn Gln
    130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
            180                 185                 190

Trp Trp Lys Gly Ala Cys His Gly Gln Thr Gly Met Phe Pro Arg Asn
        195                 200                 205

Tyr Val Thr Pro Val Asn Arg Asn Val
    210                 215
```

(2) INFORMATION FOR SEQ ID NO:7:

(i) SEQUENCE CHARACTERISTICS:
        (A) LENGTH: 4870 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: hSHIP (ix) FEATURE:
        (A) NAME/KEY: CDS
        (B) LOCATION: 113..3673

(xi) SEQUENCE DESCRIPTION: SEQ ID NO:7:

```
CCCAAGAGGC AACGGGCGGC AGGTTGCAGT GGAGGGGCCT CCGCTCCCCT CGGTGGTGTG      60
TGGGTCCTGG GGGTGCCTGC CGGCCCAGCC GAGGAGGCCC ACGCCCACCA TG GTC         115
```

-continued

```
                                Val
                                 1

CCC TGC TGG AAC CAT GGC AAC ATC ACC CGC TCC AAG GCG GAG GAG CTG        163
Pro Cys Trp Asn His Gly Asn Ile Thr Arg Ser Lys Ala Glu Glu Leu
             5                  10                  15

CTT TGC AGG ACA GGC AAG GAC GGG AGC TTC CTC GTG CGT GCC AGC GAG        211
Leu Cys Arg Thr Gly Lys Asp Gly Ser Phe Leu Val Arg Ala Ser Glu
         20                  25                  30

TCC ATC TTC CGG GCA TAC GCG CTC TGC GTG CTG TAT CGG AAT TGC GTT        259
Ser Ile Phe Arg Ala Tyr Ala Leu Cys Val Leu Tyr Arg Asn Cys Val
     35                  40                  45

TAT ACT TAC AGA ATT CTG CCC AAT GAA GAT GAT AAA TTC ACT GTT CAG        307
Tyr Thr Tyr Arg Ile Leu Pro Asn Glu Asp Asp Lys Phe Thr Val Gln
 50                  55                  60                  65

GCA TCC GAA GGC GTC TCC ATG AGG TTC TTC ACC AAG CTG GAC CAG CTC        355
Ala Ser Glu Gly Val Ser Met Arg Phe Phe Thr Lys Leu Asp Gln Leu
                 70                  75                  80

ATC GAG TTT TAC AAG AAG GAA AAC ATG GGG CTG GTG ACC CAT CTG CAA        403
Ile Glu Phe Tyr Lys Lys Glu Asn Met Gly Leu Val Thr His Leu Gln
             85                  90                  95

TAC CCT GTG CCG CTG GAG GAA GAG GAC ACA GGC GAC GAC CCT GAG GAG        451
Tyr Pro Val Pro Leu Glu Glu Glu Asp Thr Gly Asp Asp Pro Glu Glu
         100                 105                 110

GAC ACA GAA AGT GTC GTG TCT CCA CCC GAG CTG CCC CCA AGA AAC ATC        499
Asp Thr Glu Ser Val Val Ser Pro Pro Glu Leu Pro Pro Arg Asn Ile
     115                 120                 125

CCG CTG ACT GCC AGC TCC TGT GAG GCC AAG GAG GTT CCT TTT TCA AAC        547
Pro Leu Thr Ala Ser Ser Cys Glu Ala Lys Glu Val Pro Phe Ser Asn
130                 135                 140                 145

GAG AAT CCC CGA GCG ACC GAG ACC AGC CGG CCG AGC CTC TCC GAG ACA        595
Glu Asn Pro Arg Ala Thr Glu Thr Ser Arg Pro Ser Leu Ser Glu Thr
                 150                 155                 160

TTG TTC CAG CGA CTG CAA AGC ATG GAC ACC AGT GGG CTT CCA GAA GAG        643
Leu Phe Gln Arg Leu Gln Ser Met Asp Thr Ser Gly Leu Pro Glu Glu
             165                 170                 175

CAT CTT AAG GCC ATC CAA GAT TAT TTA AGC ACT CAG CTC GCC CAG GAC        691
His Leu Lys Ala Ile Gln Asp Tyr Leu Ser Thr Gln Leu Ala Gln Asp
         180                 185                 190

TCT GAA TTT GTG AAG ACA GGG TCC AGC AGT CTT CCT CAC CTG AAG AAA        739
Ser Glu Phe Val Lys Thr Gly Ser Ser Ser Leu Pro His Leu Lys Lys
     195                 200                 205

CTG ACC ACA CTG CTC TGC AAG GAG CTC TAT GGA GAA GTC ATC CGG ACC        787
Leu Thr Thr Leu Leu Cys Lys Glu Leu Tyr Gly Glu Val Ile Arg Thr
210                 215                 220                 225

CTC CCA TCC CTG GAG TCT CTG CAG AGG TTA TTT GAC CAG CAG CTC TCC        835
Leu Pro Ser Leu Glu Ser Leu Gln Arg Leu Phe Asp Gln Gln Leu Ser
                 230                 235                 240

CCG GGC CTC CGT CCA CGT CCT CAG GTT CCT GGT GAG GCC AAT CCC ATC        883
Pro Gly Leu Arg Pro Arg Pro Gln Val Pro Gly Glu Ala Asn Pro Ile
             245                 250                 255

AAC ATG GTG TCC AAG CTC AGC CAA CTG ACA AGC CTG TTG TCA TCC ATT        931
Asn Met Val Ser Lys Leu Ser Gln Leu Thr Ser Leu Leu Ser Ser Ile
         260                 265                 270

GAA GAC AAG GTC AAG GCC TTG CTG CAC GAG GGT CCT GAG TCT CCG CAC        979
Glu Asp Lys Val Lys Ala Leu Leu His Glu Gly Pro Glu Ser Pro His
     275                 280                 285

CGG CCC TCC CTT ATC CCT CCA GTC ACC TTT GAG GTG AAG GCA GAG TCT       1027
Arg Pro Ser Leu Ile Pro Pro Val Thr Phe Glu Val Lys Ala Glu Ser
 290                 295                 300                 305
```

```
CTG GGG ATT CCT CAG AAA ATG CAG CTC AAA GTC GAC GTT GAG TCT GGG         1075
Leu Gly Ile Pro Gln Lys Met Gln Leu Lys Val Asp Val Glu Ser Gly
             310                 315                 320

AAA CTG ATC ATT AAG AAG TCC AAG GAT GGT TCT GAG GAC AAG TTC TAC         1123
Lys Leu Ile Ile Lys Lys Ser Lys Asp Gly Ser Glu Asp Lys Phe Tyr
             325                 330                 335

AGC CAC AAG AAA ATC CTG CAG CTC ATT AAG TCA CAG AAA TTT CTG AAT         1171
Ser His Lys Lys Ile Leu Gln Leu Ile Lys Ser Gln Lys Phe Leu Asn
             340                 345                 350

AAG TTG GTG ATC TTG GTG GAA ACA GAG AAG GAG AAG ATC CTG CGG AAG         1219
Lys Leu Val Ile Leu Val Glu Thr Glu Lys Glu Lys Ile Leu Arg Lys
         355                 360                 365

GAA TAT GTT TTT GCT GAC TCC AAA AAG AGA GAA GGC TTC TGC CAG CTC         1267
Glu Tyr Val Phe Ala Asp Ser Lys Lys Arg Glu Gly Phe Cys Gln Leu
370                 375                 380                 385

CTG CAG CAG ATG AAG AAC AAG CAC TCA GAG CAG CCG GAG CCC GAC ATG         1315
Leu Gln Gln Met Lys Asn Lys His Ser Glu Gln Pro Glu Pro Asp Met
                 390                 395                 400

ATC ACC ATC TTC ATC GGC ACC TGG AAC ATG GGT AAC GCC CCC CCT CCC         1363
Ile Thr Ile Phe Ile Gly Thr Trp Asn Met Gly Asn Ala Pro Pro Pro
                 405                 410                 415

AAG AAG ATC ACG TCC TGG TTT CTC TCC AAG GGG CAG GGA AAG ACG CGG         1411
Lys Lys Ile Thr Ser Trp Phe Leu Ser Lys Gly Gln Gly Lys Thr Arg
                 420                 425                 430

GAC GAC TCT GCG GAC TAC ATC CCC CAT GAC ATT TAC GTG ATC GGC ACC         1459
Asp Asp Ser Ala Asp Tyr Ile Pro His Asp Ile Tyr Val Ile Gly Thr
             435                 440                 445

CAA GAG GAC CCC CTG AGT GAG AAG GAG TGG CTG GAG ATC CTC AAA CAC         1507
Gln Glu Asp Pro Leu Ser Glu Lys Glu Trp Leu Glu Ile Leu Lys His
450                 455                 460                 465

TCC CTG CAA GAA ATC ACC AGT GTG ACT TTT AAA ACA GTC GCC ATC CAC         1555
Ser Leu Gln Glu Ile Thr Ser Val Thr Phe Lys Thr Val Ala Ile His
                 470                 475                 480

ACG CTC TGG AAC ATC CGC ATC GTG GTG CTG GCC AAG CCT GAG CAC GAG         1603
Thr Leu Trp Asn Ile Arg Ile Val Val Leu Ala Lys Pro Glu His Glu
                 485                 490                 495

AAC CGG ATC AGC CAC ATC TGT ACT GAC AAC GTG AAG ACA GGC ATT GCA         1651
Asn Arg Ile Ser His Ile Cys Thr Asp Asn Val Lys Thr Gly Ile Ala
                 500                 505                 510

AAC ACA CTG GGG AAC AAG GGA GCC GTG GGG GTG TCG TTC ATG TTC AAT         1699
Asn Thr Leu Gly Asn Lys Gly Ala Val Gly Val Ser Phe Met Phe Asn
             515                 520                 525

GGA ACC TCC TTA GGG TTC GTC AAC AGC CAC TTG ACT TCA GGA AGT GAA         1747
Gly Thr Ser Leu Gly Phe Val Asn Ser His Leu Thr Ser Gly Ser Glu
530                 535                 540                 545

AAG AAA CTC AGG CGA AAC CAA AAC TAT ATG AAC ATT CTC CGG TTC CTG         1795
Lys Lys Leu Arg Arg Asn Gln Asn Tyr Met Asn Ile Leu Arg Phe Leu
                 550                 555                 560

GCC CTG GGC GAC AAG AAG CTG AGT CCC TTT AAC ATC ACT CAC CGC TTC         1843
Ala Leu Gly Asp Lys Lys Leu Ser Pro Phe Asn Ile Thr His Arg Phe
                 565                 570                 575

ACG CAC CTC TTC TGG TTT GGG GAT CTT AAC TAC CGT GTG GAT CTG CCT         1891
Thr His Leu Phe Trp Phe Gly Asp Leu Asn Tyr Arg Val Asp Leu Pro
                 580                 585                 590

ACC TGG GAG GCA GAA ACC ATC ATC CAA AAA ATC AAG CAG CAG CAG TAC         1939
Thr Trp Glu Ala Glu Thr Ile Ile Gln Lys Ile Lys Gln Gln Gln Tyr
             595                 600                 605

GCA GAC CTC CTG TCC CAC GAC CAG CTG CTC ACA GAG AGG AGG GAG CAG         1987
Ala Asp Leu Leu Ser His Asp Gln Leu Leu Thr Glu Arg Arg Glu Gln
610                 615                 620                 625
```

```
AAG GTC TTC CTA CAC TTC GAG GAG GAA GAA ATC ACG TTT GCC CCA ACC    2035
Lys Val Phe Leu His Phe Glu Glu Glu Glu Ile Thr Phe Ala Pro Thr
            630                 635                 640

TAC CGT TTT GAG AGA CTG ACT CGG GAC AAA TAC GCC TAC ACC AAG CAG    2083
Tyr Arg Phe Glu Arg Leu Thr Arg Asp Lys Tyr Ala Tyr Thr Lys Gln
            645                 650                 655

AAA GCG ACA GGG ATG AAG TAC AAC TTG CCT TCC TGG TGT GAC CGA GTC    2131
Lys Ala Thr Gly Met Lys Tyr Asn Leu Pro Ser Trp Cys Asp Arg Val
            660                 665                 670

CTC TGG AAG TCT TAT CCC CTG GTG CAC GTG GTG TGT CAG TCT TAT GGC    2179
Leu Trp Lys Ser Tyr Pro Leu Val His Val Val Cys Gln Ser Tyr Gly
    675                 680                 685

AGT ACC AGC GAC ATC ATG ACG AGT GAC CAC AGC CCT GTC TTT GCC ACA    2227
Ser Thr Ser Asp Ile Met Thr Ser Asp His Ser Pro Val Phe Ala Thr
690                 695                 700                 705

TTT GAG GCA GGA GTC ACT TCC CAG TTT GTC TCC AAG AAC GGT CCC GGG    2275
Phe Glu Ala Gly Val Thr Ser Gln Phe Val Ser Lys Asn Gly Pro Gly
            710                 715                 720

ACT GTT GAC AGC CAA GGA CAG ATT GAG TTT CTC AGG TGC TAT GCC ACA    2323
Thr Val Asp Ser Gln Gly Gln Ile Glu Phe Leu Arg Cys Tyr Ala Thr
            725                 730                 735

TTG AAG ACC AAG TCC CAG ACC AAA TTC TAC CTG GAG TTC CAC TCG AGC    2371
Leu Lys Thr Lys Ser Gln Thr Lys Phe Tyr Leu Glu Phe His Ser Ser
            740                 745                 750

TGC TTG GAG AGT TTT GTC AAG AGT CAG GAA GGA GAA AAT GAA GAA GGA    2419
Cys Leu Glu Ser Phe Val Lys Ser Gln Glu Gly Glu Asn Glu Glu Gly
    755                 760                 765

AGT GAG GGG GAG CTG GTG GTG AAG TTT GGT GAG ACT CTT CCA AAG CTG    2467
Ser Glu Gly Glu Leu Val Val Lys Phe Gly Glu Thr Leu Pro Lys Leu
770                 775                 780                 785

AAG CCC ATT ATC TCT GAC CCT GAG TAC CTG CTA GAC CAG CAC ATC CTC    2515
Lys Pro Ile Ile Ser Asp Pro Glu Tyr Leu Leu Asp Gln His Ile Leu
            790                 795                 800

ATC AGC ATC AAG TCC TCT GAC AGC GAC GAA TCC TAT GGC GAG GGC TGC    2563
Ile Ser Ile Lys Ser Ser Asp Ser Asp Glu Ser Tyr Gly Glu Gly Cys
            805                 810                 815

ATT GCC CTT CGG TTA GAG GCC ACA GAA ACG CAG CTG CCC ATC TAC ACG    2611
Ile Ala Leu Arg Leu Glu Ala Thr Glu Thr Gln Leu Pro Ile Tyr Thr
    820                 825                 830

CCT CTC ACC CAC CAT GGG GAG TTG ACA GGC CAC TTC CAG GGG GAG ATC    2659
Pro Leu Thr His His Gly Glu Leu Thr Gly His Phe Gln Gly Glu Ile
835                 840                 845

AAG CTG CAG ACC TCT CAG GGC AAG ACG AGG GAG AAG CTC TAT GAC TTT    2707
Lys Leu Gln Thr Ser Gln Gly Lys Thr Arg Glu Lys Leu Tyr Asp Phe
850                 855                 860                 865

GTG AAG ACG GAG CGT GAT GAA TCC AGT GGG CCA AAG ACC CTG AAG AGC    2755
Val Lys Thr Glu Arg Asp Glu Ser Ser Gly Pro Lys Thr Leu Lys Ser
            870                 875                 880

CTC ACC AGC CAC GAC CCC ATG AAG CAG TGG GAA GTC ACT AGC AGG GCC    2803
Leu Thr Ser His Asp Pro Met Lys Gln Trp Glu Val Thr Ser Arg Ala
            885                 890                 895

CCT CCG TGC AGT GGC TCC AGC ATC ACT GAA ATC ATC AAC CCC AAC TAC    2851
Pro Pro Cys Ser Gly Ser Ser Ile Thr Glu Ile Ile Asn Pro Asn Tyr
            900                 905                 910

ATG GGA GTG GGG CCC TTT GGG CCA CCA ATG CCC CTG CAC GTG AAG CAG    2899
Met Gly Val Gly Pro Phe Gly Pro Pro Met Pro Leu His Val Lys Gln
            915                 920                 925

ACC TTG TCC CCT GAC CAG CAG CCC ACA GCC TGG AGC TAC GAC CAG CCG    2947
Thr Leu Ser Pro Asp Gln Gln Pro Thr Ala Trp Ser Tyr Asp Gln Pro
```

```
                  930              935              940              945
CCC AAG GAC TCC CCG CTG GGG CCC TGC AGG GGA GAA AGT CCT CCG ACA        2995
Pro Lys Asp Ser Pro Leu Gly Pro Cys Arg Gly Glu Ser Pro Pro Thr
                950              955              960

CCT CCC GGC CAG CCG CCC ATA TCA CCC AAG AAG TTT TTA CCC TCA ACA        3043
Pro Pro Gly Gln Pro Pro Ile Ser Pro Lys Lys Phe Leu Pro Ser Thr
                965              970              975

GCA AAC CGG GGT CTC CCT CCC AGG ACA CAG GAG TCA AGG CCC AGT GAC        3091
Ala Asn Arg Gly Leu Pro Pro Arg Thr Gln Glu Ser Arg Pro Ser Asp
            980              985              990

CTG GGG AAG AAC GCA GGG GAC ACG CTG CCT CAG GAG GAC CTG CCG CTG        3139
Leu Gly Lys Asn Ala Gly Asp Thr Leu Pro Gln Glu Asp Leu Pro Leu
    995              1000             1005

ACG AAG CCC GAG ATG TTT GAG AAC CCC CTG TAT GGG TCC CTG AGT TCC        3187
Thr Lys Pro Glu Met Phe Glu Asn Pro Leu Tyr Gly Ser Leu Ser Ser
1010             1015             1020             1025

TTC CCT AAG CCT GCT CCC AGG AAG GAC CAG GAA TCC CCC AAA ATG CCG        3235
Phe Pro Lys Pro Ala Pro Arg Lys Asp Gln Glu Ser Pro Lys Met Pro
                1030             1035             1040

CGG AAG GAA CCC CCG CCC TGC CCG GAA CCC GGC ATC TTG TCG CCC AGC        3283
Arg Lys Glu Pro Pro Pro Cys Pro Glu Pro Gly Ile Leu Ser Pro Ser
                1045             1050             1055

ATC GTG CTC ACC AAA GCC CAG GAG GCT GAT CGC GGC GAG GGG CCC GGC        3331
Ile Val Leu Thr Lys Ala Gln Glu Ala Asp Arg Gly Glu Gly Pro Gly
            1060             1065             1070

AAG CAG GTG CCC GCG CCC CGG CTG CGC TCC TTC ACG TGC TCA TCC TCT        3379
Lys Gln Val Pro Ala Pro Arg Leu Arg Ser Phe Thr Cys Ser Ser Ser
        1075             1080             1085

GCC GAG GGC AGG GCG GCC GGC GGG GAC AAG AGC CAA GGG AAG CCC AAG        3427
Ala Glu Gly Arg Ala Ala Gly Gly Asp Lys Ser Gln Gly Lys Pro Lys
1090             1095             1100             1105

ACC CCG GTC AGC TCC CAG GCC CCG GTG CCG GCC AAG AGG CCC ATC AAG        3475
Thr Pro Val Ser Ser Gln Ala Pro Val Pro Ala Lys Arg Pro Ile Lys
                1110             1115             1120

CCT TCC AGA TCG GAA ATC AAC CAG CAG ACC CCG CCC ACC CCG ACG CCG        3523
Pro Ser Arg Ser Glu Ile Asn Gln Gln Thr Pro Pro Thr Pro Thr Pro
                1125             1130             1135

CGG CCG CCG CTG CCA GTC AAG AGC CCG GCG GTG CTG CAC CTC CAG CAC        3571
Arg Pro Pro Leu Pro Val Lys Ser Pro Ala Val Leu His Leu Gln His
            1140             1145             1150

TCC AAG GGC CGC GAC TAC CGC GAC AAC ACC GAG CTC CCG CAT CAC GGC        3619
Ser Lys Gly Arg Asp Tyr Arg Asp Asn Thr Glu Leu Pro His His Gly
            1155             1160             1165

AAG CAC CGG CCG GAG GAG GGG CCA CCA GGG CCT CTA GGC AGG ACT GCC        3667
Lys His Arg Pro Glu Glu Gly Pro Pro Gly Pro Leu Gly Arg Thr Ala
1170             1175             1180             1185

ATG CAG TGAAGCCCTC AGTGAGCTGC CACTGAGTCG GGAGCCCAGA GGAACGGCGT         3723
Met Gln

GAAGCCACTG GACCCTCTCC CGGGACCTCC TGCTGGCTCC TCCTGCCCAG CTTCCTATGC     3783

AAGGCTTTGT GTTTTCAGGA AAGGGCCTAG CTTCTGTGTG GCCACAGAG TTCACTGCCT      3843

GTGAGGCTTA GCACCAAGTG CTGAGGCTGG AAGAAAAACG CACACCAGAC GGGCAACAAA     3903

CAGTCTGGGT CCCCAGCTCG CTCTTGGTAC TTGGACCCC AGTGCCTCGT TGAGGGCGCC      3963

ATTCTGAAGA AAGGAACTGC AGCGCCGATT TGAGGGTGGA GATATAGATA ATAATAATAT     4023

TAATAATAAT AATGGCCACA TGGATCGAAC ACTCATGATG TGCCAAGTGC TGTGCTAAGT     4083

GCTTTACGAA CATTCGTCAT ATCAGGATGA CCTCGAGAGC TGAGGCTCTA GCCACCTAAA     4143
```

-continued

```
ACACGTGCCC AAACCCACCA GTTTAAAACG GTGTGTGTTC GGAGGGGTGA AAGCATTAAG    4203

AAGCCCAGTG CCCTCCTGGA GTGAGACAAG GGCTCGGCCT TAAGGAGCTG AAGAGTCTGG    4263

GTAGCTTGTT TAGGGTACAA GAAGCCTGTT CTGTCCAGCT TCAGTGACAC AAGCTGCTTT    4323

AGCTAAAGTC CCGCGGGTTC CGGCATGGCT AGGCTGAGAG CAGGGATCTA CCTGGCTTCT    4383

CAGTTCTTTG GTTGGAAGGA GCAGGAAATC AGCTCCTATT CTCCAGTGGA GAGATCTGGC    4443

CTCAGCTTGG GCTAGAGATG CCAAGGCCTG TGCCAGGTTC CCTGTGCCCT CCTCGAGGTG    4503

GGCAGCCATC ACCAGCCACA GTTAAGCCAA GCCCCCCAAC ATGTATTCCA TCGTGCTGGT    4563

AGAAGAGTCT TTGCTGTTGC TCCCGAAAGC CGTGCTCTCC AGCCTGGCTG CCAGGGAGGG    4623

TGGGCCTCTT GGTTCCAGGC TCTTGAAATA GTGCAGCCTT TCTTCCTAT CTCTGTGGCT     4683

TTCAGCTCTG CTTCCTTGGT TATTAGGAGA ATAGATGGGT GATGTCTTTC CTTATGTTGC    4743

TTTTTCAACA TAGCAGAATT AATGTAGGGA GCTAAATCCA GTGGTGTGTG TGAATGCAGA    4803

AGGGAATGCA CCCCACATTC CCATGATGGA AGTCTGCGTA ACCAATAAAT TGTGCCTTTC    4863

TTAAAAA                                                              4870
```

(2) INFORMATION FOR SEQ ID NO:8:

(i) SEQUENCE CHARACTERISTICS:
        (A) LENGTH: 1187 amino acids
        (B) TYPE: amino acid
        (D) TOPOLOGY: linear (ii) MOLECULE TYPE: protein (xi) SEQUENCE DESCRIPTION: SEQ ID NO:8:

```
Val Pro Cys Trp Asn His Gly Asn Ile Thr Arg Ser Lys Ala Glu Glu
 1               5                  10                  15

Leu Leu Cys Arg Thr Gly Lys Asp Gly Ser Phe Leu Val Arg Ala Ser
                20                  25                  30

Glu Ser Ile Phe Arg Ala Tyr Ala Leu Cys Val Leu Tyr Arg Asn Cys
             35                  40                  45

Val Tyr Thr Tyr Arg Ile Leu Pro Asn Glu Asp Asp Lys Phe Thr Val
 50                  55                  60

Gln Ala Ser Glu Gly Val Ser Met Arg Phe Phe Thr Lys Leu Asp Gln
 65                  70                  75                  80

Leu Ile Glu Phe Tyr Lys Lys Glu Asn Met Gly Leu Val Thr His Leu
                85                  90                  95

Gln Tyr Pro Val Pro Leu Glu Glu Glu Asp Thr Gly Asp Asp Pro Glu
            100                 105                 110

Glu Asp Thr Glu Ser Val Val Ser Pro Pro Glu Leu Pro Pro Arg Asn
        115                 120                 125

Ile Pro Leu Thr Ala Ser Ser Cys Glu Ala Lys Glu Val Pro Phe Ser
130                 135                 140

Asn Glu Asn Pro Arg Ala Thr Glu Thr Ser Arg Pro Ser Leu Ser Glu
145                 150                 155                 160

Thr Leu Phe Gln Arg Leu Gln Ser Met Asp Thr Ser Gly Leu Pro Glu
                165                 170                 175

Glu His Leu Lys Ala Ile Gln Asp Tyr Leu Ser Thr Gln Leu Ala Gln
            180                 185                 190

Asp Ser Glu Phe Val Lys Thr Gly Ser Ser Ser Leu Pro His Leu Lys
        195                 200                 205

Lys Leu Thr Thr Leu Leu Cys Lys Glu Leu Tyr Gly Glu Val Ile Arg
210                 215                 220
```

-continued

```
Thr Leu Pro Ser Leu Glu Ser Leu Gln Arg Leu Phe Asp Gln Gln Leu
225                 230                 235                 240

Ser Pro Gly Leu Arg Pro Arg Pro Gln Val Pro Gly Glu Ala Asn Pro
            245                 250                 255

Ile Asn Met Val Ser Lys Leu Ser Gln Leu Thr Ser Leu Leu Ser Ser
        260                 265                 270

Ile Glu Asp Lys Val Lys Ala Leu Leu His Glu Gly Pro Glu Ser Pro
        275                 280                 285

His Arg Pro Ser Leu Ile Pro Pro Val Thr Phe Glu Val Lys Ala Glu
    290                 295                 300

Ser Leu Gly Ile Pro Gln Lys Met Gln Leu Lys Val Asp Val Glu Ser
305                 310                 315                 320

Gly Lys Leu Ile Ile Lys Lys Ser Lys Asp Gly Ser Glu Asp Lys Phe
                325                 330                 335

Tyr Ser His Lys Lys Ile Leu Gln Leu Ile Lys Ser Gln Lys Phe Leu
            340                 345                 350

Asn Lys Leu Val Ile Leu Val Glu Thr Glu Lys Glu Lys Ile Leu Arg
        355                 360                 365

Lys Glu Tyr Val Phe Ala Asp Ser Lys Lys Arg Glu Gly Phe Cys Gln
        370                 375                 380

Leu Leu Gln Gln Met Lys Asn Lys His Ser Glu Gln Pro Glu Pro Asp
385                 390                 395                 400

Met Ile Thr Ile Phe Ile Gly Thr Trp Asn Met Gly Asn Ala Pro Pro
                405                 410                 415

Pro Lys Lys Ile Thr Ser Trp Phe Leu Ser Lys Gly Gln Gly Lys Thr
            420                 425                 430

Arg Asp Asp Ser Ala Asp Tyr Ile Pro His Asp Ile Tyr Val Ile Gly
        435                 440                 445

Thr Gln Glu Asp Pro Leu Ser Glu Lys Glu Trp Leu Glu Ile Leu Lys
        450                 455                 460

His Ser Leu Gln Glu Ile Thr Ser Val Thr Phe Lys Thr Val Ala Ile
465                 470                 475                 480

His Thr Leu Trp Asn Ile Arg Ile Val Val Leu Ala Lys Pro Glu His
                485                 490                 495

Glu Asn Arg Ile Ser His Ile Cys Thr Asp Asn Val Lys Thr Gly Ile
            500                 505                 510

Ala Asn Thr Leu Gly Asn Lys Gly Ala Val Gly Val Ser Phe Met Phe
        515                 520                 525

Asn Gly Thr Ser Leu Gly Phe Val Asn Ser His Leu Thr Ser Gly Ser
        530                 535                 540

Glu Lys Lys Leu Arg Arg Asn Gln Asn Tyr Met Asn Ile Leu Arg Phe
545                 550                 555                 560

Leu Ala Leu Gly Asp Lys Lys Leu Ser Pro Phe Asn Ile Thr His Arg
                565                 570                 575

Phe Thr His Leu Phe Trp Phe Gly Asp Leu Asn Tyr Arg Val Asp Leu
            580                 585                 590

Pro Thr Trp Glu Ala Glu Thr Ile Ile Gln Lys Ile Lys Gln Gln Gln
        595                 600                 605

Tyr Ala Asp Leu Leu Ser His Asp Gln Leu Leu Thr Glu Arg Arg Glu
        610                 615                 620

Gln Lys Val Phe Leu His Phe Glu Glu Glu Ile Thr Phe Ala Pro
625                 630                 635                 640
```

```
Thr Tyr Arg Phe Glu Arg Leu Thr Arg Asp Lys Tyr Ala Tyr Thr Lys
                645                 650                 655

Gln Lys Ala Thr Gly Met Lys Tyr Asn Leu Pro Ser Trp Cys Asp Arg
            660                 665                 670

Val Leu Trp Lys Ser Tyr Pro Leu Val His Val Cys Gln Ser Tyr
        675                 680                 685

Gly Ser Thr Ser Asp Ile Met Thr Ser Asp His Ser Pro Val Phe Ala
    690                 695                 700

Thr Phe Glu Ala Gly Val Thr Ser Gln Phe Val Ser Lys Asn Gly Pro
705                 710                 715                 720

Gly Thr Val Asp Ser Gln Gly Gln Ile Glu Phe Leu Arg Cys Tyr Ala
                725                 730                 735

Thr Leu Lys Thr Lys Ser Gln Thr Lys Phe Tyr Leu Glu Phe His Ser
            740                 745                 750

Ser Cys Leu Glu Ser Phe Val Lys Ser Gln Glu Gly Glu Asn Glu Glu
        755                 760                 765

Gly Ser Glu Gly Glu Leu Val Val Lys Phe Gly Glu Thr Leu Pro Lys
    770                 775                 780

Leu Lys Pro Ile Ile Ser Asp Pro Glu Tyr Leu Leu Asp Gln His Ile
785                 790                 795                 800

Leu Ile Ser Ile Lys Ser Ser Asp Ser Asp Glu Ser Tyr Gly Glu Gly
                805                 810                 815

Cys Ile Ala Leu Arg Leu Glu Ala Thr Glu Thr Gln Leu Pro Ile Tyr
            820                 825                 830

Thr Pro Leu Thr His His Gly Glu Leu Thr Gly His Phe Gln Gly Glu
        835                 840                 845

Ile Lys Leu Gln Thr Ser Gln Gly Lys Thr Arg Glu Lys Leu Tyr Asp
    850                 855                 860

Phe Val Lys Thr Glu Arg Asp Glu Ser Ser Gly Pro Lys Thr Leu Lys
865                 870                 875                 880

Ser Leu Thr Ser His Asp Pro Met Lys Gln Trp Glu Val Thr Ser Arg
                885                 890                 895

Ala Pro Pro Cys Ser Gly Ser Ser Ile Thr Glu Ile Ile Asn Pro Asn
            900                 905                 910

Tyr Met Gly Val Gly Pro Phe Gly Pro Pro Met Pro Leu His Val Lys
        915                 920                 925

Gln Thr Leu Ser Pro Asp Gln Gln Pro Thr Ala Trp Ser Tyr Asp Gln
    930                 935                 940

Pro Pro Lys Asp Ser Pro Leu Gly Pro Cys Arg Gly Glu Ser Pro Pro
945                 950                 955                 960

Thr Pro Pro Gly Gln Pro Pro Ile Ser Pro Lys Lys Phe Leu Pro Ser
                965                 970                 975

Thr Ala Asn Arg Gly Leu Pro Pro Arg Thr Gln Glu Ser Arg Pro Ser
            980                 985                 990

Asp Leu Gly Lys Asn Ala Gly Asp Thr Leu Pro Gln Glu Asp Leu Pro
        995                 1000                1005

Leu Thr Lys Pro Glu Met Phe Glu Asn Pro Leu Tyr Gly Ser Leu Ser
    1010                1015                1020

Ser Phe Pro Lys Pro Ala Pro Arg Lys Asp Gln Glu Ser Pro Lys Met
1025                1030                1035                1040

Pro Arg Lys Glu Pro Pro Pro Cys Pro Glu Pro Gly Ile Leu Ser Pro
                1045                1050                1055

Ser Ile Val Leu Thr Lys Ala Gln Glu Ala Asp Arg Gly Glu Gly Pro
```

-continued

```
                   1060                1065                1070
Gly Lys Gln Val Pro Ala Pro Arg Leu Arg Ser Phe Thr Cys Ser Ser
             1075                1080                1085
Ser Ala Glu Gly Arg Ala Ala Gly Gly Asp Lys Ser Gln Gly Lys Pro
         1090                1095                1100
Lys Thr Pro Val Ser Ser Gln Ala Pro Val Pro Ala Lys Arg Pro Ile
1105                1110                1115                1120
Lys Pro Ser Arg Ser Glu Ile Asn Gln Gln Thr Pro Pro Thr Pro Thr
             1125                1130                1135
Pro Arg Pro Pro Leu Pro Val Lys Ser Pro Ala Val Leu His Leu Gln
                 1140                1145                1150
His Ser Lys Gly Arg Asp Tyr Arg Asp Asn Thr Glu Leu Pro His His
             1155                1160                1165
Gly Lys His Arg Pro Glu Glu Gly Pro Pro Gly Pro Leu Gly Arg Thr
         1170                1175                1180
Ala Met Gln
1185
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ile Asn Pro Asn Tyr
1               5
```

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Glu Asn Pro Leu Tyr
1               5
```

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Val Pro Ala Glu Gly Val Ser Ser Leu Asn Glu Met Ile Asn Pro
1               5                   10                  15
```

(2) INFORMATION FOR SEQ ID NO:12:

(i) SEQUENCE CHARACTERISTICS:
        (A) LENGTH: 6 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Asn Glu Met Ile Asn Pro
1               5

(2) INFORMATION FOR SEQ ID NO:13:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Val Pro Ala Glu Gly Val
1               5

(2) INFORMATION FOR SEQ ID NO:14:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Asp Gly Ser Phe Leu Val Arg
1               5

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Pro Pro Ser Gln Pro Pro Leu Ser Pro
1               5

(2) INFORMATION FOR SEQ ID NO:16:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Pro Val Lys Pro Ser Arg
1               5

(2) INFORMATION FOR SEQ ID NO:17:

(i) SEQUENCE CHARACTERISTICS:
```

```
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Pro Pro Leu Ser Pro Lys Lys
1               5

(2) INFORMATION FOR SEQ ID NO:18:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Pro Pro Leu Pro Val Lys
1               5

(2) INFORMATION FOR SEQ ID NO:19:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:19:

Trp Leu Gly Asp Leu Asn Tyr Arg
1               5

(2) INFORMATION FOR SEQ ID NO:20:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Lys Tyr Asn Leu Pro Ser Trp Cys Asp Arg Val Leu Trp
1               5                   10

(2) INFORMATION FOR SEQ ID NO:21:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

Asn Pro Xaa Tyr
1

(2) INFORMATION FOR SEQ ID NO:22:
```

```
        (i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:22:

GACATCGATG GGATTTGAAT CATCTTCAGT T                                    31

(2) INFORMATION FOR SEQ ID NO:23:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GTAACGGGTC TAGCCCTAGG CCTAGGAAGG CTAGGT                               36

(2) INFORMATION FOR SEQ ID NO:24:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Val Pro Ala Cys Gly Val Ser Ser Leu Asn Glu Met Ile Asn Pro
1               5                   10                  15
```